US012173299B2

(12) United States Patent
Cleland

(10) Patent No.: US 12,173,299 B2
(45) Date of Patent: Dec. 24, 2024

(54) ENGINEERED NUCLEASES TO GENERATE MUTATIONS IN PLANTS

(71) Applicant: PIONEER HI-BRED INTERNATIONAL, INC., Johnston, IA (US)

(72) Inventor: Meridith Cleland, Greeley, CO (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 266 days.

(21) Appl. No.: 17/419,769

(22) PCT Filed: Jan. 2, 2020

(86) PCT No.: PCT/US2020/012040

§ 371 (c)(1),
(2) Date: Jun. 30, 2021

(87) PCT Pub. No.: WO2020/142598

PCT Pub. Date: Jul. 9, 2020

(65) Prior Publication Data

US 2022/0064657 A1 Mar. 3, 2022

Related U.S. Application Data

(60) Provisional application No. 62/788,578, filed on Jan. 4, 2019.

(51) Int. Cl.
*C12N 15/82* (2006.01)

(52) U.S. Cl.
CPC ..... *C12N 15/8247* (2013.01); *C12N 15/8213* (2013.01)

(58) Field of Classification Search
None
See application file for complete search history.

(56) References Cited

FOREIGN PATENT DOCUMENTS

| | | | | |
|---|---|---|---|---|
| WO | 2009007091 | A2 | 1/2009 | |
| WO | 2011075716 | A1 | 6/2011 | |
| WO | WO-2017205665 | A1 * | 11/2017 | ......... C12N 15/8213 |

OTHER PUBLICATIONS

"Translocation Protein Sec62." , 网站维护 tbir.njau.edu.cn/NhCCDbHubs/BlastFile_allFile.action?directfile=gf &functionType=gf. Accessed Aug. 7, 2023. (Year: 2023).*

Hu, Shuai, et al. "AtSec62 is critical for plant development and is involved in ER-phagy in *Arabidopsis thaliana*." Journal of integrative plant biology 62.2 (2020): 181-200 (Year: 2019).*

Jung, Sung-jun, et al. "Cotranslational targeting and post-translational translocation can cooperate in Spc3 topogenesis." Journal of Molecular Biology 433.18 (2021): 167109. (Year: 2021).*

Dec. 19, 2002 (Dec. 19, 2002), "B0NFL32TF B0_I.6_2_KB_tot *Brassica oleracea* genomic clone B0NFL32, genomic survey sequence.", XP055689503, retrieved from EBI accession No. EM_GSS:BZ461701 Database accession No. BZ461701 sequence.

Shuai Hu et al: "AtSec62 is critical for plant development and is involved in ER-phagy in *Arabidopsis thaliana*", Journal of Integrative Plant Biology, vol. 62, No. 2, Nov. 19, 2019 (Nov. 19, 2019), pp. 181-200, XP055688853, GB ISSN: 1672-9072, DOI: 10.1111/jipb.12872 p. 194, col. 1, paragraph 2—col. 2, paragraph 1; figure 1 Form PCT/.

* cited by examiner

*Primary Examiner* — Weihua Fan
*Assistant Examiner* — Brian James Sullivan

(57) ABSTRACT

Methods are provided to mutate, in a targeted manner, the genome of a plant cell using a double stranded DNA break inducing enzyme. Also provided are plants, in particular *Brassica* plants that yield seeds producing oils having a reduced total saturated fatty acid content, and method for making such plants.

7 Claims, 28 Drawing Sheets

Specification includes a Sequence Listing.

ATGAAGAAGCCTGCCGGAACCGAGAAGAAGAGGGTTAAACGATCATCCGATGCTCCACCTAAGGTT
CGCTCTCTTCTCTCATTGCTTGCTAAATCAATTCCAAATAAAACTTGTTCTAAGGTTACGTAACCCTTG
CTTTTGATCTGCTTCGCTCTCTCATGGAACGATGACCCTGCGATTATATGGAATTACAGTCCTTGTTCG
TCAGACACATGTATATGTTCCTTGTCTGAATAATGTCAAACACTGTTTTGTTTTTGTTTTTGTTAGAAGA
AAGGTGTGACGAAGGATTTGTTTCAGTTGTTTGCTGAGAAAGTTAGAGACAACAAGGGGTTGGAATCA
AGATGGGCTGTTATGGAGCAAGCGCGAGTCGAGTACTTCAGAGGGAAAGATTTTGTTAGCTTCGTGAA
GAATCACCCCGAGTGTAAAGAGGTTCTTGAAGAAGATAGTGACCTCGACGCTGAAGATATCGCTAAT
GTGTTGTTGGGGAAGAACCTTTTGGTTAGATGTGATCGTGTTACCAAAACCCTTCGTCCCGGGAAGAA
AAAGCTCTCTACTTGGCCTGCTCATCTTGAGATTTTCCGTGTAAGTTGGTTCATATGCTAAGAGTATGA
TTCTATAACAGAGTGCCTGTGTTTGACTTGATAGTTAGCTTCTAAAGACTATTGCTATTGAACATTTTGT
CTCATCTTAGCTTCAAGCCCATTCAATTGCGCAAATACATTAGCGTTTGATTTGTTTTTTGCTGTTTCTA
ATGCAGGATGATCAAGCTTTCTCTGAAACTGATGCGTTTTTTGCATGGACGTTTGAGAAACGGCATCC
ACTCTGGCAAACACTTTTGTCCTTCTTCTGGCCTGTATTGACTCTCGCGATCTGTTTGTTTCCTGTGTA
CCCACACCGTTGCAAACTCATTGTTCTCTACTCGTGTGCTGGCATTCTTTTGATGATTCTCTCCTTGCT
TTTTGGTAAACTCTGCATATGTAATATGTTTAGTGTGCTTTATTTCTCGAGTGTGTTGTTTCACTCTGATG
ACACTCTGTTATTGGCTCTTAATCTAGGCGATGATTTGCTGGCTATATATGCCTAACTTATCCATGTCTT
GGAGACTGGTGGTGATATGTAGTTTTAATTTGGATTTCTTCTTCATTACCTTGAATGTTGCAGTGAGAG
CAGTTGCTTTTGGTGCTATGTGGATTCTTTTTGGAAAGCGTGTATGGTTCTTCCCCAACATTCTTGCAG
AGGAAGCCACATTGAAGGAACTATTCCGTTTCTGGCCAAAGAAAGACGAGGAAGAACCTCCCAAGTG
GACATCTCGACTTTTCTACACAGTTGTGGCCGTTGTTGTTGTCATGCTGCTCAGGCGCCACGCTCCTG
ATGAGGCTGCTCGTGCCAGGTATTTTAACTTAAACCAAGATAACAATAATTGAAGTGATTCCCTCTCCT
CAAGAGAAGATTGTTTTCTCTAAGTGCTATATGAGTTCTATGGTGGACTTGTGATGATTTTTTTGTGCAT
CCAGGTACCAAAGAAGGATGTCAAACATCATTGATGATGTCCTTGAGTGGTCACCGAAGCTGGCACT
CTCTGGTTTAATGGAGAATCAGCCACCTGTGAACATCACAGAGGCGGCTAACAACTCCTCAGATGCC
GCAGGTCCAGACCATACTGAAGAGGCCGACCTAGACGAAACTCAAGGCGAGGAGGAAGCTGAAGA
CTTGACCAACTCTGATATAAAAACATAA (SEQ ID NO: 1)

FIG. 1A

ATGCAGGATGATCAAGCTTTCTCTGAAACAGATGCGTTTTTTGCATGGACGTTTGAGAAACGGCACCC
ACTCTGGCAAACACTTTTGTCCTTCTTCTGGCCTGTATTGACTCTCGCGATCTGTTTGTTTCCTGTGTA
CCCACACCGTTGCAAACTCATTGTTCTCTACTCGTGTGCTGGCATTCTTTTGATGATTCTCTCCTTGCT
TTTTGGTAAGCTCTGCATATGTAATATGTTTAGTGTGCTTTATTTCTCGAGTGTGTTGTTTCACTCTGATG
ACACTCTGTTTTTGGCTCTTAATCTAGGCGAT (SEQ ID NO: 2)

FIG. 1B

ATGCAGGATGATCAAGCTTTCTCTGAAACAGATGCGTTTTTTGCATGGACGTTTGAGAAACGGCACCC
ACTCTGGCAAACACTTTTGTCCTTCTTCTGGCCTGTATTGACTCTCGCGATCTGTTTGT---------
ACCCACACCGTTGCAAACTCATTGTTCTCTACTCGTGTGCTGGCATTCTTTTGATGATTCTCTCCTTGC
TTTTTGGTAAGCTCTGCATATGTAATATGTTTAGTGTGCTTTATTTCTCGAGTGTGTTGTTTCACTCTGAT
GACACTCTGTTTTTGGCTCTTAATCTAGGCGAT (SED ID NO: 3)

FIG. 1C

MEGANUCLEASE TARGET

WILD-TYPE DNA
AACACTTTTGTCCTTCTTCTGGCCTGTATTGACTCTCGCTATCTGTTTGTTTCCTGTGTACCCACACCGTTGC
AAACTCATTGTTCTCTACTCGTGTGCTGGCATTCTTTTGATGATTCTCTCTTTGCTT

MUTANT DNA
AACACTTTTGTCCTTCTTCTGGCCTGTATTGACTCTCGCGATCTGTTTG---------
TACCCACACCGTTGCAAACTCATTGTTCTCTACTCGTGTGCTGGCATTCTTTTGATGATTCTCTCCTTG
CTT

FIG. 1D

ATCCACTGTGGCAAACGCTTTTGTCCTTCTTCTGGCCTGTATTGACTCTCGCTATTTGTTTGTTTCCTGT
---------
GTACCCACACCGTTGCAAACTCATTGTTCTCTACTCATGTGCTGGCATTCTTTTGATGATTCTCTCCTT
GCTTTTCGGTAAGCTCTACATATATTAACCTGCTTAAAGTAGGTTTATATTGGCTTATGTTTTTTCTTGAT
TACCGTGGATGTTGCAGTGAGAGCAGTTGCTTTCGGTGCGATGTGGATTCTTCTTGGAAAGCGTGTCT
GGTTCTTCCCCAACATTCTTGC (SEQ ID NO: 6)

FIG. 1E

ATCCACTGTGGCAAACGCTTTTGTCCTTCTTCTGGCCTGTATTGACTCTCGCTATTTGTTTGTTTCCTGT
GTACATATTGTACCCACACCGTTGCAAACTCATTGTTCTCTACTCATGTGCTGGCATTCTTTTGATGAT
TCTCTCCTTGCTTTTCGGTAAGCTCTACATATATTAACCTGCTTAAAGTAGGTTTATATTGGCTTATGTT
TTTTCTTGATTACCGTGGATGTTGCAGTGAGAGCAGTTGCTTTCGGTGCGATGTGGATTCTTCTTGGAA
AGCGTGTCTGGTTCTTCCCCAACATTCTTGC (SEQ ID NO: 7)

FIG. 1F

MEGANUCLEASE TARGET

WILD-TYPE DNA ACGCTTTTGTCCTTCTTCTGGCCTGTATTGACTCTCGCTATTTGTTTGTTTCCTGT------------

GTACCCACACCGTTGCAAACTCATTGTTCTCTACTCATGTGCTGGCATTCTTTTGATGATTCTCTCCTTGCTT

MUTANT DNA
ACGCTTTTGTCCTTCTTCTGGCCTGTATTGACTCTCGCTATTTGTTTGTTTCCTGTGTACATATTGTACCCACACCGTTGCAAACTCATTGTTCTCTACTCATGTGCTGGCATTCTTTTGATGATTCTCTCCTTGCTT

FIG. 1G

ATGGAGCAAGCGCGTGTCGAATACTTCAGAGGCAAAGATTTCGTCAGCTTCATTAAGAATCACCCCGAGTGTAAAGAGATTCTCGAAGAAGATAAAGACCTCGACACTGAAGATATCGCCAATGTGTTGTTGGAGAAGAACCTTTTGGTCCGATGTGATCGTGTGACTAAAACCCTTCGTCCCGGGAAGAAAAAGCTCTC (SEQ ID NO: 9)

FIG. 1H

ATGGAGCAAGCGCGTGTCGAATACTTCAGAGGCAAAGATTTCGTCAGCTTCATTAAGAATCACCCC----

GTAAAGAGATTCTCGAAGAAGATAAAGACCTCGACACTGAAGATATCGCCAATGTGTTGTTGGAGAAGAACCTTTTGGTCCGATGTGATCGTGTGACTAAAACCCTTCGTCCCGGGAAGAAAAAGCTCTC (SEQ ID NO: 10)

FIG. 1I

MEGANUCLEASE TARGET

WILD-TYPE DNA
AGAGGCAAAGATTTCGTCAGCTTCATTAAGAATCACCCCGAGTGTAAAGAGATTCTCGAAGAAGATAAAGACCTCGACACTGAAGATATCGCCAATGTGTTGTTGGAGAAGAACCTTTTGGTCCGAT

MUTANT DNA AGAGGCAAAGATTTCGTCAGCTTCATTAAGAATCACCCC----
GTAAAGAGATTCTCGAAGAAGATAAAGACCTCGACACTGAAGATATCGCCAATGTGTTGTTGGAGAAGAACCTTTTGGTCCGAT

FIG. 1J

ATGCAAAGAACATGGCATCATATCTCCATGTCGTAAGCTTCATAGGTTTTCTCTCTATCCTTAGATTAC
TCTATCCTCTCCTGAAATGGTTCATCACGAGATTCCTCCTCACTGACCCCAGGCGACTCAAGAGTTAT
GGCTCGTGGGCTATGGTCACTGGAGCCACAGATGGGATCGGACAAGCCTTTGCTCACGAGCTGGCA
AAACACGGCCTTAACCTCGTCCTAGTCAGCAGAAACCCTTCGAAGCTAGCTTCTGTCTCCGATGATTT
CAGACAAGAATTTCCCCAAATCAAGATCAAGATCATTCCCTTTGACTTCTCCTCTGGTAATACTAAATG
CACTTTCTTATTTTTCAATGCAGTCTTCACTTCACTTTTGGTCAATCCTATAGAACTAGGCGTCTATATG
TCTCTGTGTGAGCATAACTACAGGGCTGTAAACTTGGAAAATATATTCTTGTTTCAACAGCTAGCCAG
GATGAAAACACACAATTATTCAATCCAAATGCAAAATGAACCGAGTTAATATAGTATACAATTACTCTA
GAATGCAAGATCCACTTTAATTTGTTATAGTATAACGTTACTAACTAATACATGCATTTACAAGATTAAA
CTAAAGATCAAATGCTTTCTTAAATATTTTTTTGTTAGTTTTTGTATATTTATTATTTTAGGGGGCCGGGT
AAACTTCTAAGCTATTTCAGTCTACAAAGATGATACGCATGCAAAACTAAAGATGGTGGCAGATGTAA
TATAGAAATGAAGGGTGTTGTATTTATGAGCAGTGATAAATTGGAGAAATGTGCAGAAAGAGGATATG
AAGCAATCGAGGAGGGAATCAGAGGCCTTGAAGTTGGAATTCTGATAAACAACGTTGGTATAACTTAT
CCACGAGCCATGTTCTTCCACGAGGTTGACGAACTCACATGGACCAAAATCCTTAGGGTTAATCTTGA
AGCCACCACTTGGGTCACAAGATCTCTCATCGGACCAATGCTTCACCGCCGTCGAGGAGCTATCATA
AATATTAGCTCCGGCGCCGCAGTTGTTGTCCCTTCGCATCCACTCTATGCCATCTACGCCGCCACCA
AAGCGTTAGGACTTTAACTTTTCTTTTATTTACTGCTTCTAAAGTTCAATGCACATTTTATAAATATAAGC
ATACTAACCAACAAAATTAGAAGAAAACTAGAGAGATCTTAAGAATAATATTAGATGGGAGTAAGAAA
AAGATTCACAAGATATCTTATGTCATTTAACACAGAAGTTAATCTCTAACCAAGATAAAGTAGTAATTT
AGAAAACTAAACTTTGGTTGTAATTAGCTCTAACTAAAAGTCTAAAAGATCTGAACTTAAAGTTAGTTA
CTTAGCTCAATTATAAGTTTGTAGTTATTTAAAATCTCATATATATTAAAAGAGAAACATTACAACATTTT
AACTATGACATGTCATCATTAGAATGCTTTTTAAAATTTCTAAAAAAATATGTTGGTCCACTAATCATAT
ATTATATATACTTCTCCTTAAACTAACCATGAAATTAATTAACAATTAACAATTACTATTATTTTTCTTAA
ATAACTACGAAATTACCAAAAGTGAATAAAATATATATTTGACAGTTAATGATTTCAATAAAAAAAATTT
GACAACAATTTACATATCTTCATTATTATATAATGTTATATTATTAAAATAAATTAAATAATTACATTAAC
CATATAATAAAAAATTAGATTTTTTCGTATGTGTTATATTTTGAATTTTAAAAAGGACTATAAATAACAAA
AATCGTTAAAAGTCTCATATTGGAAATTTTATGATCTATAGTTTAATTTTTTTGTTTTAATAAAATACAAAT
GATCGTAAAACCATACAAGTAAAAATCACATTTATTAGATATTGAGATTAATATATATATAGGACTTATG
AATGATATAATTATGGTTGAACGGTCAAAGTTCGTATTCAATAATTATTAGAATATACTCCCTCCGTTCC
TAAAAGATGCATGTTCTGGAAAAAAAATTTGTTTCAAAAAGATATATTTTTTACTTTTTCAATGTATGATT
TTATGAAAAATTGTAAGTTTCAAAAAAATTAATGGTGTTTATTGAATTTTTATTGGCTAAAAGTTATCGAA
AATTGTTATTTACAAAAAACAATGCATATTTAATGAGTTTTCTTAATATATGTGAAAAGTCTAGAATATG
CATCTTTTAAAAACAGAGGGAGTATATTTCATTCTTAGTATGTGCGCGAATTCATGCATTATATTGGAAT
CTTAAATTCTATTTATTTTAAACTGAAAACTACTAGTAGTACAAAGTTCTGTTTCTTTTCAAATTACTAAC
TACAGCTATATCGGTGACTTGCATGTAGTCATTAAGGTTTCGGTCCGTTCTTTCTATTTAATTTTTTGGT
AGTTATTAGTTGTTGTATAATAAATTGTGTAATCGACTCTATACACGTAGATGTATATAGGTAACCCACC
CACATGTAAGACCCGTGCATTTACGACCTTTTAGCTAGGTGGATTGTTAAAGTAATTATGATGAATCAT
CACGCGACAAAACCTTGTTCTAGTTACTTAGATAGAGTGTTGTTATTTGTAAAAATAACAACTATAAGT
AACGCTTTTACTTTGATAGCATCATAGCAATAGAGCGATCATTTCATTTGACCATATATAAGTTGTTAAA
AATGTCTTCGGTGATTAGGAAAAGCTAATTGTCATTTTGTAAAATGTATAAACTAATTGTCATTTTATTC
ATATCGTTTTATTGATAGAACAAAATGTCAGCTGTTTTATGAATTTTATGCATATTGTCCATAACCATCA
CATGCATGAATTAACGAATACGTGCATGCAGTTATGTTGATAAACTATCAAGATCTTTGCATGTGGAAT
ATAAGCAGTTTGGTATCCACGTCCAATGCCAGGTAACTTTTTGTTTTCTTTTTCTTTTCTCTATAATACTT
TATGATTTCCCATGTAATGTGGCAGGTGCCGTTATATGTGGCAACGAGGATGGTGTCAGAAGTAGCAG
ATATAGATAAACCAAGCTTCTTTGTACCATCGCCGGAAGTATATGCAAAAGCGGCGGTGGAGCAGAT
CGGAATTGGATCACGATGCTCTCCATTTTGGGCTCATTCACTTCAGTGGTTTCTCGCTGGTCTTTTGCC
GGAGAACCTTCTTGATACTTGGCGTCTCTCTATCGGTCTTCGTAGAAGAAGCTTGTCTTAG (SEQ ID NO: 13)

FIG. 2A

GCAGTGATAAATTGGAGAAATGTGCAGAAAGAGGATATGAAGCAATCGAGGAGGGAATCAGAGGCCT
TGAAGTTGGAATTCTGATAAACAACGTTGGTATAACTTATCCACGAGCCATGTTCTTCCACGAGGTTG
ACGAACTCACATGGACCAAAATCCTTAGGGTTAATCTTGAAGCCACCACTTGGGTCACAAGATCTCT
CATCGGACCAATGCTTCACCGCCGTCGAGGAGCTATCATAAATATTAGCTCCGGCG (SEQ ID NO: 14)

FIG. 2B

GCAGTGATAAATTGGAGAAATGTGCAGAAAGAGGATATGAAGCAATCGAGGAGGGAATCAGAGGCCT
TGAAGTTGGAATTC------------------------
ATCCACGAGCCATGTTCTTCCACGAGGTTGACGAACTCACATGGACCAAAATCCTTAGGGTTAATCTT
GAAGCCACCACTTGGGTCACAAGATCTCTCATCGGACCAATGCTTCACCGCCGTCGAGGAGCTATCA
TAAATATTAGCTCCGGCG (SEQ ID NO: 15)

FIG. 2C

MEGANUCLEASE TARGET

WILD-TYPE DNA

AGGGAATCAGAGGCCTTGAAGTTGGAATTCTGATAAACAACGTTGGTATAACTTATCCACGAGCCATG
TTCTTCCACGAGGTTGACGAACTCAC

MUTANT DNA

AGGGAATCAGAGGCCTTGAAGTTGGAATTC------------------------
ATCCACGAGCCATGTTCTTCCACGAGGTTGACGAACTCAC

FIG. 2D

GCAGTGATAAATTGGAGAAATGTGCAGAAAGAGGATATGAAGCAATCGAGGAGGGAATCAAAGGCCT
CGAAGTTGGAATTCTGATAAACAACGTTGGTATAACTTATCCACGAGCCATGTTCTTCCACGAGGTTG
ACCAACTCACATGGACCAAAATCCTTAGGGTTAATCTTGAAGCCACCACCTGGGTCACAAGATCTCT
CATCGGACCAATGCTTCACCGCCGTCGAGGAGCTATCATAAATATTAGCTCCGGCG (SEQ ID NO: 18)

FIG. 2E

GCAGTGATAAATTGGAGAAATGTGCAGAAAGAGGATATGAAGCAATCGAGGAGGGAATCAAAGGCCT
CGAAGTTGGAATTCTGATA----------------
TAAATTATCCACGAGCCATGTTCTTCCACGAGGTTGACCAACTCACATGGACCAAAATCCTTAGGGTT
AATCTTGAAGCCACCACCTGGGTCACAAGATCTCTCATCGGACCAATGCTTCACCGCCGTCGAAGAG
CTATCATAAATATTAGCTCCGGCG (SEQ ID NO: 19)

FIG. 2F

MEGANUCLEASE TARGET

WILD-TYPE DNA
AGGGAATCAAAGGCCTCGAAGTTGGAATTCTGATAAACAACGTTGGTATAACTTATCCACGAGCCATG
TTCTTCCACGAGGTTGACCAACTCAC

MUTANT DNA
AGGGAATCAAAGGCCTCGAAGTTGGAATTCTGATA-------------
TAACTTATCCACGAGCCATGTTCTTCCACGAGGTTGACCAACTCAC

FIG. 2G

TAGGCTTTCTTTCTCTCGTTAGACTATTCCTCCCTCTCCTAAAATGGTTCATCACGAGATTCCTACTCA
CAAACCCTAAGCGGCTCAAGCGTTATGGCTCGTGGGCTATGGTCACTGGAGCCACAGATGGAATCG
GACTAGCCTTCGCTCACGAGCTAGCA-
AAACACGGCCTCAACCTTATCCTAGTCAGCAGAAACCCTTTGAAGCTCGCCTCCGTCTCCGATGATT
TCCGACAAGAGTTTCCACAAATAAAGATCAAGATCATTCCCTTTGACTTCTCCTCTGGTAATTCTAAAT
GCACTTTCTTACTTTTTCAATGCAGTCTGGCCTCACTTCTTCTTCGGCCAATCGTATTGAGCTAGTTCA
CAAAGAGTTATCGACTACTCGTT (SEQ ID NO: 22)

FIG. 2H

TAGGCTTTCTTTCTCTCGTTAGACTATTCCTTCCTCTCCTAAAATGGTTCATCACGAGATTCCTACTCA
CAAACCCTAAGCGGCTCAAGCGTTATGGCTCGTGGGCTATGGTCACTGGAGCCACAGATGGAATCG
GACGAGCCTTCGCTCACGAGCTAGCAAAAACACGGCCTCAACCTTATCCTAATCAGCAGAAACCCTT
TGAAGCTCGCCTCCGTCTCCGATGATTTCCGACAAGAGTTTCCACAAATCAAGATCAAGATCATTCCC
TTTGACTTCTCCTCTGGTAATTCTAAATGCACTTTCTTACTTTTTCAATGCAGTCTGGTCTCACTTCTTCT
TCGGCCAATCGTATTGAGCTAGTTCACACAGAGTTATCGACTACTCGTT (SEQ ID NO:23)

FIG. 2I

MEGANUCLEASE TARGET

WILD-TYPE DNA
TGGTCACTGGAGCCACAGATGGAATCGGACTAGCCTTCGCTCACGAGCTAGCA-
AAACACGGCCTCAACCTTATCCTAGTCAGCAGAAACCCTTT

MUTANT DNA
TGGTCACTGGAGCCACAGATGGAATCGGACGAGCCTTCGCTCACGAGCTAGCAAAAACACGGCCTC
AACCTTATCCTAATCAGCAGAAACCCTTT

FIG. 2J

TAGGCTTTCTTTCTCTCGTTAGACTATTCCTCCCTCTCCTAAAATGGTTCATCACGAGATTCCTACTCA
CAAACCCTAAGCGGCTCAAGCGTTATGGCTCGTGGGCTATGGTCACTGGAGCCACAGATGGAATCG
GACTAGCCTTCGCTCACGAGCTAGCAAAACACGGCCTCAACCTTATCCTAGTCAGCAGAAACCCTTT
GAAGCTCGCCTCCGTCTCCGATGATTTCCGACAAGAGTTTCCACAAATAAAGATCAAGATCATTCCCT
TTGACTTCTCCTCTGGTAATTCTAAATGCACTTTCTTACTTTTTCAATGCAGTCTGGCCTCACTTCTTCT
TCGGCCAATCGTATTGAGCTAGTTCACAAAGAGTTATCGACTACTCGTTTGTGTGTGTGT (SEQ ID NO: 26)

FIG. 2K

TAGGCTTTCTTTCTCTCGTTAGACTATTCCTTCCTCTCCTAAAATGGTTCATCACGAGATTCCTACTCA
CAAACCCTAAGCGGCTCAAGCGTTATGGCTCGTGGGCTATGGTCACTGGAGCCACAGATGGAATCG
GACGAGCCTTCGCTCACG-----------------
GCCTCAACCTTATCCTAATCAGCAGAAACCCTTTGAAGCTCGCCTCCGTCTCCGATGATTTCCGACA
AGAGTTTCCACAAATCAAGATCAAGATCATTCCCTTTGACTTCTCCTCTGGTAATTCTAAATGCACTTT
CTTACTTTTTCAATGCAGTCTGGTCTCACTTCTTCTTCGGCCAATCGTATTGAGCTAGTTCACACAGAG
TTATCGACTACTCGTTTGTGTGTGTGT (SEQ ID NO: 27)

FIG. 2L

MEGANUCLEASE TARGET

WILD-TYPE DNA

TGGTCACTGGAGCCACAGATGGAATCGGAC
TAGCCTTCGCTCACGAGCTAGCAAAACACGGCCTCAACCTTATCCTAGTCAGCAGAAACCCTTT

MUTANT DNA

TGGTCACTGGAGCCACAGATGGAATCGGACGAGCCTTCGCTCACG---------------
GCCTCAACCTTATCCTAATCAGCAGAAACCCTTT

FIG. 2M

TAGGCTTTCTTTCTCTCGTTAGACTATTCTTTCCTCTCCTGAAATGGTTCATCACGAGATTCCTACTCAC
AAACCCTAAGCGGCTCAAACGTTATGGCTCGTGGACTATGGTCACTGGAGCCACAGATGGAATCGGA
CGAGCCTTTGCTCACGAGCTAGCAAAA-
CACGGCCTTAACCTCATCCTAGTCAGCAGAAACCCTTCGAAGCTCGCTTCCGTCTCCGATGATTTCC
GACAAGAGTTTCCACAAATTAAGATCAAGATCATTCCTTTTGACTGCTCTGGTAATTCTAAATGCACTT
TCTTACTTTTTCATTTCAGTGCTCACTTCTTTTTCGGCCAATCGTCTTGAGCTAGTCCACACAGAGTTCT
CGACTACTCGTTTGTGTGTGTGCTCACGCATATAATTACTACATGATTGTAACATTGGAAAAATTATTGT
TCTTTCTCAAAAGAAAAATCTTGATTCAACAGCCAGGATAAAAAATATAATTACTCCGCACAAATAATT
CGAAACATAAATGAATATATAGAGTACACAATTACATTTAGTAGTGTATTTGTAAGAGAGCCGCAAA
(SEQ ID NO: 30)

FIG. 2N

TAGGCTTTCTTTCTCTCGTTAGACTATTCTTTCCTCTCCTGAAATGGTTCATCACGAGATTCCTACTCAC
AAACCCTAAGCGGCTCAAACGTTATGGCTCGTGGACTATGGTCACTGGAGCCACAGATGGAATCGGA
CGAGCCTTTGCTCACGAGCTAGCAAAAACACGGCCTTAACCTCATCCTAGTCAGCAGAAACCCTTCG
AAGCTCGCTTCCGTCTCCGATGATTTCCGACAAGAGTTTCCACAAATTAAGATCAAGATCATTCCTTTT
GACTGCTCTGGTAATTCTAAATGCACTTTCTTACTTTTTCATTTCAGTGCTCACTTCTTTTTCGGCCAAT
CGTCTTGAGCTAGTCCACACAGAGTTCTCGACTACTCGTTTGTGTGTGTGCTCACGCATATAATTACTA
CATGATTGTAACATTGGAAAAATTATTGTTCTTTCTCAAAAGAAAAATCTTGATTCAACAGCCAGGATA
AAAAATATAATTACTCCGCACAAATAATTCGAAACATAAATGAATATATAGAGTACACAATTACATTTA
GTAGTGTATTTGTAAGAGAGCCGCAAA (SEQ ID NO: 31)

FIG. 2O

MEGANUCLEASE TARGET

WILD-TYPE DNA
TGGTCACTGGAGCCACAGATGGAATCGGACGAGCCTTTGCTCACGAGCTAGCAAAA-
CACGGCCTTAACCTCATCCTAGTCAGCAGAAACCCTTC

MUTANT DNA
TGGTCACTGGAGCCACAGATGGAATCGGACGAGCCTTTGCTCACGAGCTAGCAAAAACACGGCCTT
AACCTCATCCTAGTCAGCAGAAACCCTTC

FIG. 2P

ATGGAGATTTTGGATTCTGGAGGCGTCACTATGCCGACGGAGAACGGTGGTGCCGATCTCGATACGC
TTCGTCACCGGAAACCGAGATCGGATTCTTCCAATGGACTTCTTCCTGATTCCGTAACTGTTTCCGAT
GCTGACGTGAGGGATCGGGTTGATTCAGCTGTTGAGGATACTCAAGGAAAAGCCAATTTGGCCGGAG
AAAACGAAATTAGGGAATCCGGTGGAGAAGCGGGGGGAAACGTGGATGTAAGGTACACGTATCGGC
CGTCGGTTCCAGCTCATCGGAGGGTGAGGGAGAGTCCACTCAGCTCTGACGCCATCTTCAAACAGG
TAATCAATCTTAGAGGAGAATTTCAAATTGACTTCTTATCTTCTTGACTTGCATATTTAAAGATTATATTT
TTTTTTTTATTTGAGTAATGTGATTGTTTTCATCATGGCAGAGCCATGCTGGACTATTCAACCTGTGTGT
AGTAGTTCTTGTTGCTGTAAACAGTAGACTCATCATCGAAAATCTCATGAAGGTTTGTTACTTACTTCTT
TCTCCTCTTCCTTCAAACTTATGAGACCTTACATTTGTTCATTCATGTAGTACGGTTGGTTGATCAGAA
CTGATTTCTGGTTTAGTTCAACGTCTCTGCGAGATTGGCCCCTTTTCATGTGTTGGTACAAATGCTTCT
TCTTTCTTTGTACATATGGTGATTCAGATTTTTTCAAGTTTTTGAACTTTATGTGGCAGTCTCTCCCTTTC
AATCTTTCCTTTGGCTGCCTTTACCGTCGAGAAATTAGTACTTCAGAAATGCATATCTGAACCTGTGAG
TAAACTGCTGTCTATCCTTTACAGGGTTGTTCGTTGAACGACAAATTTTTATCCTGAACAACTTATAAGT
TTCTTTCTGTAGGTTGTCATCATTCTTCATATTATTATCACCATGACCGAGGTCTTGTATCCAGTCTATG
TCACTCTAAGGTGAGATTTAAGCTTGTGATACTCTTTTTTTTGTTAAAGTTTTGTTTGCTGACTAGATGAT
CTTGAAAACGGACAGGTGTGATTCCGCCTTCTTATCAGGTGTCACGTTGATGCTCCTCACTTGCATTG
TGTGGCTGAAGTTGGTTTCTTACGCTCATACTAACTATGACATAAGAACCCTAGCTAATTCATCTGATA
AGGTAAAAGAAGTGATATAATATTGGTCACTTGCATTGTGTTTTACTATTTTGACCAGACACTGTTGAA
AACTGTAGGCCAATCCTGAAGTCTCCTACTATGTTAGCTTGAAGAGCTTGGCGTATTTCATGCTTGCT
CCCACATTGTGTTATCAGGTAATCTGATGCGTCTTCTGCTAATTGTATCATACATTATCTTTCACTTGCA
AAAGTTTCTTGTCTAAAACCTTGCGTCTTCGCTTTACCCAGCCGAGCTATCCACGTTCTCCATGTATCC
GGAAGGGTTGGGTGGCTCGTCAATTTGCAAAGCTGATCATATTCACTGGATTCATGGGATTTATAATA
GAGCAAGTGCGTTTTTAACCTTTCCTTGTGAAAATCATCATTTCTGCATTGTTACCCGCTTAACTTCAT
GTTCTTTTGGTACTTCTTTGTTGCAGTATATAAATCCTATTGTTAGGAACTCAAAACATCCTTTGAAAGG
GGATCTCTTATACGGTGTTGAAAGAGTGTTGAAGCTTTCAGTTCCAAATTTATACGTGTGGCTCTGCAT
GTTCTACTGCTTCTTCCACCTTTGGTATGCCGCCATCCCATCACATGATTAATTTAGTTTCTCAGAGAC
TGAGATGTAATGTCAGTTTCTGATCATAAACCACGTTGCACTGTTCTTGTCCACAGGTTAAACATATTG
GCAGAGCTCCTCTGCTTCGGGGATCGTGAATTCTACAAAGATTGGTGGAATGCAAAAAGCGTGGGAG
ATGTGAGTTTTCATCAATCTTGTCTTACTCAAAAATCATATTATGTTTACGTTACTAACCAAAATTCATG
TACGCACTGTCTACCTTTGTCAGTATTGGAGAATGTGGAATATGGTATGGTTCTCTTCTTGAAACATCC
CCTTCTTTTTTTATACAAAGCAGATTAAGAAAAGCTTATTGAGATCTTGTTTTTTCTAATAGCCTGTTCAT
AAATGGATGGTTCGACATGTATACTTTCCGTGCCTTCGCAGAAATATACCGAAAGTGAGTGTAGTTAA
TTGCGATGATCGATATTTTTTTCTGTGCTTCATAAATTTAACCCTCCACTCATTTTTTTCCAGGTACCCG
CTATTATCCTTGCTTTCTTAGTCTCTGCAGTCTTTCATGAGGTATAATACATACCTTCCACATTAACCCT
GGCTCTAGCTATTGAAATAAAGGCTAACACTCAAAAGTATTGTTCTTACTTATATTCTCGTGTGTTACA
AATTTCCTTGCAGTTATGCATCGCAGTTCCTTGTCGTCTCTTCAAACTATGGGCTTTCTTGGGGATTAT
GTTTCAGGTATAAAAGAATTAACAAAGTTTCCGCAGTCAGTTCTCACAAACAATCTTCAAGCTTCTGTC
ACCTTTAGTTACATTTTCTGATCATGCAATGTGTGTTTGAGTAGGTGCCTTTGGTATTTATCACAAACTA
CCTACAAGAAAGGTTTGGCTCCATGGTATGCTCTCTAAACTGGAAAAGTAACTCTTTTGTTTTCTGA
(SEQ ID NO: 34)

FIG. 3A

GTTAGGAACTCAAAGCATCCTCTGAAAGGGGACCTTCTATATGCTATTGAAAGAGTGTTGAAGCTTTC
AGTTCCAAATCTATATGTGTGGCTCTGCATGTTCTACTGCTTCTTCCACCTTTGGTATGCCATGATCCC
GTCTCTTTCAACATGATCTATAAAGATGAACAACAAGAGAAAGGAGAATATCTCATGAAGAAATTGAT
GATATTAGTTTTTTTCACAGTTTGAGATGTAATTTCAGTTTCTGACCAAATCTCTTTGCATTGTTCTTGTT
CAAAGGTTAAACATACTGGCAGAGCTGCTCTGCTTCGGGGACCGTGAATTCTACAAAGATTGGTG
(SEQ ID NO: 35)

FIG. 3B

GTTAGGAACTCAAAGCATCCTCTGAAAGGGGACCTTCTATATGCTATTGAAAGAGTGTTGAAGCTTTC
AGTTCCAAATCTATATGTGTGGCTCTGCAT------
ACTGCTTCTTCCACCTTTGGTATGCCATGATCCCGTCTCTTTCAACATGATCTATAAAGATGAACAACA
AGAGAAAGGAGAATATCTCATGAAGAAATTGATGATATTAGTTTTTTTCACAGTTTGAGATGTAATTTCA
GTTTCTGACCAAATCTCTTTGCATTGTTCTTGTTCAAAGGTTAAACATACTGGCAGAGCTGCTCTGCTT
CGGGGACCGTGAATTCTACAAAGATTGGTG (SEQ ID NO: 36)

FIG. 3C

MEGANULCEASE TARGET

WILD-TYPE DNA
TATAGTGTGGCTCTGCATGTTCTACTGCTTCTTCCACCTTTGGTATGCCATGATCCCATCTCTTTCAAC
ATGATCTATAAAGA

MUTANT DNA TATATGTGTGGCTCTGCAT------
ACTGCTTCTTCCACCTTTGGTATGCCATGATCCCGTCTCTTTCAACATGATCTATAAAGA

MEGANUCLEASE TARGET

WILD-TYPE DNA
TATATGTGTGGCTCTGCATGTTCTACTGCTTCTTCCACCTTTGGTATGCCATGATCCCGTCTCTTTCAA
CATGATCTATAAAGA

MUTANT DNA TATATGTGTGGCTCTGCAT------
ACTGCTTCTTCCACCTTTGGTATGCCATGATCCCGTCTCTTTCAACATGATCTATAAAGA

FIG. 3D

CTATCCACGTTCCCCATGTATACGGAAGGGTTGGGTGGCTCGTCAATTTGCGAAACTGGTCATATTCA
CTGGACTCATGGGATTTATAATAGAGCAGGTGCGTTTTCAACATCTTTCTTTTTATTATAAATCCTTGTG
AAAGTCACCATTTCTGCACATTCGACCGCTTGGCTTCATCTTCTTTTGTTACTTCTTTGGCAGTATATAA
ATCCTATTGTAAGGAACTCAAAGCATCCGTTGAAAGGGGATCTTCTATACGCTATTGAAAGAGTGTTG
AAGCTTTCAGTTCCAAATCTATATGTGTGGCTCTGCATGTTCTACTGCTTCTTCCACCTTTGGTATGTAT
GCCGTGATCCCTTCTCTCTCAACATAATTTCCAAAGATGAACAACAGAAAAAGGATATATATCTCATG
AAGAAATTAATAAGTGTAGGTTTTTCTGATCACAAATCTCTTTGCATTGTTCTTGTCCGCAGGTTAAACA
TATTGGCAGAGCTGCTCTGCTTCGGGGACCGTGAATTCTACAAAGATTGGTG (SEQ ID NO: 39)

FIG. 3E

CTATCCACGTTCCCCATGTATACGGAAGGGTTGGGTGGCTCGTCAATTTGCGAAACTGGTCATATTCA
CTGGACTCATGGGATTTATAATAGAGCAGGTGCGTTTTCAACATCTTTCTTTTTATTATAAATCCTTGTG
AAAGTCACCATTTCTGCACATTCGACCGCTTGGCTTCATCTTCTTTTGTTACTTCTTTGGCAGTATATAA
ATCCTATTGTAAGGAACTCAAAGCATCCGTTGAAAGGGGATCTTCTATACGCTATTGAAAGAGTGTTG
AAGCTTTCAGTTCCAAATCTATATGTGTGGCTCTGCAT----------
TTCTTCCACCTTTGGTATGTATGCCGTGATCCCTTCTCTCTCAACATAATTTCCAAAGATGAACAACAG
AAAAAGGATATATATCTCATGAAGAAATTAATAAGTGTAGGTTTTTCTGATCACAAATCTCTTTGCATTG
TTCTTGTCCGCAGGTTAAACATATTGGCAGAGCTGCTCTGCTTCGGGGACCGTGAATTCTACAAAGAT
TGGTG (SEQ ID NO: 40)

FIG. 3F

MEGANUCLEASE TARGET

WILD-TYPE DNA
CCAAATCTATATGTGTGGCTCTGCATGTTCTACTGCTTCTTCCACCTTTGGTATGTATGCCGTGATCCC
TTCTCTCTCAACATAATTTCCAA

MUTANT DNA
CCAAATCTATATGTGTGGCTCTGCAT----------
TTCTTCCACCTTTGGTATGTATGCCGTGATCCCTTCTCTCTCAACATAATTTCCAA

FIG. 3G

ATGGCAGCGAAGATCTCCCAGCTTGCGTGTTTCTCCTCCACCAACCGCCAATTCCACTTCCAGAACC
GATCGTTTCCAAGCCTTAGGTTCCGTCCCGAGGTAAATTTCTTCGAGTATCTCATGTAAAGGACCGAG
CTTTCGTCGTTTTGATCTGATTACGCTGATGCCCAGTATCGTAATTTCCTGATTGCTGTCGAAAAGTTA
CGAGCTTGATTGGTTTTAGTCCTACTCAGAGACTTAGAAATGGCTCTTCTTTGGACTTGAATTGCATCC
TTCTTTGATAGCTCTGTTCTTTGCTTGTAGCTCTGTGCCTTTTGAATGCGTTATCTGTGCTAATAAGCTT
GGCATGGTGGCAGTCTTTTGTAGTTAGAAGCGTTGTTGATGGGAACAGCTCGGAAACACCAGCTTCTC
TGAGCTATGCAGCTGAGGTTTCGAAACCTTTCGTTGAGAAAACATCTACAGTGGATGAAACTACTACG
GGTAAAGAGGTTATCACAGAGTCGGTAGAGGAACATGTTGCCACAACACAGCCTAAAAGAGCAGCG
AAGATTCATGACTTCTGTTTTGGCATTCCTTATGGTACTTTTTGTGACTCTCTCTCAGAACTTAATTTCA
AATCTTAGCGTTACTGAGCTGCTTGTTAAAGTTCCTAATGCAACTCATATCATATTCATTGTCAGGGTA
ACTTATTGGTGTTATTTTACTTCTCAGGTGGTCTGGTTATGAGTGGAGGATTGCTTGGATTTGCGTTTTC
ACGAAATCTTACAAGTTTAAGTACTGGGGTTCTCTATGGTGGTGGCCTTCTAGCTCTTAGTACGTTGAG
CATGAAGATTTGGCGACAGGGAAAGTCTAGTTTCCCTTATATTCTAGGTCAAGCAGGTAATCTTCATCT
ACTGGTATCTTACACATGATTAGTGGATATATGAAAGAAGTGGGATACTAAAAAGTGTTCATCTCTTAA
CCAAGATCACTATGTCCACATTGTGCTTACTCTCATTCTTTCGATACAATAAATTTGCAGTGCTTTCAG
CTGTCGTCTTCTGGAAGAACTTCACATCTTACTCTATGGTAATTCATCGTCTTTGTGATCATGCTGATTG
TTTAAATGTTGCTTGCTTGACTTCAACTGCTTAATGTTGTACTTTTGCAGACTAAGAAGCTGTTTCCTGC
CGGGCTATTTGCTGTCGTCAGGTGAGAAGTTCTTTTGTGATCTATAAGAGAGTCTAATGTATCTATCTTT
ATTGGCTTAATCATGCAACCTTGTGTTCGTGTCTTTTTCATTGCAGTGCTGCCATGTTGTGTTTCTATTC
GTACGTGGTGCTCTCTGGAGGAAACCCACCTCCAAAGAAACTTAAACCATCTGCTACTACTAGTCCTT
CATACTGA (SEQ ID NO: 43)

FIG. 4A

AAAGAAGTGGGATACTAAAAAGTGTTCATCTCTTAACCAAGATCACTATGTCCACATTGTGCTTACTCT
CATTCTTTCGATACAATAAATTTGCAGTGCTTTCAGCTGTCGTCTTCTGGAAGAACTTCACATCTTACT
CTATGGTAATTCATCGTCTTTGTGATCATGCTGATTGTTTAAATGTTGCTTGCTTGACTTCAACTGCTTA
ATGTTGTACTTTTGCAGACTAAGAAGCTGTTTCCTGCCGGGCTATTTGCTGTCGTCAGGTGAGAAGTTC
TTTTGTGATCTATAAGAGAGTCTAATGTATCTATCTTTATTGGCTTAATCATGCAACCTTGTGTTCGTGT
CTTTTTCATTGCAGTGCTGCCATGTTGTGTTTCTATTCGTACGTGGTGCTCTCTGGAGGAAACCCACCT
CCAAAGAAACTTAAACCATCTGCTACTACTAGTCCTTCATACTGAAGAAACTTCACATAGGTTAGATT
CAAAGATGAAGATCTTCTCTTTTGGTGGCTCTTGTGCGTTGCATTCCTGGTGTAATTTTATACTTTTGAC
TTTTGAGGCAACAACTGTG (SEQ ID NO: 44)

FIG. 4B

AAAGAAGTGGGATACTAAAAAGTGTTCATCTCTTAACCAAGATCACTATGTCCACATTGTGCTTACTCT
CATTCTTTCGATACAATAAATTTGCAGTGCTTTCAGCTGTCGTCTTCTGGAAGAACTTCACATCTTACT
CTATGGTAATTCATCGTCTTTGTGATCATGCTGATTGTTTAAATGTTGCTTGCTTGACTTCAACTGCTTA
ATGTTGTACTTTTGCAGACTAAGAAGCTGTTTCCTGCCGGGCTATTTGCTGTCGTCAGGTGAGAAGTTC
TTTTGTGATCTATAAGAGAGTCTAATGTATCTATCTTTATTGGCTTAATCATGCAACCTTGTGTTCGTGT
CTTTTTCATTGCAGTGCTGCCATGTTGTGTTTCTATTCGTAC--------
CTCTGGAGGAAACCCACCTCCAAAGAAACTTAAACCATCTGCTACTACTAGTCCTTCATACTGAAGAA
ACTTCACATAGGTTAGATTCAAAGATGAAGATCTTCTCTTTTGGTGGCTCTTGTGCGTTGCATTCCTGG
TGTAATTTTATACTTTTGACTTTTGAGGCAACAACTGTG (SEQ ID NO: 45)

FIG. 4C

MEGANUCLEASE TARGET

WILD-TYPE DNA
ATTGCAGTGCTGCCATGTTGTGTTTCTATTCGTACGTGGTGCTCTCTGGAGGAAACCCACCTCCAAAG
AAACTTAAACCATCTGCTACTACTAGTCCTTCATACTGAAGAAA

MUTANT DNA

ATTGCAGTGCTGCCATGTTGTGTTTCTATTCGTAC--------
CTCTGGAGGAAACCCACCTCCAAAGAAACTTAAACCATCTGCTACTACTAGTCCTTCATACTGAAGAA
A

FIG. 4D

CTCTATGGTGGTGGCCTTCTAGCTCTTAGTACGTTGAGCATGAAGATTTGGCGACAGGGAAAGTCTAG
TTTCCCTTATATTCTAGGTCAAGCAGGTAATCTTCATCTACTGGTATCTTACACATGATTAGTGGATATA
TGAAAGAAGTGGGATACTAAAAAGTGTTCATCTCTTAACCAAGATCACTATGTCCACATTGTGCTTACT
CTCATTCTTTCGATACAATAAATTTGCAGTGCTTTCAGCTGTCGTCTTCTGGAAGAACTTCACATCTTA
CTCTATGGTAATTCATCGTCTTTGTGATCATGCTGATTGTTTAAATGTTGCTTGCTTGACTTCAACTGCT
TAATGTTGTACTTTTGCAGACTAAGAAGCTGTTTCCTGCCGGGCTATTTGCTGTCGTCAGGTGAGAAGT
TCTTTTGTGATCTATAAGAGAGTCTAATGTATCTATCTTTATTGGCTTAATCATGCAACCTTGTGTTCGT
GTCTTTTTCATTGCAGTGCTGCCATGTTGTGT-------------------
TCTCTGGAGGAAACCCACCTCCAAAGAAACTTAAACCATCTGCTACTACTAGTCCTTCATACTGAAGA
AACTTCACATAGGTTAGATTCAAAGATGAAGATCTTCTCTTTTGGTGGCTCTTGTGCGTTGCATTCCTG
GTGTAATTTTATACTTTTGACTTTTGAGGCAACAACTGTG (SEQ ID NO: 48)

FIG. 4E

MEGANUCLEASE TARGET

WILD-TYPE DNA
CAGTGCTGCCATGTTGTGTTTCTATTCGTACGTGGTGCTCTCTGGAGGAAACCCACCTCCAAAGAAAC
TTAAACCATCTGCTACTACTAGTCCTTCATACTGAAGAAA

MUTANT DNA

CAGTGCTGCCATGTTGTGT-------------------
TCTCTGGAGGAAACCCACCTCCAAAGAAACTTAAACCATCTGCTACTACTAGTCCTTCATACTGAAGA
AA

FIG. 4F

ATTGCAGTGCTGCTATGTTGTGTTTCTATTCGTACGTGGTGCTCTCTGGAGGAAACCCACCTCCAAAG
AAACTTAAACCATCTGCTACTACTAGCCCTTCATACTGAAGAAACTTCACATAGGTTAGATTCAAAGAT
GGAGATCTTCTCTTTTGGTGGCTCTTGTGCGTTTGATTCCTGGTGTAATTTTATACTTTAGACTTTTGAG
GCAACAACTGTG (SEQ ID NO: 51)

FIG. 4G

ATTGCAGTGCTGCTATGTTGTGTTTCTATTCGT------------------------------------------------------------------------------------------
AGGTTAGATTCAAAGATGGAGATCTTCTCTTTTGGTGGCTCTTGTGCGTTTGATTCCTGGTGTAATTTTATACTTTAGACTTTTGAGGCAACAACTGTG (SEQ ID NO: 51)

FIG. 4H

MEGANUCLEASE TARGET

WILD-TYPE DNA
CTATGTTGTGTTTCTATTCGTACGTGGTGCTCTCTGGAGGAAACCCACCTCCAAAGAAACTTAAACCATCTGCTACTACTAGCCCTTCATACTGAAGAAACTTCACATAGGTTAGATTCAAAG

MUTANT DNA
CTATCTTGTGTTTCTATTCGT-------------------------------------------------------------------------------------------AGGTTAGATTCAAAG

FIG. 4I

CTCTCTCTCGAAACTTAGTTTCAATAGGATATTGCTGAGCTTCCTGTTGAAGTTATTAGAGGACACTTTGTCAGGTGGGCTCGTTATGAGTGGAGGGTTGCTTGGATTTGCGTTTTCACGGAACCTAACAAGTTTAAGTACTGGGGTCCTCTATGGTGGTGGCCTTCTTGCTCTTAGTACATTGAGCTTGAAGATTTGGCGACAGGGAAAATCTAGTTTCCCTTATATTCTTGGTCAAGCAGGTAATCTTTCATTTACTGTCTACATGAACAATTAATCAGTGCTTTCAGCTGTCGTCTTCAGCAGGTATACTTTGTGATACTAAGAGATGCTTACTAATTCTTTCGAAATCCTAAATTTGCAGTGCTTTCAGC (SEQ ID NO: 55)

FIG. 4J

CTCTCTCTCGAAACTTAGTTTCAATAGGATATTGCTGAGCTTCCTGTTGAAGTTATTAGAGGACACTTTGTCAGGTGGGCTCGTTATGAGTGGAGGG---CTTGGATTTGCGTTTTCACGGAACCTAACAAGTTTAAGTACTGGGGTCCTCTATGGTGGTGGCCTTCTTGCTCTTAGTACATTGAGCTTGAAGATTTGGCGACAGGGAAAATCTAGTTTCCCTTATATTCTTGGTCAAGCAGGTAATCTTTCATTTACTGTCTACATGAACAATTAATCAGTGCTTTCAGCTGTCGTCTTCAGCAGGTATACTTTGTGATACTAAGAGATGCTTACTAATTCTTTCGAAATCCTAAATTTGCAGTGCTTTCAGC (SEQ ID NO: 56)

FIG. 4K

MEGANUCLEASE TARGET

WILD-TYPE DNA
TTGTCAGGTGGGCTCGTTATGAGTGGAGGGTTGCTTGGATTTGCGTTTTCACGGAACCTAACAAGTTTAAGTACTGGGGTC

MUTANT DNA
TTGTCAGGTGGGCTCGTTATGAGTGGAGGG---CTTGGATTTGCGTTTTCACGGAACCTAACAAGTTTAAGTACTGGGGTC

FIG. 4L

GTTTCGGCATTCCTTATGGTATACTTGCTCACTCTCTCTCTCGAAACTTAGTTTCAATAGGATATTGCTG
AGCTTCCTGTTGAAGTTATTAGAGGACACTTTGTCAGGTGGGCTCGTTATGAGTGGAGGGTTTGCTTG
GATTTGCGTTTTCACGGAACCTAACAAGTTTAAGTACTGGGGTCCTCTATGG (SEQ ID NO: 59)

FIG. 4M

MEGANUCLEASE TARGET

WILD-TYPE DNA

TTGTCAGGTGGGCTCGTTATGAGTGGAGGGT-
TGCTTGGATTTGCGTTTTCACGGAACCTAACAAGTTTAAGTACTGGGGTCCTCTAT

MUTANT DNA

TTGTCAGGTGGGCTCGTTATGAGTGGAGGGTTTGCTTGGATTTGCGTTTTCACGGAACCTAACAAGTTT
AAGTACTGGGGTCCTCTAT

FIG. 4N

ATGCCCCTTTTCCAGCGGAAAAAGCCGCCGCCGTCTGAGGACCTCCCGGACGACGACGACACCCA
GAACAAATCGAAAAACCGTAAGAAACCGAGCGGGAAGGCGAAGTGGTCGTGCGTGGATTCGTGCTG
CTGGTTCATAGGGTGCGTGTGCCTCACGTGGTGGTTCCTCCTCTTCCTCTACAACGCCATGCCCGCG
AGCTTTCCTCAGTACGTTACCGAGGCGATCACGGGCCCTTTGCCCGACCCGCCCGGCGTGAAGCTG
AAGAAAGAAGGTCTCAGGGCGAAGCATCCCGTTGTGTTCATCCCTGGGATTGTTACGGGTGGACTTG
AGCTTTGGGAAGGGAAACAGTGTGCTGATGGTTTGTTTAGGAAGCGCTTGTGGGGTGGAACTTTCGGT
GAAGTCTACAAAAGGTCAGCTTCCTTACCTTTTTGGGTTTTTATATTAGTTGCAAAAAGCTATCTTCTTT
AGATTCCTAATGTGTGTTTGTGTAAGGGAAGCAATAGCATTTCAATTAAACACGTTTTGATCTCAAAAT
GTCAGCTTCCTTGGAGTTTTGAAGTCAATGCTGTAACCAAATATGTTACTGCACATGCCTTTAGATTAC
GTTCTTAACAAGTTGCTTCCTTTATTGTCATTGGATTTAGCTTACTTGTACGGAGTGTATACTAAAGTAG
TGACTTTTCTTGTTGTGTTACGAGTAGATGTTAAAGATGTGATATAGGATGGTTGCTTTATTCTTCAACT
ATGTCCATGTGCAACTAAAAGTTAGTTTCTTTTGTCTTTTGGATCAAAGTGCTTTTCTCAAATTCTTTCC
GAGAACTGAAAAATTGAGATTTTCAAAAGTTTGGTCTAGTTATTGTCTTGAGTTTCATCCATCTTCATTC
TGTTAGCTAGCTATGAACTCCTCTTTTTGTGTGTTATGATCTGCATCTTTCCTTTTTCGGCCCACGGATC
CTCTTGTTGCTTGGAGATGGGGCAGTGTTACCGTTGAGACTAACAGTGTTCTTGTTCATAGTATCTTTA
CATAATTGGTTATCTCTTTGATTCAGGCCTCTATGCTGGGTGGAACACATGTCACTTGACAACGAAACT
GGTTTAGATCCTGCTGGTATTAGAATCAGAGCTGTATCAGGACTCGTGGCTGCTGACTACTTCGCTCC
TGGCTACTTCGTCTGGGCGGTGCTGATTGCTAACCTTGCACATATTGGATACGAGGAGAAGAACATGT
ACATGGCTGCATATGACTGGAGGCTTTCGTTTCAGAACACAGAGGTTCTTCTCTCATTAAACAAACTC
TCTTATTCTCTCTTTATCTCTTAGGTTCCAACTGTCTTTCATTTGTTGAATCATTAGGTGCGTGACCAGA
CGCTTAGCCGTATGAAAAGCAATATAGAGCTGATGGTTTCCACCAACGGTGGGAAAAAAGCAGTTAT
AGTTCCTCATTCCATGGGGGTATTGTATTTCTTACATTTTATGAAATGGGTTGAGGCACCAGCTCCTAT
GGGCGGCGGTGGTGGGCCTGATTGGTGTGCAAAGCATATCAAAGCGGTGATGAACATTGGTGGACC
GTTTCTTGGTGTTCCAAAAGCTGTCGCAGGGCTTTTCTCCGCTGAGGCAAAGGATGTTGCAGTTGCCA
GGTATTGAATTAGCTGACTGTGGTTTTAGCCAATAAAATCTCTTATTCTGCTTTTGAAACTATGCAGAG
CGATTGCGCCAGGGTTCTTAGACACTGATATATTCAGACTCCAGACGCTGCAACACGTGATGAGAAT
GACACGCACATGGGACTCAACGATGTCTATGATACCTAAGGGAGGTGACACAATATGGGGCGGTCTT
GATTGGTCGCCGGAGAAAGGCCACATATGTTCCGGTAAAAAGAAAAGTAGCAACAAGACTCGCGGA
GAAGCTGGTGAAAACTCAGTTTCCAAGACAAAGCCTGTTAACTACGGAAGAATCATATCGTTCGGGA
AAGATGTGGCTGAGGCTGCGCCGTCTGAGATTGAAAACATTGATTTTCGAGTAAGGACATATGAACTG
TTAATACTTTTTTTGTGATTAGATGACTAATAGGTACGTTTTTACTTGGTGAAGGGTGCGGTGAAAGGTC
AGAGTATCCCAAACAACACATGCCGTGACGTGTGGACGGAGTATCATGATATGGGAATCGGAGGGAT
CAAAGCTATTGCTGAGTATAAGGTCTACACTGCTGACGCGGTTATAGATTTGCTACATTATGTTGCTCC
TAAGATGATGGCGCGTGGTGCTGCTCATTTCTCCTATGGGATTGCTGATGATTTAGATGACCCTAAGT
ATGAACATCACAGACACTGGTCCAATCCATTGGAAACAAAGTAAGTGGTTTTGTTTTTGTACCAACTCT
ATGCTTTGTCCTGATGCATTATTAGTCTTTTAGTTTTTTCCCCTTGTTGAATATGCTTATCAACTCAAAG
CTAAGAGCATCTCCAATGGTATTCAATTTTTCATTTTAAAATAGAGTTTAGAGTAAAAATGCTCAAATAG
TACTCTATTTTTCATTCTATAGTAGAGTAAAAAATGGATTTAGTCTATAAATAGAGTAGTTTATTTTTTTT
CCACCACTCTATTCTTCACTATAAAATAGAATACCATAGGAGTATAACTCAATTCCATTATAGACTTAT
TCTATTTTGAGAAAAAAAAAGAGTGAACGATTAGAGATAGTCTAGTTTGAGTCTTTCCGAAAAGGCTTT
ACTTAGTTATATTTAGGTTTTAAAGTTGATACATGTGATGCTTGCTTATAAAACCAGCTCTAGGATGGCT
TTGACATGACAAATAAACCAACTAATTCGAAATCTATTTGACTGAAAACCCTTAGTACCACCTTCTAGT
TTTAGAGTTTATCTATCCCTTTGAGGATCATTTCCCTCTGTCTTATCCTTAGAAACCACATTTGGTTTGT
TCTGCCGTTTCAGGTTACCCAATGCCCCTGAAATGGAGATCTACTCACTGTATGGAGTTGGGATACCA
ACAGAACGATCATACATCTACAAGCTCAATCAGTCTCCAGACAGCTGCATCCCCTTTCATATCTTCAC
TTCTGCTCACGAGGAGGACAAAGAAAGCTGTCTGAAAGCAGGAGTTTACAACGTGGATGGAGATGAA
ACAGTACCGGTCCTAAGCGCAGGGTTCATGTGTGCTAAAGCGTGGCGCGGCAAGACGAGATTCAAC
CCTTCTGGAATCAAGACTTACATTAGAGAATACAACCACTCTCCACCAGCTAACCTGCTAGAAGGGC
GAGGGACGCAGAGTGGGGCTCATGTTGATATCATGGGAAACTTTGCGTTGATCGAGGATATCATGAG
GGTTGCCACGGGAGGTAACGGGTCCGACCTAGGACATGACCAGGTCCACTCTGGTATATTTGAATGG
TCTGAGCGTATTGACTTGAAGCTGTGA (SEQ ID NO: 62)

FIG. 5A

TGCGGTGAAAGGTCAGAGTATCCCAAACAACACATGCCGTGACGTGTGGACGGAGTACCATGATATG
GGAATTGGAGGGATCAAAGCTATTGCTGAGTATAAGGTCTACACTGCTGACGCGGTTATAGATTTATT
ACATTATGTTGCTCCTAAGATGATGGCGCGTGGCGCCGCTCATTTCTCCTATGGGATTGCTGATGATT
TGGATGACCCCAAGTACGAACATCACAGGCAC (SEQ ID NO: 63)

FIG. 5B

TGCGGTGAAAGGTCAGAGTATCCCAAACAACACATGCCGTGACGTGTGGACGGAGTACCATGATATG
GGAATTGGAGGGATCAAAGCTATTGCTGAGTA------
TCTACACTGCTGACGCGGTTATAGATTTATTACATTATGTTGCTCCTAAGATGATGGCGCGTGGCGCC
GCTCATTTCTCCTATGGGATTGCTGATGATTTGGATGACCCCAAGTACGAACATCACAGGCAC (SEQ
ID NO: 64)

FIG. 5C

MEGANUCLEASE TARGET

WILD-TYPE DNA
AACACATGCCGTGACGTGTGGACGGAGTACCATGATATGGGAATTGGAGGGATCAAAGCTATTGCTG
AGTATAAGGTCTACACTGCTGACGCGGTT

MUTANT DNA
AACACATGCCGTGACGTGTGGACGGAGTACCATGATATGGGAATTGGAGGGATCAAAGCTATTGCTG
AGTA------TCTACACTGCTGACGCGGTT

FIG. 5D

GAGAAGCTGGTGAAAACTCAGTTTCCAAGACAAAGCCTGTTAACTACGGAAGAATCATATCGTTCGG
GAAAGATGTGGCTGAGGCTGCGCCGTCTGAGATTGAAAACATTGATTTTCGAGTAAGGACATATGAAC
TGTTAATACTTTTTTTGTGATTAGATGACTAATAGGTACGTTTTTACTTGGTGAAGGGTGCGGTGAAAGG
TCAGAGTATCCCAAACAACACATGCCGTGACGTGTGGACGGAGTATCATGATATGGGAATCGGAGGG
ATCAAAGCTATTGCTGAGTATAAGGTCTACACTGCTGACGCGGTTATAGATTTGCTACATTATGTTGCT
CCTAAGATGATGGCGCGTGGTGCTGCTCATTTCTCCTATGGG (SEQ ID NO: 67)

FIG. 5E

GAGAAGCTGGTGAAAACTCAGTTTCCAAGACAAAGCCTGTTAACTACGGAAGAATCATATCGTTCGG
GAAAGATGTGGCTGAGGCTGCGCCGTCTGAGATTGAAAACATTGATTTTCGAGTAAGGACATATGAAC
TGTTAATACTTTTTTTGTGATTAGATGACTAATAGGTACGTTTTTACTTGGTGAAGGGTGCGGTGAAAGG
TCA---------------------------------------------------------------------------------------------------------
GAGTATAAGGTCTACACTGCTGACGCGGTTATAGATTTGCTACATTATGTTGCTCCTAAGATGATGGC
GCGTGGTGCTGCTCATTTCTCCTATGGG (SEQ ID NO: 68)

FIG. 5F

MEGANUCLEASE TARGET

WILD-TYPE DNA
AAAGGTCAGAGTATCCCAAACAACACATGCCGTGACGTGTGGACGGAGTATCATGATATGGGAATCG
GAGGGATCAAAGCTATTGCTGAGTATAAGGTCTACACTGCTGAC
MUTANT DNA
AAAGGTCA--------------------------------------------------------------------------------------------
GAGTATAAGGTCTACACTGCTGAC

FIG. 5G

CTCCAGACGTTGCAGCATGTAATGAGAATGACACGAACATGGGACTCAACGATGTCTATGATACCTA
AAGGAGGTGACACGATATGGGGTGGTCTTGACTGGTCTCCGGAGCAAGGCTACACTTGCTCTGGTAA
AAAACAAAAGAGCAACGAGACTCGCGGTGAAGAAGGTGAGAGTTTAGTTACCAAGACGAAGCCTGT
CAACTACGGAAGAATCATATCGTTTGGGAAAGACGTGGCAGAGGCTCATCCATCTGAGATTAAAAAC
ATTGATTTTCGAGTAAGGAGCACTAATCATATTAAACAAACCTCTTGTAGCTTTTGTGATTTAGATGATT
AGTAATCTGTATATGTGTTACTTGGTGAAGGGTGCTGTGAAAGGTCAGAGTATCCCAAACAACACGTG
CCGTGACGTGTGGACGGAGTACCATGATATGGGAATTGGAGGGATCAAAGCTATTGCTGAGTATAAG
GTCTACACTGCTGATACAGTCATTGATTTGCTACATTATGTTGCTCCTAAGATGATGGCGCGTGGTTCT
GCTCATTTCTCTTATGGGATTGCGGATGATTTAGATGATCCTAAGTATGATCATCCCAGACACTGGTCT
AATC (SEQ ID NO: 71)

FIG. 5H

CTCCAGACGTTGCAGCATGTAATGAGAATGACACGAACATGGGACTCAACGATGTCTATGATACCTA
AAGGAGGTGACACGATATGGGGTGGTCTTGACTGGTCTCCGGAGCAAGGCTACACTTGCTCTGGTAA
AAAACAAAAGAGCAACGAGACTCGCGGTGAAGAAGGTGAGAGTTTAGTTACCAAGACGAAGCCTGT
CAACTACGGAAGAATCATATCGTTTGGGAAAGACGTGGCAGAGGCTCATCCATCTGAGATTAAAAAC
ATTGATTTTCGAGTAAGGAGCACTAATCATATTAAACAAACCTCTTGTAGCTTTTGTGATTTAGATGATT
AGTAATCTGTATATGTGTTACTTGGTGAAGGGTGCTGTGAAAGGTCAGAGTATCCCAAACAACACGTG
CCGTGACGTGTGGACGGAGTACCATGATATGGGAATTGGAGGGATCAAAGCTATTGCTGAGTA------
----------
TGATACAGTCATTGATTTGCTACATTATGTTGCTCCTAAGATGATGGCGCGTGGTTCTGCTCATTTCTC
TTATGGGATTGCGGATGATTTAGATGATCCTAAGTATGATCATCCCAGACACTGGTCTAATC (SEQ ID
NO: 72)

FIG. 5I

MEGANUCLEASE TARGET

WILD-TYPE DNA
GTACCATGATATGGGAATTGGAGGGATCAAAGCTATTGCTGAGTATAAGGTCTACACTGCTGATACAG
TCATTGATTTGCTACATTATGTTGCTC
MUTANT DNA
GTACCATGATATGGGAATTGGAGGGATCAAAGCTATTGCTGAGTA----------------
TGATACAGTCATTGATTTGCTACATTATGTTGCTC

FIG. 5J

TCAACGATGTCTATGATACCTAAAGGAGGTGACACGATATGGGGTGGTCTTGACTGGTCTCCGGAGC
AAGGCTACACTTGCTCTGGTAAAAAACAAAAGAGCAACGAGACTCGCGGTGAAGAAGGTGAGAGTTT
AGTTACCAAGACGAAGCCTGTCAACTACGGAAGAATCATATCGTTTGGGAAAGACGTGGCAGAGGCT
CATCCATCTGAGATTAAAAACATTGATTTTCGAGTAAGGAGCACTAATCATATTAAACAAACCTCTTGT
AGCTTTTGTGATTTAGATGATTAGTAATCTGTATATGTGTTACTTGGTGAAGGGTGCTGTGAAAGGTCA
GAGTATCCCAAACAACACGTGCCGTGACGTGTGGACGGAGTACCATGATATGGGAATTGGAGGGATC
AAAGCTAT----------------------
TGCTGATACAGTCATTGATTTGCTACATTATGTTGCTCCTAAGATGATGGCGCGTGGTTCTGCTCATTT
CTCTTATGGGATTGCGGATGATTTAGATGATCCTAAGTATGATCATCCCAGACACTGGTCTAA (SEQ ID NO: 75)

FIG. 5K

MEGANUCLEASE TARGET

WILD-TYPE DNA

GTACCATGATATGGGAATTGGAGGGATCAAAGCTATTGCTGAGTATAAGGTCTACACTGCTGATACAG
TCATTGATTTGCTACATTATGTTGCTCCTAAGAT

MUTANT DNA

GTACCATGATATGGGAATTGGAGGGATCAAAGCTAT----------------------
TGCTGATACAGTCATTGATTTGCTACATTATGTTGCTCCTAAGAT

FIG. 5L

CTCCAGACGTTGCAGCATGTAATGAGAATGACACGCACATGGGACTCAACAATGTCTATGATACCTA
AAGGAGGTGACACGATATGGGGTGGTCTTGATTGGTCTCCGGAGCAAGGGTACACTTGCTCTGGTAA
AAAGCAAAAGAACAACGAGACTCGCGGTGAAGAAAGTGAGAGTTTAGTTACCAAGACGAAGCCTGTC
AACTACGGAAGAATCATATCGTTTGGGAAAGACGTGGCAGAGGCTCATCTATCTGAGATTAAAAACAT
TGATTTTCGAGTAAGGACATATAAACCTCTAGTAGCTTTGGTGGTTAGACGATTAATAATCTTTGTATAT
GTTACTTTGTTGAAGGGTGCTGTGAAAGGTCAGAGTATCCCAAACAACACGTGCCGTGACGTGTGGA
CAGAGTACCATGATATGGGAACTGGAGGGATCAAAGCTATTGCTGAGTATAAGGTCTACACTGCTGAT
GCAGTCATTGATTTGCTACATTATGTTGCTCCTAAGATGATGGCGCGTGGTTCCTCTCATTTCTCTTAC
GGGATTG (SEQ ID NO: 78)

FIG. 5M

CTCCAGACGTTGCAGCATGTAATGAGAATGACACGCACATGGGACTCAACAATGTCTATGATACCTA
AAGGAGGTGACACGATATGGGGTGGTCTTGATTGGTCTCCGGAGCAAGGGTACACTTGCTCTGGTAA
AAAGCAAAAGAACAACGAGACTCGCGGTGAAGAAAGTGAGAGTTTAGTTACCAAGACGAAGCCTGTC
AACTACGGAAGAATCATATCGTTTGGGAAAGACGTGGCAGAGGCTCATCTATCTGAGATTAAAAACAT
TGATTTTCGAGTAAGGACATATAAACCTCTAGTAGCTTTGGTGGTTAGACGATTAATAATCTTTGTATAT
GTTACTTTGTTGAAGGGTGCTGTGAAAGGTCAGAGTATCCCAAACAACACGTGCCGTGACGTGTGGA
CAGAGTACCATGATATGGGAACTGGAGGGATCAAAGCTATTGCT----------
GGTCTACACTGCTGATGCAGTCATTGATTTGCTACATTATGTTGCTCCTAAGATGATGGCGCGTGGTTC
CTCTCATTTCTCTTACGGGATTG (SEQ ID NO: 79)

FIG. 5N

MEGANUCLEASE TARGET

WILD-TYPE DNA
GACGTGTGGACAGAGTACCATGATATGGGAACTGGAGGGATCAAAGCTATTGCTGAGTATAAGGTCT
ACACTGCTGATGCAGTCATTGATTTGCTACATTATGT

MUTANT DNA

GACGTGTGGACAGAGTACCATGATATGGGAACTGGAGGGATCAAAGCTATTGCT--------
GGTCTACACTGCTGATGCAGTCATTGATTTGCTACATTATGT

FIG. 5O

CTCCAGACGTTGCAGCATGTAATGAGAATGACACGCACATGGGACTCAACAATGTCTATGATACCTA
AAGGAGGTGACACGATATGGGGTGGTCTTGATTGGTCTCCGGAGCAAGGGTACACTTGCTCTGGTAA
AAAGCAAAAGAACAACGAGACTCGCGGTGAAGAAAGTGAGAGTTTAGTTACCAAGACGAAGCCTGTC
AACTACGGAAGAATCATATCGTTTGGGAAAGACGTGGCAGAGGCTCATCTATCTGAGATTAAAAACAT
TGATTTTCGA[DELETION]CATTATGTTGCTCCTAAGATGATGGCGCGTGGTTCCTCTCATTTCTCTTAC
GGGATTG (SEQ ID NO: 82)

FIG. 5P

MEGANUCLEASE TARGET

WILD-TYPE DNA
GACGTGTGGACAGAGTACCATGATATGGGAACTGGAGGGATCAAAGCTATTGCTGAGTATAAGGTCT
ACACTGCTGATGCAGTCATTGATTTGCTACATTATGTTGCTCCTAAGAT

MUTANT DNA

------------------------------------------------------------------------------------------------------------------------

CATTATGTTGCTCCTAAGAT

FIG. 5Q

ATGGCGGCAACAGCAGCAGCTTCGAGCTTGCAAATGGCTACAACAAGGCCAAGCATTTCTGCAGCC
TCTACCAAAACAAGGACCTACGTTGTCGGTGCCAATCCCAGGAACGCATCGTGGGACAAAATTGCTT
GCACTCCCCATCTATCGAACCTCGGGTGTTTGAGAAACGACAGTGCTCTTCCAGCTTCTAAAAAGAG
TTTTTCCTTTTCGACAAAGGCCATGTCTGAATCCAGCGAAAGCAAGGCTTCTTCTGGACTTCCCATTG
ATTTGAGAGGTTCCTTTCTAGTCATATCTTAATCATCATTACTAAGATTGATTGCTATTAGAAGACAATG
AGCTGTTTGAATTAAATCAACTGTGTTAAATGGTTTCTAGGGAAAAGAGCCTTTATTGCTGGTATAGCT
GATGATAATGGATATGGTTGGGCCATAGCCAAATCTCTTGCTGCTGCTGGTGCTGAAATTTTGGTTGG
GACTTGGGTTCCTGTAAGTTTCCTTTTTTTTTTTTTTTTAATTAACTCTATTGAGCAGTTTAAGTTTCCTCA
TGTACTGACGACCTTTGAATGGTGCTCTACTAGGCACTTAACATTTTTGAGACGAGCTTGAGGCGTGG
AAAATTCGACCAGTCGCGCGTGTAAGGACTTACAACAAAACTGATCAACTCTTTGTTTCTTTTATTTTC
CACATCATCTAATATCTAAAATTCAGGTTGCCAGACGGATCATTGATGGAGATTAAAAAGGTTTATCCT
TTGGATGCTGTCTTTGACAATCCTGAAGATGTCCCTGAAGATGTACGTGAGAGAATACATCTTTCACAT
CATACTAAAACCCTTAATATCCATATTAGTTATGATACATTCTTTTTTCTTACAGGTGAAAGCGAATAAG
CGATATGCTGGATCGTCAAACTGGACTGTACAGGAAGCTGCAGAATGTGTGAGACAAGATTTTGGAA
GCATTGACATTCTTGTCCACTCACTTGCAAATGGACCAGAGGCAAGAACTCTATCTGAAACTGTTTTA
CAAGAACTGTATTCTGTTTTGCCTAATGGGAAATCTTCTGATATTTTTAGGTTAGCAAACCTCTTCTTGA
GACATCGAGGAAAGGCTATCTTGCTGCTATCTCTGCTTCCAGCTACTCCTTTGTTTCCCTCCTCAGCC
ATTTTCTCCCAATTATGAACCCAGGCATGTCACAAAACTTTGTATTATTCCTCTTCTTCTTTATAATTATT
TGTTTTTTTTTTTTTTTTAAATTTTATTTGTTTCTCTATGATATGATATAGGAGGTGCTTCTATCTCTCTTAC
TTACATTGCCTCTGAAAGGATCATTCCCGGGTAAGGGTCATACTATAGCTTCACAACATTGTTTTGTTT
CTCAATAGATGATTACAAGTGTATCTTTTAATTTCTGTTGTTAGGTATGGTGGAGGTATGAGTTCTGCCA
AGGCCGCACTAGAGAGTGATACACGTGTGCTTGCATTTGAAGCTGGGAGGAAACAAAACATTAGGGT
CAACACTATCTCTGCAGGCCCTTTGGGAAGCCGAGCAGCTAAAGCAATTGGGTTCATAGACACAATG
ATCGAGTATTCATACAATAACGCGCCTATTCAGAAAACACTGACTGCAGGTTCATTCATACATACAAG
CATTTCTTTTTGTTGGCTTTCAGTTTTCTTTGGAAATTTTATTAAAAAATGAGGAATATGATGATGCAGAT
GAAGTTGGGAATGCGGCAGCCTTCTTGGTATCTCCATTGGCATCTGCCATAACTGGTGCAACCATCTA
TGTGGACAATGGCTTGAATTCAATGGGTGTTGCTCTTGACAGCCCCGTTTTCAAAGACCTCAACAAAT
AA (SEQ ID NO: 85)

FIG. 6A

GGTTTATCCTTTGGATGCTGTCTTTGACACTCCTGATGATGTCCCTGAAGATGTAAGGGAGATTTACAT
CTTTCACATCATATTAAAACCCTTAATATCCAAATTAGTTATGATAACATTTTATTTTTCCAGGTGAAAG
CGAATAAGCGATATGCTGGATCATCAAACTGGACTGTACAGGAAGCTGCAGAATGTGTGAGACAAGA
TTTTGGAAGCATTGACATTCTTGTCCACTCACTTGCAAATGGACCAGAGGCAAGAACTCTATCTGAAA
CTGTTTTACAAGAACTTTATTCTGTTTTGCCTGATGGGAGATCTTCTGAATATTTTTAGGTTAGCAAACC
TCTTCTGGAGACAACGAGGAAAGGCTATCTTGCTGCTATTTCTGCTTCCAGCTACTCCTTTG (SEQ ID
NO: 86)

FIG. 6B

GGTTTATCCTTTGGATGCTGTCTTTGACACTCCTGATGATGTCCCTGAAGATGTAAGGGAGATTTACAT
CTTTCACATCATATTAAAACCCTTAATATCCAAATTAGTTATGATAACATTTTATTTTTCCAGGTGAAAG
CGAATAAGCGATATGCTGGATCATCAAACTGGACTGTACAGGAAGCTGCAGAATGTGTGAGACAAGA
TTTTGGAAGCATTGACATTCTTGTCCACTCACTTGC------
ACCAGAGGCAAGAACTCTATCTGAAACTGTTTTACAAGAACTTTATTCTGTTTTGCCTGATGGGAGATC
TTCTGAATATTTTTAGGTTAGCAAACCTCTTCTGGAGACAACGAGGAAAGGCTATCTTGCTGCTATTTC
TGCTTCCAGCTACTCCTTTG (SEQ ID NO: 87)

FIG. 6C

MEGANUCLEASE TARGET

WILD-TYPE DNA
TGAGACAAGATTTTGGAAGCATTGACATTCTTGTCCACTCACTTGCAAATGGACCAGAGGCAAGAACT
CTATCTGAAACTGTTTTACAAGAACTTTATTCTGTTTTGCC

MUTANT DNA
TGAGACAAGATTTTGGAAGCATTGACATTCTTGTCCACTCACTTGC------
ACCAGAGGCAAGAACTCTATCTGAAACTGTTTTACAAGAACTTTATTCTGTTTTGCC

FIG. 6D

TCTCAACTGTATGATACATTTTTCAGGTGAAAGCGAATAAGCGATATGCTGGATCATCAAACTGGACA
GTACAGGTATAGTCTTATAGATGAAAGAGATGTTTTATATTTTGAAATGTGTGGTAACATCTAAAGCTAG
AGAAATGTGTGTGTTTTTGCTTGATGCTTGCGACTTTCTTAACTCATCTTTTTTTTTCTCTTTGGTATTGA
TTAAATCAGGAAGCTGCTGAATGTGTTAAAAAAGATTTTGGAACCATTGACATTCTTGTCCACTCACTT
GCA-AATGGGCCCGAGGTAGAGAACTCATAGTGTTCTTATCTTAATACTGT (SEQ ID NO: 90)

FIG. 6E

TCTCAACTGTATGATACATTTTTCAGGTGAAAGCGAATAAGCGATATGCTGGATCATCAAACTGGACA
GTACAGGTATAGTCTTATAGATGAAAGAGATGTTTTATATTTTGAAATGTGTGGTAACATCTAAAGCTAG
AGAAATGTGTGTGTTTTTGCTTGATGCTTGCGACTTTCTTAACTCATCTTTTTTTTTCTCTTTGGTATTGA
TTAAATCAGGAAGCTGCTGAATGTGTTAAAAAAGATTTTGGAACCATTGACATTCTTGTCCACTCACTT
GCAAAATGGGCCCGAGGTAGAGAACTCATAGTGTTCTTATCTTAATACTGT (SEQ ID NO: 91)

FIG. 6F

MEGANUCLEASE TARGET

WILD-TYPE DNA
GCTGCTGAATGTGTTAAAAAAGATTTTGGAACCATTGACATTCTTGTCCACTCACTTGCA-
AATGGGCCCGAGGTAGAGAACTCATAGTGTTCTTATCTTAATACTGT

MUTANT DNA
GCTGCTGAATGTGTTAAAAAAGATTTTGGAACCATTGACATTCTTGTCCACTCACTTGCAAAATGGGC
CCGAGGTAGAGAACTCATAGTGTTCTTATCTTAATACTGT

FIG. 6G

CATTTTTGAGACGAGCTTGAGGCGTGGAAAATTCGACCAGTCGCGCGTGTAAGGACTTACAACAAAA
CTGATCAACTCTTTGTTTCTTTTATTTTCCACATCATCTAATATCTAAAATTCAGGTTGCCAGACGGATC
ATTGATGGAGATTAAAAAGGTTTATCCTTTGGATGCTGTCTTTGACAATCCTGAAGATGTCCCTGAAGA
TGTACGTGAGAGAATACATCTTTCACATCATACTAAAACCCTTAATATCCATATTAGTTATGATACATTC
TTTTTTCTTACAGGTGAAAGCGAATAAGCGATATGCTGGATCGTCAAACTGGACTGTACAGGAAGCTG
CAGAATGTGTGAGACAAGATTTTGGAAGCATTGACATTCTTGTCCACTCACTTGCAAATGGACCAGAG
GCAAGAACTCTATCTGAAACTGTTTTACAAGAACTGTATTCTGTTTTGCCTAATGGGAAATCTTCTGAT
ATTTTTAGGTTAGCAAACCTCTTCTTGAGACATCGAGGAAAGGCTATCTTGCTGCTATCTCTGCTTCCA
GCTACTCCTTTGTTTCCCTCCTCAGCCATTTTCTCCCAATTATGAACCCAGGCATGTCACAAAACTTTG
TATTATTCCTCTTCTTCTTTATAATTATTTG (SEQ ID NO: 94)

FIG. 6H

CATTTTTGAGACGAGCTTGAGGCGTGGAAAATTCGACCAGTCGCGCGTGTAAGGACTTACA[DELETIO
N]ACAAGAACTGTATTCTGTTTTGCCTAATGGGAAATCTTCTGATATTTTTAGGTTAGCAAACCTCTTCT
TGAGACATCGAGGAAAGGCTATCTTGCTGCTATCTCTGCTTCCAGCTACTCCTTTGTTTCCCTCCTCA
GCCATTTTCTCCCAATTATGAACCCAGGCATGTCACAAAACTTTGTATTATTCCTCTTCTTCTTTATAAT
TATTTG (SEQ ID NO: 95)

FIG. 6I

MEGANUCLEASE TARGET

WILD-TYPE DNA
GTGTGAGACAAGATTTTGGAAGCATTGACATTCTTGTCCACTCACTTGCAAATGGACCAGAGGCAAGA
ACTCTATCTGAAACTGTTTT ACAAGAACTGTATTCTGTTT

MUTANT DNA

------------------------------------------------------------------------------------------

ACAAGAACTGTATTCTGTTT

FIG. 6J

CATTAAGAGAAACCCGTCTGCCTCTTTTCATAACCTCATAAATATTCCAACCATTCCATGTCTCGCTTC
TCTCATCTGTTGTTCTCTGTAGGTTTTAAGTTCTTTTTGTCCTCTTCTATAATATGAACACCCTTCTTAAT
TGTTCCTTATTGTCTACCTCTCTTTATTACATTCGACAGAAAGGAACGAGTGAAAAGAGTTTGGATCTT
TAAGCTTTTTGATCATGTGGGTTTGACAAAAGAGTTTCTTACAGAGATCTTTGGCATTCTGTCCACCTC
CCCTACCTATGTATATGTGTATTATCTACGTTGTGTTTTGTGAGGGGGAGGTGGGCATACTGCCAACA
GAGATCTGTTAGGGTTTCTTTGTAAAACCCCTCATGATTTGTTGTATTCAAGATAAGGCATTGGCTCGT
GTTGATCAAGATGACTTGATGAACACTAAGATCTAGGTTTGAGGAAAAATGGTATTATCTCGGATATAC
TCAACCTTAATTATTATGTATGATCACTACATCTTAGTATTTTAT (SEQ ID NO: 98)

FIG. 7A

GTGTAAAAATGACTTCATCGAACAAAAGAAGTGACGATCACATATAATAAGGTTAAGTGAATTAGAGA
TAATACCATTTTTCTTCAAACTCTGGTCTTAGTGATCTTGATTACCATGATGAGCCAATGTACTATCTTG
AATACATCAAATCATGAGGGGTTTTACAAAGAAACCCTAACAGATCTCTATTGGCAGTATGCCCACCT
CCTCTCACAAAACACAACGTGGTTACGAACACTTATACACAAATATATTCAGAAAGGAGGTGGACAG
AATGCCAAAGAACTCTGTAAGAAATTCTTTTGTCAAACCCACATGATCAAAAAGGTTACCGATCCAAA
CTTTACCTTTTATATACGGCAAGGAGCAAAAAGTGTTTCA (SEQ ID NO: 99)

FIG. 7B

GTGTAAAAATGACTTCATCGAACAAAAGAAGTGACGATCACATATAATAAGGTTAAGTGAATTAGAGA
TAATACCATTTTTCTTCAAACTCTGGTCTTAGTGATCTTGATTACCATGATGAGCCAATGTACTATCTTG
AATACATCAAATCATGAGGGGTTTTACAAAGAAACCCTAACAGATCTCTATTGGCAGTATGCCCACCT
CCTCTCACAAAACACAACGTGGTTACGAACACTTATACACAAATATATTCAGAAAGGAGGTGGACAG
AATGCCAAA---------------------------------------------
GAGCAAAAAAGTTACCGATCCAAACTTTACCTTTTATATACGGCAAGGAGCAAAAAGTGTTTCA (SEQ ID NO: 100)

FIG. 7C

MEGANUCLEASE TARGET

WILD-TYPE DNA
ATTCAGAAAGGAGGTGGACAGAATGCCAAAGAACTCTGTAAGAAATTCTTTTGTCAAACCCACATGAT
CAAAAAGGTTACCGATCCAAACTTTACCTTTTA

MUTANT DNA
ATTCAGAAAGGAGGTGGACAGAATGCCAAA ---------------------------------------------
GAGCAAAAAAGTTACCGATCCAAACTTTACCTTTTA

FIG. 7D

CATTCGACAGAAAGGAACGAGTGAAAAGAGTTTGGATCTTTAAGCTTTTTGATCATGTGGGTTTGACAA
AAGAGTTTCTTACAGAGATCTTTGGCATTCTGTCCACCTCCCCTACCTATGTATATGTGTATTATCTAC
GTTGTGTTTTGTGAGGGGGAGGTGGGCATACTGCCAACAGAGATCTGTTAGGGTTTCTTTGTAAAACC
CCTCATGATTTGTTGTATTCAAGATAAGGCATTGGCTCGTGTTGATCAAGATGACTTGATG (SEQ ID NO: 103)

FIG. 7E

CATTCGACAGAAAGGAACGAGTGAAAAGAGTTTGGATCTTTAAGCTTTTTGATCATGTGGGTTTGACAA
AAGAGTTTCTTACAGAGATCTTTGGCATTCTGTCCACCTCCCCTACCTATGTATATGTGTATTATCTAC
GTTGTGTTTTGTGAGGGGGAGGTGGGCATACTGCCAACAGAGATCTGTTAGGGTTTCTTTGTAA-------
-----------GGCATTCAAGATAAGGCATTGGCTCGTGTTGATCAAGATGACTTGATG (SEQ ID NO: 104)

FIG. 7F

MEGANUCLEASE TARGET

WILD-TYPE DNA
AGGGGGAGGTGGGCATACTGCCAACAGAGATCTGTTAGGGTTTCTTTGTAAAACCCCTCATGATTTGT
TGTATTCAAGATAAGGCATTGGCTCGTGTTGATC

MUTANT DNA
AGGGGGAGGTGGGCATACTGCCAACAGAGATCTGTTAGGGTTTCTTTGTAA-----------------
GGCATTCAAGATAAGGCATTGGCTCGTGTTGATC

FIG. 7G

ATGGCTGCCCCCAACTCCATTTTCACCACCGCTCCGTCGAGAAATCTCGCACCTATCTCTCTTCACC
AGTCATTATCTTCACCGTTGAGTCTCCGGATCACTAAATCGAACTCCGTCGCGTTTCGTCCCAAACCC
CGATCCAGCTCGCTCGTCTTCTGCTCCACCGATGAATCAAAGATCTCCGCAGAGAAAGAGATCCCAA
TTGAACTTAGTAAGTAAAACTTTCTCTAATGGCATTATAACTTAAAAATTCGAAAATTTCAATTAAAATA
AATAAATAATTTTTTGCAGGGTACGAGGCTTATCCGACAGTGATGGACATTAACCAGATACGAGAGAT
TTTGCCTCACAGGTGAATAAATTTCTCTTACACGCTGTTTCTCTAGCTGAAGTTGTATTGTTCTGATTCC
TTGTCTTAATTTTTTTTTTATAAAAAAAAAATCGATTTTGGACTGTTGTGTAGGTTCCCGTTTCTGTTAGT
GGATAGAGTGATAGAGTACACAGCTGGTGAATCTGCGGTAGCTATCAAGAACGTTACCATTAATGACA
ATTTCTTTCCTGGGCATTTCCCTGAGAGGCCCATTATGCCTGGTGTCCTCATGGTTGAGGTAATCATCT
CATTGCATGCTTCTCTCTTTTTGCAATACATTCATAGTTCAAGAGAAGTTATTTGATCTCCAGAGTTAGA
AGAATACTTATTAGTGTATATATACTAGCCGGAGTTAGTTGAATTGTTACTTATCATAGCTATATATGAA
CATTTGCTTTATAAGTAAAACCAGTAGCAGTCTGTTCCAGATGTATGTGATATGAAATGAGTAGGGGAC
TCATTGTGTGTTAATAAGAGCTATATATAGATTGCCTCATCAATTAGTTTTTTTTTTTTTTGGTTTCCACA
GGCCATGGCTCAGGTGGGAGGTATAGTGATGCTAAATCCAGAAGTGGGCGGATCTAAAAGCAACTTC
TTCTTTGCTGGAGTCGACAAAGTGAGATTCAGAAAGCCTGTGATTGCAGGTGACACTCTGGTGATGAG
GATGACGCTTGTGAAGCTGCAGAAGCGGTTTGGGATAGCCAAAATGGAAGGGAAAGCATACGTAGG
GAACACTTTGGTATGCGAAGGAGAGTTCTTGATGGCTATGGGGAAAGAAGAGGAGTGA (SEQ ID NO: 107)

FIG. 8A

GGAGAAAGAGATCCCAATAGAGCTCAGTAAGCTTACCATCTCATAACAATCTGATTACAAATCAAAAA
ATTTAATTAAAAAATAAATAAATAAAATTGGGCAGGGTACGAGGCTTTTCCGACAGTGATGGACATAA
CCAGATACGTGAGATATTGCCTCACAGGTGAATAATTTTATTACACACTGTTTCTCCAAACTGAAGTTG
TTTTGTTCTGATTCGATGTCTGGACTGGTTGTGTTATGTAGGTTCCCGTTTCTGTTAGTGGATAGAGTGA
TAGAGTACACACCTGGTGTATCTGCTGTAGCTATCAAAAACGTTACCATTAATGATAATTTCTTTCCTG
GGCATTTTCCTGAGAGGCCCATTATGCCTGGAGTCCTCATGGTTGAGGTAAAATCTCATTGCAAGCTT
CACTCCTTTTTTTGCTACTTGATCTTTAGAGATCTTGGCTTTGCTTAGGCTGGGTTAATAGAGAGTAAGA
TTAGCTTGTTTTGAAGGATACCCCTGGATCATACCTTTATATCAAGAGTTGCTCTATTACGACATAACT
AAAGCCAGTAGCATCTATTCCAGCCAAAATACATGATGAGTCTCCTAATGATTTCATGCTACATAGATT
TTCAGACATCTTGTACTTAAAAATTATTCAAAGCATTAAAATATACTTTCTCCGTTTCATAAAAAAAATGC
ATGTTTTAGA (SEQ ID NO: 108)

FIG. 8B

GGAGAAAGAGATCCCAATAGAGCTCAGTAAGCTTACCATCTCATAACAATCTGATTACAAATCAAAAA
ATTTAATTAAAAAATAAATAAATAAAATTGGGCAGGGTACGAGGCTTTTCCGACAGTGATGGACATAA
CCAGATACGTGAGATATTGCCTCACAGGTGAATAATTTTATTACACACTGTTTCTCCAAACTGAAGTTG
TTTTGTTCTGATTCGATGTCTGGACTGGTTGTGTTATGTAGGTTCCCGTTTCTGTTAGTGGATAGAGTGA
TAGAGTACACAC--------------------------------------------------------------------------------
TCTATTCCAGCCTGGAGTCCTCATGGTTGAGGTAAAATCTCATTGCAAGCTTCACTCCTTTTTTTGCTA
CTTGATCTTTAGAGATCTTGGCTTTGCTTAGGCTGGGTTAATAGAGAGTAAGATTAGCTTGTTTTGAAG
GATACCCCTGGATCATACCTTTATATCAAGAGTTGCTCTATTACGACATAACTAAAGCCAGTAGCATC
TATTCCAGCCAAAATACATGATGAGTCTCCTAATGATTTCATGCTACATAGATTTTCAGACATCTTGTA
CTTAAAAATTATTCAAAGCATTAAAATATACTTTCTCCGTTTCATAAAAAAATGCATGTTTTAGA (SEQ ID NO: 109)

FIG. 8C

MEGANUCLEASE TARGET

WILD-TYPE DNA
TTAGTGGATAGAGTGATAGAGTACACACCTGGTGTATCTGCTGTAGCTATCAAAAACGTTACCATTAAT
GATAATTTCTTTCCTGGGCATTTTCCTGAGAGGCCCATTATGCCTGGAGTCCTC

MUTANT DNA
TTAGTGGATAGAGTGATAGAGTACACAC------------------------------------------------------------
------------------TCTATTCCAGCCTGGAGTCCTC

FIG. 8D

GGATAGAGTGATAGAGTACACAGCTGGTGAATCTGCGGTAGCTATCAAGAACGTTACCATTAATGACA
ATTTCTTTCCTGGGCATTTCCCTGAGAGGCCCATTATGCCTGGTGTCCTCATGGTTGAGGTAATCATCT
CATTGCATGCTTCTCTCTTTTTGCAATACATTCATAGTTCAAGAGAAGTTATTTGATCTCCAGAGTTAGA
AGAATACTTATTAGTGTATATATACTAGCCGGAGTTAGTTGAATTGTTACTTATCATAGCTATATATGAA
CATTTGCTTTATAAGTAAAACCAGTAGCAGTCTGTTCCAGATGTATGTGAGATGAAATGAGTAGGAGA
CTCATTGTGTGTTAATAAGAGCTATATATAGATTGCCTCATCAATTAGTTTTTTTTTTTTTTGGTTTCCAC
AGGCCATGGCTCAGGTGGGAGGTATAGTGATGCTAAATCCAGAAGTGGGCGGATCTAAAAGCAACTT
CTTCTTTGCTGGAGTCGACAAAGTGAGATTCAGAAAGCCTGTGATTGCAGGTGACACTCTGGTGATGA
GGATGACGCTTGTGAAGCTGCAGAAGCGGTTTGGGATAGCCAAAATGGAAGGGAAAGCATACGTAG
GGAACACTTTGGTATGCGAAGGAGAGTTC (SEQ ID NO: 112)

FIG. 8E

GGATAGAGTGATAGAGTACACAGCTGGTGAATCTGCGGTAGCTATCAAGAACGTTACCATTAATGACA
ATTTCTTTCCTGGGCATTTCCCTGAGAGGCCCATTATGCCTGGTGTCCTCATGGTTGAGGTAATCATCT
CATTGCATGCTTCTCTCTTTTTGCAATACATTCATAGTTCAAGAGAAGTTATTTGATCTCCAGAGTTAGA
AGAATACTTATTAGTGTATATATACTAGCCGGAGTTAGTTGAATTGTTACTTATCATAGCTATATATGAA
CATTTGCTTTATAAGTAAAACCAGTAGCAGTCTGTTCCAGATGTATGTGAGATGAAATGAGTAGGAGA
CTCATTGTGTGTTAATAAGAGCTATATATAGATTGCCTCATCAATTAGTTTTTTTTTTTTTTGGTTTCCAC
AGGCCATGGCTCAGGTGGGAGGTATAGTGATGCTAAATCCAGAAGTGGGCGGATCTAAAAGCAACTT
CTTCTTTGCTGGAGTCGACAAAGTGAGATTCAGAAAGCCTGTG---------------------
ATGAGGATGACGCTTGTGAAGCTGCAGAAGCGGTTTGGGATAGCCAAAATGGAAGGGAAAGCATACG
TAGGGAACACTTTGGTATGCGAAGGAGAGTTC (SEQ ID NO: 113)

FIG. 8F

MEGANUCLEASE TARGET

WILD-TYPE DNA
GGAGTCGACAAAGTGAGATTCAGAAAGCCTGTGATTGCAGGTGACACTCTGGTGATGAGGATGACGC
TTGTGAAGCTGCAGAAGCGGTTTGGGATAGCCAAAATGG

MUTANT DNA
GGAGTCGACAAAGTGAGATTCAGAAAGCCTGTG---------------------
ATGAGGATGACGCTTGTGAAGCTGCAGAAGCGGTTTGGGATAGCCAAAATGG

FIG. 8G

ENGINEERED NUCLEASES TO GENERATE MUTATIONS IN PLANTS

CROSS REFERENCE TO RELATED APPLICATIONS

This application is a national phase application of PCT/US2020/012040, filed 2 Jan. 2020, entitled ENGINEERED NUCLEASES TO GENERATE MUTATIONS IN PLANTS, which claims the benefit of priority under 35 U.S.C. § 119(e) to U.S. Provisional Application No. 62/788,578, filed 4 Jan. 2019, entitled ENGINEERED NUCLEASES TO GENERATE MUTATIONS IN PLANTS, the disclosure of which are hereby incorporated herein by reference in their entirety.

SEQUENCE LISTING

This document incorporates by reference herein an electronic sequence listing text file, which is filed in electronic format via EFS-Web. The text file is named "1998439.txt," is 69,632 bytes, and was created on Dec. 31, 2019.

BACKGROUND OF THE INVENTION

In recent years, diets high in saturated fats have been associated with increased levels of cholesterol and increased risk of coronary heart disease. As such, current dietary guidelines indicate that saturated fat intake should be no more than 10 percent of total calories. Based on a 2,000-calorie-a-day diet, this is about 20 grams of saturated fat a day. Oils contain saturated fats. For example, canola oil typically contains about 7% to 8% saturated fatty acids. A decrease in saturated fatty acid content would improve the nutritional profile of oils.

SUMMARY OF THE INVENTION

Genes involved in plant oil synthesis, including those that regulate saturated fatty acid and oleic acid content, have been mutated by a process which involves exposing seeds to chemicals or radiation in order to generate mutants with desirable traits. Unlike plants modified with engineered nucleases, in which a mutation (substitution, deletion and/or addition of one or more nucleotides) can be engineered to occur at a very specific location in the plant genome, plants developed via mutagenic processes often result in random, multiple and unspecific genetic changes. These random, multiple genetic changes all come together to provide the phenotype of the mutated plant. With engineered nucleases, a very specific mutation, or set of mutations, can be generated and their effect on phenotype (e.g., oil profile) can be determined.

Provided herein is the production of mutant sec62 (also annotated as "translocation-protein related"; sec62 is characterized based on its homology to an *Arabidopsis* ortholog, AT3G20920 (arabidopsis.org/servlets/TairObject?name=AT3G20920&type=locus), a member of the 'sec62 proteins' described here: ebi.ac.uk/interpro/entry/IPR004728)), beta-ketoacyl reductase 2 (KCR2), diacylglycerol acyltransferase 1 (DGAT1), fatty acid export 1 (FAX1), microRNA394 (MIR394) and/or beta-hydroxyacyl-acyl carrier protein-dehydratase (HAD) allele(s) generated by the use of engineered nucleases, plants comprising said one or more mutant alleles of sec62, KCR2, DGAT1, FAX1, MIR394 and/or HAD, such as *Brassica* plants, and uses of such plants to produce lower saturated fatty acid content. As described herein, *Brassica* plants containing such mutations can produce oils with reduced saturated fatty acid content. *Brassica* plants described herein are particularly useful for producing canola oils for certain food applications, as the plants are not genetically modified.

Provided herein are *Brassica* plants (e.g., *Brassica napus, Brassica juncea*, or *Brassica rapa* plants) and progeny thereof (e.g., seeds) that include substitution, deletion and/or insertion mutations in one or more alleles of sec62, KCR2, DGAT1, FAX1, MIR394 and/or HAD via engineered nucleases, wherein each mutated allele results in the production of a sec62, KCR2, DGAT1, FAX1, MIR394 and/or HAD polypeptide and/or activity having reduced or no activity relative to a corresponding wild-type sec62, KCR2, DGAT1, FAX1, MIR394 and/or HAD polypeptide and/or activity (alternatively the substitution, deletion and/or insertion may result in no sec62, KCR2, DGAT1, FAX1, MIR394 and/or HAD protein and/or activity being produced) (MIR394 is a microRNA which has activity by itself as an RNA without producing protein). A mutated allele can include a nucleic acid encoding a truncated sec62, KCR2, DGAT1, FAX1, MIR394 and/or HAD polypeptide and/or sequence. A mutated allele can include a sequence having at least 75%, 80%, 85%, 90%, 95%, 96%, 97%, 98%, or 99% sequence identity to the nucleotide sequence of the wild-type allele (e.g., SEQ ID NO: 1 for sec62).

One embodiment provides a method to produce a plant with reduced saturated fatty acids comprising: a) contacting a plant with an engineered nuclease specific for sec62, KCR2, DGAT1, FAX1, MIR394 and/or HAD sequence(s); b) growing the plant from step a) and collecting the seeds from said plant; and c) selecting plants grown from the seeds of step b) with a substitution, deletion and/or insertion mutation in one or more of said sequences; wherein said substitution, deletion and/or insertion mutation results in a reduced production of saturated fatty acids by said plant as compared to a control plant of identical genetic background that has not been mutated by said sequence editing.

Another embodiment provides a method to produce a plant with reduced saturated fatty acids comprising: a) contacting a plant cell or tissue with an engineered nuclease specific for sec62, KCR2, DGAT1, FAX1, MIR394 and/or HAD sequence(s); b) generating a plant from the plant cell or tissue in step a); c) selecting plants of step b) with a substitution, deletion and/or insertion mutation in one or more of said sequences; wherein said substitution, deletion and/or insertion mutation results in a reduced production of saturated fatty acids by said plant as compared to a control plant of identical genetic background that has not been mutated by said sequence editing.

In one embodiment, the plant is a Cruciferae plant. In another embodiment, the plant is a *Brassica* plant. In another embodiment, the plant is *Brassica napus, Brassica juncea*, or *Brassica rapa*.

In one embodiment, the engineered nuclease is a meganuclease. In one embodiment, there is a substitution, deletion and/or insertion mutation in at least one allele of sec62 (in some embodiments the mutated allele is not on N1). In another embodiment, there is a substitution, deletion and/or insertion mutation in at least one allele of KCR2. In another embodiment, there is a substitution, deletion and/or insertion mutation in at least one allele of DGAT1. In one embodiment, there is a substitution, deletion and/or insertion mutation in at least one allele of FAX1. In one embodiment, there is a substitution, deletion and/or insertion mutation in at least one allele of MIR394. In one embodiment, there is a substitution, deletion and/or insertion mutation in at least one allele of HAD.

One embodiment provides a *Brassica* plant comprising a deletion and/or insertion in at least one allele of sec62, KCR2, DGAT1, FAX1, MIR394 and/or HAD. In one embodiment, the deletion and/or insertion is from about 1 to about 400 base pairs in length. In another embodiment, the deletion and/or insertion results in a decrease in saturated fatty acid.

In one embodiment, the recognition/target sequence comprises any contiguous nucleotide (e.g., 10 or more) sequence of the sec62 gene (SEQ ID NO: 1), KCR2 gene (SEQ ID NO: 13), DGAT1 gene (SEQ ID NO: 34), FAX1 gene (SEQ ID NO: 43), MIR394 (SEQ ID NO: 98) and/or HAD gene (SEQ ID NO: 107).

In another embodiment, provided herein is a method of producing an oil. The method includes crushing seeds produced from at least one plant described herein and extracting the oil from the crushed seeds.

One embodiment provides a method to mutate the genome of a *Brassica* plant cell at a target sited comprising: a) inducing a double stranded DNA break at a target site, said double stranded break being induced by the introduction to said cell of a double stranded DNA break inducing (DSBI) enzyme which recognizes a recognition sequence in the vicinity of or at said target site in at least one of sec62, KCR2, DGAT1, FAX1, MIR394 and/or HAD sequences(s); and b) selecting a plant cell wherein said double stranded DNA break has been repaired resulting in a mutation in the genome at said target site, wherein said mutation is a substitution of at least one nucleotide, a deletion of at least one nucleotide, an insertion of at least one nucleotide or any combination thereof. In one embodiment, the plant cell is regenerated into a plant. One embodiment provides a plant cell comprising a mutation at a target site of the genome obtained by the methods provided herein. Another embodiment provides a plant, plant part, seed or propagating material thereof comprising a mutation at a target site of the genome comprising the plant cell.

One embodiment provides a method to produce a *Brassica* plant with reduced saturated fatty acids comprising: a) inducing a double stranded DNA break at a target site, said double stranded break being induced by the introduction to a plant cell of a double stranded DNA break inducing (DSBI) enzyme which recognizes a recognition sequence in the vicinity of or at said target site in at least one of sec62, KCR2, DGAT1, FAX1, MIR394 and/or HAD sequences(s); and b) selecting a plant cell wherein said double stranded DNA break has been repaired resulting in a mutation in the genome at said target site, wherein said mutation is a substitution of at least one nucleotide, a deletion of at least one nucleotide, an insertion of at least one nucleotide or any combination thereof, and c) regenerating said plant cell(s) of b) into a plant; wherein said mutation results in reduced production of saturated fatty acids by said plant as compared to a control plant of identical genetic background that has not been mutated by said DSBI and repair.

In one embodiment, the DSBI enzyme is a single chain meganuclease or a pair of meganucleases which recognizes or recognize in concert a site and induces or induce said double strand break.

In one embodiment, the plant(s) produced by the methods described herein is crossed with another plant.

One embodiment provides a plant, plant part, seed or propagating material thereof comprising a modification at a target site of the genome obtained by the methods provided here.

In one embodiment, the plant is *Brassica napus, Brassica juncea*, or *Brassica rapa.*

In one embodiment, one or multiple sec62 alleles on N11, N13, and/or N15 are mutated. In another embodiment, one or multiple KCR2 alleles on N7, N17, N9, and/or N15 are mutated. In one embodiment, one or both DGAT1 alleles on N9 and/or N19 are mutated. In another embodiment, one or multiple FAX1 alleles on N7, N9 and/or N18 are mutated. In one embodiment, one or both MIR394 alleles on N16 and/or N7 are mutated. In one embodiment, one or both HAD alleles on N2 and/or N3 are mutated. In one embodiment, the mutation is a deletion or insertion of one or more nucleotides, optionally comprising the substitution of at least one nucleotide.

In one embodiment, the plants produced by the methods described herein yield a reduction of stearic acid (18:0) of about 6% to about 27% as compared to a non-mutated plant of identical genetic background. In another embodiment, the plants yield an overall reduction in total saturated fatty acids of about 2 to about 12%.

In some embodiments the methods and/or mutated plants provide a reduction of total saturated fatty acids is about 2%, about 3%, about 4%, about 5%, about 6%, about 7%, about 8%, about 9%, about 10%, about 11% or about 12%.

In other embodiments, the methods and/or mutated plants provide a reduction of total saturated fatty acids is about 2% to about 4%, about 3% to about 6%, about 2% to about 7%, about 5% to about 12%, about 6% to about 9% or about 8% to about 9%.

Some embodiments provide methods and/or mutated plants with a reduction of steric acid is about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26% or about 27%.

Some embodiments provide methods and/or mutated plants with a reduction of steric acid about 6% to about 15%, 9% to about 12%, about 11% to about 17%, about 13% to about 17%, about 15% to about 22%, about 16% to about 20%, about 20% to about 24% or about 24% to about 27%.

BRIEF DESCRIPTION OF THE DRAWINGS

FIGS. 1A-1J provide A) the full-length sequence of sec62 (N13, wild type; publicly available; Chalhoub et al. 2014) (SEQ ID NO: 1); B) depicts partial sequence for wild type sec62 N13 (SEQ ID NO: 2); C) depicts partial sequence for sec62 N13 mutant (9 bp deletion; SEQ ID NO: 3); D) depicts the meganuclease recognition site; partial wild type sec62 N13 nucleotide sequence (SEQ ID NO: 4) and partial mutant sequence depicting deletion (SEQ ID NO: 5); E) depicts partial sequence for wild type sec62 N15 (SEQ ID NO: 6); F) depicts partial sequence for sec62 N15 mutant (9 bp insertion; SEQ ID NO: 7); G) depicts the meganuclease recognition site; partial wild type sec62 N15 nucleotide sequence (SEQ ID NO: 118) and partial mutant sequence depicting insertion (SEQ ID NO: 8); H) depicts partial sequence for wild type sec62 N11 (SEQ ID NO: 9); I) depicts partial sequence for sec62 N11 mutant (4 bp deletion; SEQ ID NO: 10); and J) depicts the meganuclease recognition site; partial wild type sec62 N11 nucleotide sequence (SEQ ID NO: 11) and partial mutant sequence depicting deletion (SEQ ID NO: 12)

FIGS. 2A-2P provide A) the full-length sequence of KCR2 (N9, wild type; publicly available sequence; Chalhoub et al. 2014) (SEQ ID NO: 13); B) depicts partial sequence for wild type KCR2 N9 (SEQ ID NO: 14); C) depicts partial sequence for KCR2 N9 mutant (24 bp deletion; SEQ ID NO: 15); D) depicts the meganuclease recognition site; partial wild type KCR2 N9 nucleotide sequence (SEQ ID NO: 16) and partial mutant sequence depicting deletion (SEQ ID NO: 17); E) depicts partial sequence for wild type KCR2 N15 (SEQ ID NO: 18); F) depicts partial sequence for KCR2 N15 mutant (13 bp deletion; SEQ ID NO: 19); G) depicts the meganuclease recognition site; partial wild type KCR2 N15 nucleotide sequence (SEQ ID NO: 20) and partial mutant sequence depicting deletion (SEQ ID NO: 21); H) depicts partial sequence for wild type KCR2 N7 (SEQ ID NO: 22); I) depicts partial sequence for KCR2 N7 mutant (1 bp insertion; SEQ ID NO: 23); J) depicts the meganuclease recognition site; partial wild type KCR2 N7 nucleotide sequence (SEQ ID NO: 24) and partial mutant sequence depicting insertion (SEQ ID NO: 25); K) depicts partial sequence for wild type KCR2 N7 (SEQ ID NO: 26); L) depicts partial sequence for KCR2 N7 mutant (15 bp deletion (SEQ ID NO: 27); M) depicts the meganuclease recognition site; partial wild type KCR2 N7 nucleotide sequence (SEQ ID NO: 28) and partial mutant sequence depicting deletion (SEQ ID NO: 29); N) depicts partial sequence for wild type KCR2 N17 (SEQ ID NO: 30); O) depicts partial sequence for KCR2 N17 mutant (1 bp insertion; SEQ ID NO: 31); and P) depicts the meganuclease recognition site; partial wild type KCR2 N17 nucleotide sequence (SEQ ID NO: 32) and partial mutant sequence depicting insertion (SEQ ID NO: 33).

FIGS. 3A-3G provide A) the full-length sequence of DGAT1 (N17, wild type; publicly available sequence; Chalhoub et al. 2014) (SEQ ID NO: 34); B) depicts partial sequence for wild type DGAT1 N9 (SEQ ID NO: 35); C) depicts partial sequence for DGAT N9 mutant (5 bp deletion; SEQ ID NO: 36); D) depicts the meganuclease recognition site; partial wild type DGAT1 N9 nucleotide sequence (SEQ ID NO: 37) and partial mutant sequence depicting deletion (SEQ ID NO: 38); E) depicts partial sequence for wild type DGAT1 N19 (SEQ ID NO: 39); F) depicts partial sequence for DGAT N19 mutant (10 bp deletion; SEQ ID NO: 40); and G) depicts the meganuclease recognition site; partial wild type DGAT1 N19 nucleotide sequence (SEQ ID NO: 41) and partial mutant sequence depicting deletion (SEQ ID NO: 42).

FIGS. 4A-4N provide A) the full-length sequence of FAX1 (N9, wild type; publicly available sequence; Chalhoub et al. 2014) (SEQ ID NO: 43); B) depicts partial sequence for wild type FAX1 N9 (SEQ ID NO: 44); C) depicts partial sequence for FAX1 N9 mutant (8 bp deletion; SEQ ID NO: 45); D) depicts the meganuclease recognition site; partial wild type FAX1 N9 nucleotide sequence (SEQ ID NO: 46) and partial mutant sequence depicting deletion (SEQ ID NO: 47); E) depicts partial sequence for FAX1 N9 mutant (19 bp deletion; SEQ ID NO: 48); F) depicts the meganuclease recognition site; partial wild type FAX1 N9 nucleotide sequence (SEQ ID NO: 49) and partial mutant sequence depicting deletion (SEQ ID NO: 50); G) depicts partial sequence for wild type FAX N18 (SEQ ID NO: 51); H) depicts partial sequence for FAX1 N18 mutant (87 bp deletion; SEQ ID NO: 52); I) depicts the meganuclease recognition site; partial wild type FAX1 N18 nucleotide sequence (SEQ ID NO: 53) and partial mutant sequence depicting deletion (SEQ ID NO: 54); J) depicts partial sequence for wild type FAX N7 (SEQ ID NO: 55); K) depicts partial sequence for FAX1 N7 mutant (3 bp deletion; SEQ ID NO: 56); L) depicts the meganuclease recognition site; partial wild type FAX1 N7 nucleotide sequence (SEQ ID NO: 57) and partial mutant sequence depicting deletion (SEQ ID NO: 58); M) depicts partial sequence for FAX1 N7 mutant (1 bp insertion; SEQ ID NO: 59); and N) depicts the meganuclease recognition site; partial wild type FAX1 N7 nucleotide sequence (SEQ ID NO: 60) and partial mutant sequence depicting insertion (SEQ ID NO: 61).

FIGS. 5A-5Q provide A) the full-length sequence of PDAT1 (N12, wild type; publicly available sequence; Chalhoub et al. 2014) (SEQ ID NO: 62); B) depicts partial sequence for wild type PDAT1 N2 (SEQ ID NO: 63); C) depicts partial sequence for PDAT1 N2 mutant (5 bp deletion; SEQ ID NO: 64); D) depicts the meganuclease recognition site; partial wild type PDAT1 N2 nucleotide sequence (SEQ ID NO: 65) and partial mutant sequence depicting deletion (SEQ ID NO: 66); E) depicts partial sequence for wild type PDAT1 N12 (SEQ ID NO: 67); F) depicts partial sequence for PDAT1 N12 mutant (79 bp deletion; SEQ ID NO: 68); G) depicts the meganuclease recognition site; partial wild type PDAT1 N12 nucleotide sequence (SEQ ID NO: 69) and partial mutant sequence depicting deletion (SEQ ID NO: 70); H) depicts partial sequence for wild type PDAT1 N10 (SEQ ID NO: 71); I) depicts partial sequence for PDAT1 N10 mutant (15 bp deletion; SEQ ID NO: 72); J) depicts the meganuclease recognition site; partial wild type PDAT1 N10 nucleotide sequence (SEQ ID NO: 73) and partial mutant sequence depicting deletion (SEQ ID NO: 74); K) depicts partial sequence for PDAT1 N10 mutant (21 bp deletion; SEQ ID NO: 75); L) depicts the meganuclease recognition site; partial wild type PDAT1 N10 nucleotide sequence (SEQ ID NO: 76) and partial mutant sequence depicting deletion (SEQ ID NO: 77); M) depicts partial sequence for wild type PDAT1 N19 (SEQ ID NO: 78); N) depicts partial sequence for PDAT1 N19 mutant (8 bp deletion; SEQ ID NO: 79); O) depicts the meganuclease recognition site; partial wild type PDAT1 N19 nucleotide sequence (SEQ ID NO: 80) and partial mutant sequence depicting deletion (SEQ ID NO: 81); P) depicts partial sequence for PDAT1 N19 mutant (213 bp deletion; SEQ ID NO: 82); and Q) depicts the meganuclease recognition site; partial wild type PDAT1 N19 nucleotide sequence (SEQ ID NO: 83) and partial mutant sequence depicting deletion (SEQ ID NO: 84).

FIGS. 6A-6J provide A) the full-length sequence of ENR (N13, wild type; publicly available sequence; Chalhoub et al. 2014) (SEQ ID NO: 85); B) depicts partial sequence for wild type ENR N3 (SEQ ID NO: 86); C) depicts partial sequence for ENR N3 mutant (6 bp deletion; SEQ ID NO: 87); D) depicts the meganuclease recognition site; partial wild type ENR N3 nucleotide sequence (SEQ ID NO: 88) and partial mutant sequence depicting deletion (SEQ ID NO: 89); E) depicts partial sequence for wild type ENR N7 (SEQ ID NO: 90); F) depicts partial sequence for ENR N7 mutant (1 bp deletion; SEQ ID NO: 91); G) depicts the meganuclease recognition site; partial wild type ENR N7 nucleotide sequence (SEQ ID NO: 92) and partial mutant sequence depicting deletion (SEQ ID NO: 93); H) depicts partial sequence for wild type ENR N13 (SEQ ID NO: 94); I) depicts partial sequence for ENR N13 mutant (377 bp deletion; SEQ ID NO: 95); and J) depicts the meganuclease recognition site; partial wild type ENR N7 nucleotide sequence (SEQ ID NO: 96) and partial mutant sequence depicting deletion (SEQ ID NO: 97).

FIGS. 7A-7G provide A) the full-length sequence of MIR394 (N7, wild type; publicly available sequence; Chalhoub et al. 2014) (SEQ ID NO: 98); B) depicts partial sequence for wild type MIR394 N16b (SEQ ID NO: 99); C) depicts partial sequence for MIR394 N16b mutant (35 bp deletion and 2 bp changes; SEQ ID NO: 100); D) depicts the meganuclease recognition site; partial wild type MIR394 N16b nucleotide sequence (SEQ ID NO: 101) and partial mutant sequence depicting deletion (SEQ ID NO: 102); E) depicts partial sequence for wild type MIR394 N7c (SEQ ID NO: 103); F) depicts partial sequence for MIR394 N7c mutant (17 bp deletion; SEQ ID NO: 104); and G) depicts the meganuclease recognition site; partial wild type MIR394 N16b nucleotide sequence (SEQ ID NO: 105) and partial mutant sequence depicting deletion (SEQ ID NO: 106).

FIGS. 8A-8G provide A) the full-length sequence of HAD (N3, wild type; publicly available sequence; Chalhoub et al. 2014) (SEQ ID NO: 107); B) depicts partial sequence for wild type HAD N2 (SEQ ID NO: 108); C) depicts partial sequence for HAD N2 mutant (73 bp deletion; SEQ ID NO: 109); D) depicts the meganuclease recognition site; partial wild type HAD N2 nucleotide sequence (SEQ ID NO: 110) and partial mutant sequence depicting deletion (SEQ ID NO: 111); E) depicts partial sequence for wild type HAD N3 (SEQ ID NO: 112); F) depicts partial sequence for HAD N3 mutant (21 bp deletion; SEQ ID NO: 113); and G) depicts the meganuclease recognition site; partial wild type HAD N2 nucleotide sequence (SEQ ID NO: 114) and partial mutant sequence depicting deletion (SEQ ID NO: 115).

DETAILED DESCRIPTION OF THE INVENTION

Methods are provided to mutate, in a targeted manner, the genome of a plant using a double stranded DNA break inducing enzyme. Also provided are plants, in particular *Brassica* plants, which yield seeds producing oils having a reduced saturated fatty acid content, and method for making such plants.

The invention provides methods to introduce a targeted mutation, including insertion, deletion, or substitution of one or more nucleotides, at a precisely localized nucleotide sequence in the genome of a plant using engineered double stranded DNA break inducing enzymes. The invention further provides a plant cell, plant part, plant or seed comprising such a mutated sequence, wherein said mutation results in a reduction of saturated fatty acid production by the plant, and methods for making such plant.

The invention is based on the observation that functional meganucleases can be engineered to specifically recognize and cleave a nucleotide sequence, such as sec62 (SEQ ID NO: 1), in a plant cell, from which a plant can be produced. Provided herein are plants produced by the methods provided herein, such as *Brassica* plants including *B. napus, B. juncea*, and *B. rapa* species of *Brassica*, that yield seeds producing oils having a reduced saturated fatty acid content.

Definitions

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Any methods and materials similar or equivalent to those described herein can be used in the practice or testing of the present invention. Specific and preferred values listed below for radicals, substituents, and ranges are for illustration only; they do not exclude other defined values or other values within defined ranges for the radicals and substituents.

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, a "double stranded DNA break endonuclease" is an enzyme capable of inducing a double stranded DNA break at a particular nucleotide sequence, called the "recognition site." Homing endonucleases constitute a family of endonucleases and are sometimes also referred to as meganucleases. They may be encoded by introns, independent genes or intervening sequences, and present structural and functional properties that distinguish them from the more classical restriction enzymes, usually from bacterial restriction-modification Type II systems.

A person skilled in the art would be able to either choose a double stranded DNA break inducing ("DSBI") enzyme recognizing the selected target nucleotide sequence to engineer such a DSBI endonuclease.

As used herein "located in the vicinity" refers to the site of double DNA stranded break induction, i.e. the recognition site of the DSBI enzyme, being located at a distance of 0 bp, 10 bp, 20 bp, 30 bp, 50 bp, 60 bp, 70 bp, 80 bp, 90 bp, 100 bp, 200, 250 bp, 500 bp, 1 kbp, 2 kbp, 3 kbp, 4 kbp, 5 kbp to 10 kbp from the target, i.e. the site in the genomic DNA which is to be mutated (the target site).

The term "heterologous" refers to the relationship between two or more nucleic acid or protein sequences that are derived from different sources. For example, a promoter is heterologous with respect to an operably linked nucleic acid sequence, such as a coding sequence, if such a combination is not normally found in nature. In addition, a particular sequence may be "heterologous" with respect to a cell or organism into which it is inserted (i.e. does not naturally occur in that particular cell or organism).

The expression "operably linked" means that said elements of the chimeric gene are linked to one another in such a way that their function is coordinated and allows expression of the coding sequence, i.e. they are functionally linked. By way of example, a promoter is functionally linked to another nucleotide sequence when it is capable of ensuring transcription and ultimately expression of said other nucleotide sequence.

A nullizygous organism carries two mutant or missing alleles for the same gene. The mutant/missing alleles are both complete loss-of-function or 'null' alleles, so homozygous null and nullizygous are synonymous.

A gene knockout (abbreviation: KO) is a genetic technique in which both of an organism's alleles are made inoperative ("knocked out" of the organism). The term knockout, inactivated, and disrupted are used interchangeably herein to mean that the targeted site is changed so that the gene expression product is eliminated or greatly reduced, or the product expressed has reduced activity as compared to a control (e.g., wild type protein). Also known as knockout organisms or simply knockouts. The term also refers to the process of creating such an organism, as in "knocking out" a gene.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, "plant part" includes any plant organ or plant tissue, including but not limited to fruits, seeds, embryos, meristematic regions, callus tissue, leaves, roots, shoots, flowers, gametophytes, sporophytes, pollen, and microspores.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The optimal alignment of the two sequences is performed by the Needleman and Wunsch algorithm (Needleman and Wunsch 1970). The computer-assisted sequence alignment above, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

Nucleic acids can be DNA or RNA, single- or double-stranded. Nucleic acids can be synthesized chemically or produced by biological expression in vitro or in vivo. Nucleic acids can be chemically synthesized using appropriately protected ribonucleoside phosphoramidites and a conventional DNA/RNA synthesizer. DNA includes cDNA and genomic DNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience, Hoboken, N.J. (1987).

The terms "comprises," "comprising," and the like can have the meaning ascribed to them in U.S. Patent Law and can mean "includes," "including" and the like. As used herein, "including" or "includes" or the like means including, without limitation.

Plants

Plants, such as *Brassica* plants, described herein have reduced levels of total saturated fatty acids in the seed oil as a result of reduced activity of sec62, KCR2, DGAT1, FAX1, MIR394 and/or HAD (and optionally PDAT1 and/or ENR). It is understood that throughout the disclosure, reference to "plant" or "plants" includes progeny, i.e., descendants of a particular plant or plant line, as well as cells or tissues from the plant. Progeny of an instant plant include seeds formed on $F_1$, $F_2$, $F_3$, $F_4$ and subsequent generation plants, or seeds formed on $BC_1$, $BC_2$, $BC_3$, and subsequent generation plants. Seeds produced by a plant can be grown and then selfed (or outcrossed and selfed or doubled through dihaploid) to obtain seeds homozygous for a mutant allele. The term "allele" or "alleles" refers to one or more alternative forms of a gene at a particular locus.

Reduced activity, including absence of detectable activity, of sec62, KCR2, DGAT1, FAX1, MIR394 and/or HAD (and optionally PDAT1 and/or ENR), can be achieved by mutating one or more endogenous sec62, KCR2, DGAT1, FAX1, MIR394 and/or HAD (and optionally PDAT1 and/or ENR) allele(s) (each of these genes has one or more isoforms, for example, sec62 has 6 isoforms, namely one on each of chromosome N1, N11, N13, N15, N3, and N5 (in one embodiment, the mutation of sec62 is not on chromosome N1); KCR2 has 4 isoforms, namely one on each of chromosomes N7, N17, N9, and N15; DGAT1 has 4 isoforms, namely one on each of chromosomes N9, N19, N7, and N17; FAX1 has 4 isoforms, namely one on each of chromosomes N7, N9, N16 and N18; PDAT1 has 4 isoforms, namely one on each of chromosomes N2, N12, N10 and N19; ENR has 4 isoforms, namely one on each of chromosomes N3, N7, N13, and N17; MIR394 has 4 isoforms, namely two on each of chromosomes N16 and N7; and HAD has 4 isoforms, namely one on each of chromosomes N2, N3, N12, and N13. An endogenous isoform/allele of sec62, KCR2, DGAT1, FAX1, MIR394 and/or HAD (and optionally PDAT1 and/or ENR) can be mutated (deletion, addition and/or substitution mutation) using engineered nucleases.

Genetic mutations can be introduced within, for example, regenerable plant tissue using one or more engineered nucleases. The treated population, or a subsequent generation of that population, can be screened for reduced protein activity that results from the mutation, e.g., by determining the fatty acid profile of the population and comparing it to a corresponding non-mutagenized population. Mutations can be in any portion of a gene, including coding sequence, intron sequence and regulatory elements, that render the resulting gene product non-functional or with reduced activity.

The plants on which the genetic mutations can be carried out are any plants, including those in the *Brassica* family, including any wild-type and mutant plant backgrounds. Such *Brassica* plants include, but are not limited to, IMC201 (U.S. Pat. No. 9,334,483), IMC02 (represented by American Type Culture Collection (ATCC) Accession No. PTA-6221), Westar (U.S. Pat. No. 6,342,658), 1904 (represented by American Type Culture Collection (ATCC) Accession No. PTA-11273, as well as progeny of the seed designated 1904 and represented by ATCC Accession No. PTA-11273), 2558 (represented by American Type Culture Collection (ATCC) Accession No. PTA-11274, as well as progeny of the seed designated 2558 and represented by ATCC Accession No. PTA-11274), US Pub Appln No. 2013/0081156, 95CB504 (U.S. Pat. No. 9,334,483), Cargill background (represented by American Type Culture Collection (ATCC) Accession No. PTA-12314, PTA-12315 and PTA-12316), 03LC LL and hybrid backgrounds deposited as Accession No. PTA-12314, PTA-12315 and PTA-12316, and Topas (represented by American Type Culture Collection (ATCC) Accession No. PTA-120738).

Engineered Nucleases

The use of engineered nucleases (GEEN) is a type of genetic engineering in which DNA is inserted, deleted or substituted in the genome of an organism using engineered nucleases, or "molecular scissors." These nucleases create site-specific double-strand breaks (DSBs) at desired locations in the genome. The induced double-strand breaks are repaired resulting in targeted mutations, such as deletions.

There are currently four families of engineered nucleases being used: meganucleases, zinc finger nucleases (ZFNs), Transcription Activator-Like Effector-based Nucleases (TALEN), and the CRISPR-Cas system (Esvelt, K M. and Wang, H H. (2013). "Genome-scale engineering for systems and synthetic biology." Mol Syst Biol 9 (1): 641; Tan, W S. et al. (2012). "Precision editing of large animal genomes." Adv Genet 80: 37-97; Puchta, H. and Fauser, F. (2013). "Gene targeting in plants: 25 years later." Int. J. Dev. Biol 57: 629-637; Boglioli, E. and Richard, M. "Rewriting the book of life: a new era in precision genome editing" (PDF). Boston Consulting Group; Method of the Year 2011. Nat Meth 9 (1), 1-1; www.sciencemag.org/topic/2015-breakthrough-year).

Meganucleases, found commonly in microbial species, have the unique property of having long recognition sequences (>14 bp) thus making them naturally specific (de Souza, N., Primer: genome editing with engineered nucleases. Nat Meth 9 (1), 27-27 (2011); Smith, J. et al., A combinatorial approach to create artificial homing endonucleases cleaving chosen sequences. Nucleic Acids Research 34 (22), e149 (2006)). This can be exploited to make site-specific DSB in genome editing. Meganuclease variants that recognize unique sequences have been created (Id). Also, of use is the fusion of various meganucleases to create hybrid enzymes that recognize a new sequence (Chevalier, B. S. et al., Design, Activity, and Structure of a Highly Specific Artificial Endonuclease" Molecular Cell 10 (4), 895-905 (2002)). Yet others have altered the DNA interacting amino acids of the meganuclease to design sequence specific meganucelases in a method named rationally designed meganuclease (U.S. Pat. No. 8,021,867; WO2007/047859; WO2011/064736).

A well characterized megaendonuclease is I-SceI. I-SceI is a site-specific endonuclease, responsible for intron mobility in mitochondria in *Saccharomyces cerevisea*. The enzyme is encoded by the optional intron Sc LSU.1 of the 21 S rRNA gene and initiates a double stranded DNA break at the intron insertion site generating a 4 bp staggered cut with 3'OH overhangs. The recognition site of I-SceI endonuclease extends over an 18 bp non-symmetrical sequence (Colleaux et al. 1988 Proc. Natl. Acad. Sci. USA 85: 6022-6026). The amino acid sequence for I-SceI and a universal code equivalent of the mitochondrial I-SceI gene have been provided by e.g. WO 96/14408. WO 96/14408 further discloses a number of variants of I-SceL protein which are still functional. PCT application PCT/EP04/013122 (incorporated herein by reference) provides synthetic nucleotide sequence variants of I-SceL which have been optimized for expression in plants.

Another well characterized designed meganuclease is based on the naturally occurring meganuclease I-CreI for use as a scaffold. I-CreI is an endonuclease found in the chloroplasts of *Chlamydomonas rheinhardti* (Thompson et al. 1992, Gene 119, 247-251). This endonuclease is a homodimer that recognizes a pseudo-palindromic 22 bp DNA site in the 23SrRNA gene and creates a double stranded DNA break that can be used for the introduction of an intron. I-CreI is a member of a group of endonucleases carrying a single LAGLIDADG (SEQ ID NO: 116) motif LAGLIDADG (SEQ ID NO: 117) enzymes contain one or two copies of the consensus motif. Single-motif enzymes, such as I-CreI function as homodimers, whereas double-motif enzymes are monomers with two separate domains. Accordingly, when designing meganucleases derived from an I-CreI scaffold to recognize a 22 bp nucleotide sequence of interest, two monomeric units are designed, each recognizing a part of the 22 bp recognition site, which are needed in concert to induce a double stranded break at the 22 bp recognition site (WO2007/047859). Concerted action may be achieved by linking the two monomeric units into one single chain meganuclease or may also be achieved by promoting the formation of heterodimers, as described e.g. in WO2007/047859.

A list of other DSB inducing enzymes and their respective recognition sites is provided in Table I of WO 03/004659 (pages 17 to 20) (incorporated herein by reference). These include I-See I, I-Chu I, I-Dmo I, I-Cre I, I-Csm I, PI-Fli I, Pt-Mtu I, I-Ceu I, I-See II, I-See III, HO, PI-Civ I, PI-Ctr I, PI-Aae I, PI-BSU I, PI-DhaI, PI-Dra I, PI-May I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fae I, PI-Mja I, PI-Pho I, PI-Tag I, PI-Thy I, PI-Tko I or PI-Tsp I.

As opposed to meganucleases, the concept behind ZFNs and TALEN technology is based on a non-specific DNA cutting enzyme, which can then be linked to specific DNA sequence recognizing peptides, such as zinc fingers (such methods have been described e.g. in WO 03/080809, WO94/18313 or WO95/09233 and in Isalan et al., 2001, Nature Biotechnology 19, 656-660; Liu et al. 1997, Proc. Natl. Acad. Sci. USA 94, 5525-5530)) and transcription activator-like effectors (TALEs; Baker, M., Gene-editing nucleases. Nat Meth 9 (1), 23-26 (2012); Christian et al., 2010, Genetics 186: 757-761, WOl0/079430 and WO10/146121). In these technologies, the endonuclease has a DNA recognition site and cleaving site separate from each other. Although the nuclease portions of both ZFNs and TALEN constructs have similar properties (e.g., FokI), the difference between these engineered nucleases is in their DNA recognition peptide. ZFNs rely on Cys2-His2 zinc fingers and TALEN constructs on TALEs. Both of these DNA recognizing peptide domains have the characteristic that they are naturally found in combinations in their proteins. Cys2-His2 Zinc fingers typically happen in repeats that are 3 bp apart and are found in diverse combinations in a variety of nucleic acid interacting proteins such as transcription factors. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities (de Souza, N., Primer: genome editing with engineered nucleases. Nat Meth 9 (1), 27-27 (2011)). Zinc fingers have been more established in these terms and approaches such as modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries among other methods have been used to make site specific nucleases.

Another way of producing custom-made meganucleases, by selection from a library of variants, is described in WO2004/067736. Custom made meganucleases with altered sequence specificity and DNA-binding affinity may also be obtained through rational design as described in WO2007/

047859. Such custom designed endonucleases are also referred to as a non-naturally occurring endonucleases.

The designed double stranded break inducing enzyme may comprise, but need not comprise, a nuclear localization signal (NLS), such as the NLS of SV40 large T-antigen (Raikhel, Plant Physiol. 100: 1627-1632 (1992) and references therein) (Kalderon et al. Cell 39: 499-509 (1984)). The nuclear localization signal may be located anywhere in the protein but is conveniently located at the N-terminal end of the protein. The nuclear localization signal may replace one or more of the amino acids of the double stranded break inducing enzyme.

Conveniently, the DSBI enzyme can be provided by expression of a plant expressible recombinant gene(s) encoding such enzyme(s). To this end, a DNA region comprising a nucleotide sequence encoding, for example, a designed meganuclease or meganuclease monomeric unit can be operably linked to a plant-expressible promoter and optionally a DNA region involved in transcription termination and polyadenylation and introduced into a plant, plant part or plant cell(s). The recombinant gene(s) encoding DSBI enzyme may be introduced transiently or stably. The DSBI enzyme may also be introduced into the plant, plant part or plant cell(s) by introducing into the cell an RNA molecule which is translated into the DSBI enzyme. Alternatively, the DSBI enzyme may be introduced into the plant, plant part or plant cell(s) directly as a protein. Methods for the introduction of DNA or RNA molecules or proteins into a plant, plant part, tissue or plant cell(s) are available to an art worker and briefly described below.

Described herein, the term "plant operative promoter" and "plant-expressible promoter" mean a promoter which is capable of driving transcription in a plant, plant tissue, plant organ, plant part, or plant cell. This includes any promoter of plant origin, but also any promoter of non-plant origin which can direct transcription in a plant cell.

Promoters that may be used in this respect are constitutive promoters, such as the promoter of the cauliflower mosaic virus (CaMV) 35S transcript (Hapster et al., 1988, Md. Gen. Genet. 212: 182-190), the CaMV 19S promoter (U.S. Pat. No. 5,352,605; WO 84/02913; Benfey et al., 1989, EMBO J. 8:2195-2202), the subterranean clover virus promoter No 4 or No 7 (WO 96/06932), the Rubisco small subunit promoter (U.S. Pat. No. 4,962,028), the ubiquitin promoter (Holtorf et al., 1995, Plant Mal. Biol. 29:637-649), T-DNA gene promoters such as the octopine synthase (OCS) and nopaline synthase (NOS) promoters from *Agrobacterium*, and further promoters of genes whose constitutive expression in plants is available to the person skilled in the art.

Further promoters that may be used in this respect are tissue-specific or organ-specific promoters, such as seed-specific promoters, such as the 2S albumin promoter (Joseffson et al., 1987, J. Biol. Chem. 262:12196-12201), the phaseolin promoter (U.S. Pat. No. 5,504,200; Bustos et al., 1989, Plant Cell 1. (9):839-53), the legumine promoter (Shirsat et al., 1989, Mal. Gen. Genet. 215(2):326-331), the "unknown seed protein" (USP) promoter (Baumlein et al., 1991, Mal. Gen. Genet. 225(3):459-67), the napin promoter (U.S. Pat. No. 5,608,152; Stalberg et al., 1996, Planta 199: 515-519), the *Arabidopsis* oleosin promoter (WO 98/45461), the *Brassica* Bce4 promoter (WO 91/13980), and further promoters of genes whose seed-specific expression in plants is available to the person skilled in the art.

Plant Gene Editing

The use of meganucleases, ZFNs, CRISPR and TALEN, provides a novel strategy for genetic manipulation in plants and can assist in the engineering of desired plant traits by mutating endogenous genes.

Using engineered nucleases, or any method available to an art worker, various genes can be mutated (so as to create a deletion mutation/truncation, addition of one more nucleotides and/or mutating one or more nucleotides (changing its sequence/substitution) and not a mutation by insertion of foreign/non-endogenous DNA), including sec62; KCR2; DGAT1; FAX1; MIR394; HAD; PDAT1; and/or ENR of a plant, such as a Cruciferae plant, for example a *Brassica* plant (Chalhoub et al. Science (345) 2014), including a plant of the *Brassica napus, Brassica juncea*, or *Brassica rapa* species. In one embodiment, the plant is an oilseed crop, such as flax (*Linum* sp.), rapeseed (*Brassica* sp.), soybean (Glycine sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, oil palm, coconuts, groundnuts, sesame seed, castor bean, lesquerella, tallow tree, shea nuts, poppy seed, and/or jojoba seeds. Thus, provided herein are genes and plants, such as *Brassica* plants, that include modified alleles of, for example, sec62, KCR2, DGAT1, FAX1 and/or HAD (and optionally PDAT1 and/or ENR), that result in the production of the protein encoded by the gene to have reduced activity or no activity (as compared to wild type sec62, KCR2, DGAT1, FAX1 and/or HAD (and optionally PDAT1 and/or ENR)) or results in little to no protein product being produced or results in reduced to no activity of MIR394 or reduced to no production of MIR394.

For example, through use of a targeted/designed meganuclease and endogenous repair mechanisms, an insertion, substitution or deletion mutation can be created in any one of the genes described herein. A deletion or insertion mutation can be from 1 nucleotide to 400 plus nucleotides in length, including for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 342, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400 nucleotides and so on (and any range encompassing such numbers or the entire gene). Such deletions and/or insertions can result in little to no expression of the gene (RNA and/or protein) and if protein is expressed from the gene, it will have no or reduced activity as compared to a wild type gene.

The engineered nuclease is provided to plants or plant tissues via conventional methods (e.g., DNA coding for engineered nuclease is inserted into a plasmid (generally operably linked components comprising a promoter sequence, engineered nuclease, terminator (stop) sequence and optionally an antibiotic resistance gene)) and introduced into the plant cells by any method available to the art, including for example into bacteria, such as *Agrobacterium tumefaciens*, but also by direct DNA transfer methods. Various methods for DNA delivery into cells/tissues (intact plant cells or partially degraded tissues or plant cells) are known in the art, and include electroporation as illustrated in U.S. Pat. No. 5,384,253; microprojectile bombardment (biolistics) as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,635,055; 5,824,877; 5,591,616; 5,981,840; and 6,384,301; protoplast transformation as illustrated in U.S. Pat. No. 5,508,184, electroporation, chemically-assisted transformation, liposome-mediated transformation (see, e.g., A. Deshayes, et al. (1985) EMBO J. 4:2731-7.), carbon fiber, silicon carbide fiber or aluminum borate fiber (generally termed whiskers) (see, e.g., J. Brisibe, Exp. Bot. 51 (343): 187-196 (2000); Dunwell (1999) Methods Mol. Biol. 111:375-82; and U.S. Pat. No. 5,464,765), micro-injection (see, e.g., T J. Reich, of al. (1986) Biotechnology 4: 1001-1004) and viral-mediated transformation (see, e.g., S. B. Gelvin, (2005) Nat Biotechnol. 23: 684-5, WO 90/12107, WO 03/052108 and WO 2005/098004), bombardment of plant cells with heterologous foreign DNA adhered to particles, ballistic particle acceleration, aerosol beam transformation (U.S. Patent Application No. 20010026941; U.S. Pat. No. 4,945,050; International Publication No. WO 91/00915; U.S. Patent Application No. 2002015066, WO 01/038514; all incorporated herein by reference), Led transformation, PEG transformation, and various other non-particle direct-mediated methods to transfer DNA. As used herein "direct DNA transfer" is any method of DNA introduction into plant cells which does not involve the use of natural *Agrobacterium* spp. and which is capable of introducing DNA into plant cells.

It will also be clear that the terms used to describe the method such as "introduction of a DNA" as well as "regeneration of a plant from the cell" do not imply that such DNA necessarily needs to be introduced by transformation techniques. Indeed, it will be immediately clear to the person skilled in the art that the DNA molecule of interest may also be introduced by breeding or crossing techniques from one plant to another. Thus, "introducing" in connection with the present application relate to the placing of genetic information in a plant cell or plant by any known means. This can be affected by any method known in the art for transforming RNA or DNA into plant cells, tissues, protoplasts or whole plants or by introgressing said RNA or DNA into plants.

In the case of introducing DNA into a plant, plant tissue or pant cell(s) in which the mutation is desired (e.g., canola plant or plant tissue; including, for example, several varieties of the Brassicaceae plants, including for example, *Brassica napus, Brassica rapa, B. campestris* or *Brassica juncea* and mutated *Brassica* plants) via *Agrobacterium tumefaciens*, the plant, plant tissues, or plant cell(s) is exposed to the bacteria carrying the engineered nuclease. For example, the plant can be dipped in a solution comprising the bacterium or disks can be punched out from a plant leaf (or other plant tissue, such as the stems, can be used) and incubated with a culture of plasmid-containing *A. tumefaciens*. The disks/plant tissue are then placed under conditions to generate callus in the presence of antibiotic. Only those plant cells/tissue that have DNA from the plasmid (the resistance gene) will have antibiotic resistance. The conditions therefore select for the plant cells/tissue by killing those that do not contain plasmid DNA. After resistant callus is selected, they are transferred to medium that induces growth of shoots, where they grow roots, and then to soil to grow into mature plants.

Plants (offspring) are then selected for those which have a mutation in the desired gene (e.g., such as those listed above). The selection process can look for altered size in the gene of interest and/or protein activity (protein normally produced by the gene of interest), as well as antibiotic resistance (an extra piece of DNA that was included in the plasmid inserted into the bacteria that provides for resistance to a specific antibiotic) or by sequence. Those plants with reduced to no activity in the desired gene (expression of RNA and/or protein), as compared to plants that were not exposed to the engineered nuclease (with identical starting backgrounds), are of particular interest. If the bacteria inserted any foreign DNA into the plant, these plants can be further bred until such DNA is no longer part of the mutated plant. The plants can also be bred so that they are homozygous for the mutation (e.g., deletion).

Also provided is a method crossing one or more first parent plants that contain a mutant allele at one or more loci of sec62, KCR2, DGAT1, FAX1, MIR394 and/or HAD (and optionally PDAT1 and/or ENR) and one or more second parent plants that contain a mutant allele at a different locus of sec62, KCR2, DGAT1, FAX1, MIR394 and/or HAD (and optionally PDAT1 and/or ENR), wherein each mutant allele results in the production of a polypeptide having reduced activity (or no activity) relative to a corresponding wild-type (or a gene that was not mutated as described herein) sec62, KCR2, DGAT1, FAX1, MIR394 and/or HAD (and optionally PDAT1 and/or ENR) polypeptide and/or sequence in the case of MIR394 (or no polypeptide is produced at all); and selecting progeny plants having mutants alleles at two or more different loci thereby obtaining a desired plant.

Plant Products

Oils obtained from such plants, such as *Brassica* plants (canola oil), can have low or no saturated fatty acids and an altered oleic acid content as compared to a plant that was not mutated as described herein (identical genetic background to plant prior to exposure to an engineered nuclease). Oil content in the seeds can be determined by methods known to those of skill in the art.

In another aspect, a method of producing an oil is provided. The method includes crushing seeds produced from at least one *Brassica* plant described herein; and extracting oil from the crushed seeds. Such oils can be used in food compositions, spray coatings for food, and/or for frying applications (such as frying food, so as to produce fried foods such as snack chips (e.g., corn or potato chips), French fries, or other quick serve foods).

The invention will be further described in the following examples, which do not limit the scope of the invention described in the claims.

EXAMPLES

Example 1

Mutation of Sec62 with Use of a Meganuclease

Using a meganuclease specific for sec62 (the expression of the desired meganuclease in a canola plant cell causes specific breaks in sec62 DNA in the plant genome; repair of which leads to deletions, insertions and/or base pair changes), several canola plants with deletions and/or additions in sec62 were generated (ranging from 1 to 350 base pair deletion and/or 1 to 100 base pair insertion; hetero- or homozygous for the mutation). This resulted in phenotypes with a decrease in C18:0 saturated fat production from about 11% to about 20%, with a reduction in total saturates from about 2% to about 9%, as compared to plants with an identical genetic background to the plant prior to exposure to an engineered nuclease.

Thus, targeted mutation of sec62 resulted in a significant and unexpected decrease in saturated fat production.

Example 2 sec62 Mutation and Analysis

In the Tables provided below, the fatty acids are referred to by the length of the carbon chain and number of double bonds within the chain. For example, C14:0 refers to myristic acid; C16:0 refers to palmitic acid; C18:0 refers to stearic acid; C18:1 refers to oleic acid; C18:2 refers to linoleic acid; C18:3 refers to ALA; C20:0 refers to archidic acid; C20:1 refers to eicosenoic acid; C22:0 refers to behenic acid; C22:1 refers to erucic acid; C24:0 refers to lignoceric acid; and C24:1 refers to nervonic acid. "Total Sats" refers to the total of C14:0, C16:0, C18:0, C20:0, C22:0, and C24:0. Representative fatty acid profiles are provided for each of the specified samples.

Unless otherwise indicated, all percentages refer to fatty acid % based on total fatty acids (i.e., fatty acid moieties) in the oil.

*Brassica* plants with lower saturated fatty acid were obtained by subjecting cells of *Brassica* plants to engineered meganucleases, followed by analysis of sequence (FIGS. 1A-1J) and saturated fatty acid production (Tables 1 and 2).

The average results of saturated fatty acid production in said mutant plant lines is presented in Table 1 (Cargill background; sec62 N13 and N15) and Table 2 (IMC201 background; sec62 N11), showing mutated plant lines, prepared by the methods described herein having a reduction of saturated fatty acid 18:0 (stearic acid) of about 16% to about 20%, a reduction in total saturated fatty acids of about 6% to about 9%. "Wild-Type" indicates average results for non-mutated (e.g., wild-type allele(s)) plants of the identical genetic background.

TABLE 1

| Sample | C18:0 | % reduction C18:0 | C20:0 | C22:0 | C24:0 | Total Sats 18/20/22/24 | % reduction 18/20/22/24 | Total Sats | % reduction total sats |
|---|---|---|---|---|---|---|---|---|---|
| sec62-N13 Mutant | 1.31 | 17% | 0.33 | 0.13 | 0.13 | 1.90 | 20% | 4.83 | 6% |
| sec62-N13/N15 Mutant | 1.33 | 16% | 0.32 | 0.12 | 0.11 | 1.88 | 20% | 4.74 | 8% |
| Wild-Type Cargill | 1.59 | | 0.42 | 0.19 | 0.16 | 2.36 | | 5.16 | |

TABLE 2

| Sample | C18:0 | % reduction C18:0 | C20:0 | C22:0 | C24:0 | Total Sats 18/20/22/24 | % reduction 18/20/22/24 | Total Sats | % reduction total sats |
|---|---|---|---|---|---|---|---|---|---|
| sec62-N11 Mutant | 2.26 | 20% | 0.68 | 0.32 | 0.14 | 3.40 | 19% | 7.71 | 9% |
| Wild-Type IMC201 | 2.82 | | 0.79 | 0.35 | 0.21 | 4.18 | | 8.49 | |

Example 3

Mutation of KCR2 with Use of a Meganuclease

Using a meganuclease specific for KCR2 (the expression of the desired meganuclease in a canola plant cell causes specific breaks in KCR2 DNA in the plant genome; repair of which leads to deletions, insertions and/or base pair changes), several canola plants with deletions and/or additions in KCR2 were generated (ranging from 1 to 350 base pair deletion and/or 1 to 100 base pair insertion; hetero- and/or homozygous for the mutation). This resulted in phenotypes with a decrease in C18:0 saturated fat production from about 15% to about 17%, with a reduction in total saturates from about 6% to about 7%, as compared to plants with an identical genetic background to the plant prior to exposure to an engineered nuclease.

Thus, targeted mutation of KCR2 resulted in a significant and unexpected decrease in saturated fat production.

Example 4

KCR2 Mutation and Analysis

Unless otherwise indicated, all percentages refer to fatty acid % based on total fatty acids (i.e., fatty acid moieties) in the oil.

*Brassica* plants with lower saturated fatty acid were obtained by subjecting cells of *Brassica* plants to engineered meganucleases, followed by analysis of sequence (FIGS. 2A-2P) and saturated fatty acid production (Table 3).

The average results of saturated fatty acid production in said mutant plant lines is presented in Table 3 (03LC LL and IMC201 backgrounds) showing mutated plant lines, prepared by the methods described herein having a reduction of saturated fatty acid 18:0 (stearic acid) of about 11% to about 17%, a reduction in total saturated fatty acids of about 1% to about 7%. "Wild-Type" indicates average results for non-mutated (e.g., wild-type allele(s)) plants of the identical genetic background.

TABLE 3

| Sample | C18:0 | % reduction 18:0 | C20:0 | C22:0 | C24:0 | Total Sats 18/20/22/24 | % reduction 18/20/22/24 | Total Sats | % reduction total sats |
|---|---|---|---|---|---|---|---|---|---|
| KCR2-N9 Mutant | 2.48 | 12% | 0.55 | 0.19 | 0.10 | 3.31 | 11% | 8.88 | 1% |
| KCR2-N15 Mutant | 2.52 | 11% | 0.56 | 0.20 | 0.10 | 3.37 | 9% | 8.75 | 2% |
| KCR2-N9/N15 Mutant | 2.44 | 14% | 0.55 | 0.19 | 0.11 | 3.29 | 11% | 8.89 | 1% |
| Wild-Type 03LC-LL | 2.83 | | 0.57 | 0.19 | 0.12 | 3.72 | | 8.94 | |
| KCR2-N7 Mutant | 2.40 | 15% | 0.73 | 0.34 | 0.16 | 3.63 | 13% | 7.95 | 6% |
| KCR2-N7/N17 Mutant | 2.34 | 17% | 0.72 | 0.34 | 0.17 | 3.56 | 15% | 7.88 | 7% |
| Wild-Type IMC201 | 2.82 | | 0.79 | 0.35 | 0.21 | 4.18 | | 8.49 | |

Example 5

Mutation of DGAT1 with Use of a Meganuclease

Using a meganuclease specific for DGAT1 (the expression of the desired meganuclease in a canola plant cell causes specific breaks in DGAT1 DNA in the plant genome; repair of which leads to deletions, insertions and/or base pair changes), several canola plants with deletions and/or additions in DGAT1 were generated (ranging from 1 to 350 base pair deletion and/or 1 to 100 base pair insertion; hetero- and/or homozygous for the mutation). This resulted in phenotypes with a decrease in C18:0 saturated fat production from about 20% to about 24%, with a reduction in total saturates from about 8% to about 90%, as compared to plants with an identical genetic background to the plant prior to exposure to an engineered nuclease.

Thus, targeted mutation of DGAT1 resulted in a significant and unexpected decrease in saturated fat production.

Example 6

DGAT1 Mutation and Analysis

Unless otherwise indicated, all percentages refer to fatty acid % based on total fatty acids (i.e., fatty acid moieties) in the oil.

*Brassica* plants with lower saturated fatty acid were obtained by subjecting cells of *Brassica* plants to engineered meganucleases, followed by analysis of sequence (FIGS. 3A-3G) and saturated fatty acid production (Table 4).

The average results of saturated fatty acid production in said mutant plant lines is presented in Table 4 (IMC201 background) showing mutated plant lines, prepared by the methods described herein having a reduction of saturated fatty acid 18:0 (stearic acid) of about 20% to about 24%, a reduction in total saturated fatty acids of about 8% to about 9%. "Wild-Type" indicates average results for non-mutated (e.g., wild-type allele(s)) plants of the identical genetic background.

TABLE 4

| Average Saturate Levels and Reductions | | | | | | | | | |
|---|---|---|---|---|---|---|---|---|---|
| Sample | C18:0 | % reduction C18:0 | C20:0 | C22:0 | C24:0 | Total Sats 18/20/22/24 | % reduction 18/20/22/24 | Total Sats | % reduction total sats |
| DGAT1-N9 Mutant | 2.14 | 24% | 0.65 | 0.30 | 0.22 | 3.30 | 21% | 7.70 | 9% |
| DGAT1-N19 Mutant | 2.25 | 20% | 0.67 | 0.31 | 0.21 | 3.43 | 18% | 7.77 | 8% |
| DGAT1-N9/N19 Mutant | 2.22 | 21% | 0.66 | 0.29 | 0.20 | 3.37 | 19% | 7.75 | 9% |
| Wild-Type IMC201 | 2.82 | | 0.79 | 0.35 | 0.21 | 4.18 | | 8.49 | |

Example 7

Mutation of FAX1 with Use of a Meganuclease

Using a meganuclease specific for FAX1 (the expression of the desired meganuclease in a canola plant cell causes specific breaks in FAX1 DNA in the plant genome; repair of which leads to deletions, insertions and/or base pair changes), several canola plants with deletions and/or additions in FAX1 were generated (ranging from 1 to 350 base pair deletion and/or 1 to 100 base pair insertion; hetero- and/or homozygous for the mutation). This resulted in phenotypes with a decrease in C18:0 saturated fat production from about 7% to about 18%, with a reduction in total saturates from about 2% to about 7%, as compared to plants with an identical genetic background to the plant prior to exposure to an engineered nuclease.

Thus, targeted mutation of FAX1 resulted in a significant and unexpected decrease in saturated fat production.

Example 8

FAX1 Mutation and Analysis

Unless otherwise indicated, all percentages refer to fatty acid % based on total fatty acids (i.e., fatty acid moieties) in the oil.

*Brassica* plants with lower saturated fatty acid were obtained by subjecting cells of *Brassica* plants to engineered meganucleases, followed by analysis of sequence (FIGS. 4A-4N) and saturated fatty acid production (Table 5).

The average results of saturated fatty acid production in said mutant plant lines is presented in Table 5 (IMC201 background) showing mutated plant lines, prepared by the methods described herein having a reduction of saturated fatty acid 18:0 (stearic acid) of about 13% to about 17%, a reduction in total saturated fatty acids of about 3% to about 6%. "Wild-Type" indicates average results for non-mutated (e.g., wild-type allele(s)) plants of the identical genetic background.

TABLE 5

| Sample | C18:0 | % reduction 18:0 | C20:0 | C22:0 | C24:0 | Total Sats 18/20/22/24 | % reduction 18/20/22/24 | Total Sats | % reduction total sats |
|---|---|---|---|---|---|---|---|---|---|
| FAX1-N9 Mutant | 2.33 | 17% | 0.71 | 0.32 | 0.15 | 3.50 | 16% | 8.00 | 6% |
| FAX1-N18 Mutant | 2.44 | 13% | 0.74 | 0.33 | 0.16 | 3.68 | 12% | 8.27 | 3% |
| FAX1-N9/N18 Mutant | 2.44 | 14% | 0.72 | 0.32 | 0.15 | 3.62 | 13% | 8.24 | 3% |
| FAX1-N9/N18/N7 Mutant | 2.42 | 14% | 0.68 | 0.29 | 0.12 | 3.51 | 16% | 7.95 | 6% |
| Wild-Type IMC201 | 2.82 | | 0.79 | 0.35 | 0.21 | 4.18 | | 8.49 | |

Example 9

Mutation of PDAT1 with Use of a Meganuclease

Using a meganuclease specific for phospholipid:diacylglycerol acyltransferase 1 (PDAT1) (the expression of the desired meganuclease in a canola plant cell causes specific breaks in PDAT1 DNA in the plant genome; repair of which leads to deletions, insertions and/or base pair changes), several canola plants with deletions and/or additions in PDAT1 were generated (ranging from 1 to 350 base pair deletion and/or 1 to 100 base pair insertion; hetero- and/or homozygous for the mutation). This resulted in phenotypes with a decrease in C18:0 saturated fat production from about 6% to about 15%, with a reduction in total saturates from about 2% to about 4%, as compared to plants with an identical genetic background to the plant prior to exposure to an engineered nuclease.

Thus, targeted mutation of PDAT1 resulted in a significant and unexpected decrease in saturated fat production.

Example 10

PDAT1 Mutation and Analysis

Unless otherwise indicated, all percentages refer to fatty acid % based on total fatty acids (i.e., fatty acid moieties) in the oil.

*Brassica* plants with lower saturated fatty acid were obtained by subjecting cells of *Brassica* plants to engineered meganucleases, followed by analysis of sequence (FIGS. 5A-5Q) and saturated fatty acid production (Table 6).

The average results of saturated fatty acid production in said mutant plant lines is presented in Table 6 (IMC201 background) showing mutated plant lines, prepared by the methods described herein having a reduction of saturated fatty acid 18:0 (stearic acid) of about 6% to about 15%, a reduction in total saturated fatty acids of about 2% to about 4%. "Wild-Type" indicates average results for non-mutated (e.g., wild-type allele(s)) plants of the identical genetic background.

TABLE 6

| Sample | C18:0 | % reduction 18:0 | C20:0 | C22:0 | C24:0 | Total Sats 18/20/22/24 | % reduction 18/20/22/24 | Total Sats | % reduction total sats |
|---|---|---|---|---|---|---|---|---|---|
| PDAT1-N10/N19 Mutant | 2.66 | 6% | 0.78 | 0.35 | 0.20 | 3.99 | 4% | 8.30 | 2% |
| PDAT1-N12/N10/N19 Mutant | 2.57 | 9% | 0.76 | 0.35 | 0.22 | 3.89 | 7% | 8.23 | 3% |
| PDAT1-N2/N10/N19 Mutant | 2.60 | 8% | 0.78 | 0.35 | 0.19 | 3.92 | 6% | 8.29 | 2% |
| PDAT1-N2/N12/N10/N19 Mutant | 2.41 | 15% | 0.71 | 0.33 | 0.21 | 3.66 | 12% | 8.16 | 4% |
| Wild-Type IMC201 | 2.82 | | 0.79 | 0.35 | 0.21 | 4.18 | | 8.49 | |

Example 11

Mutation of ENR with Use of a Meganuclease

Using a meganuclease specific for enoyl-acyl carrier protein reductase (ENR) (the expression of the desired meganuclease in a canola plant cell causes specific breaks in ENR DNA in the plant genome; repair of which leads to deletions, insertions and/or base pair changes), several canola plants with deletions and/or additions in ENR were generated (ranging from 1 to 400 base pair deletion and/or 1 to 100 base pair insertion; hetero- and/or homozygous for the mutation). This resulted in phenotypes with a decrease in C18:0 saturated fat production from about 9% to about 12%, with a reduction in total saturates from about 2% to about 4%, as compared to plants with an identical genetic background to the plant prior to exposure to an engineered nuclease.

Thus, targeted mutation of ENR resulted in a significant and unexpected decrease in saturated fat production.

Example 12

ENR Mutation and Analysis

Unless otherwise indicated, all percentages refer to fatty acid % based on total fatty acids (i.e., fatty acid moieties) in the oil.

*Brassica* plants with lower saturated fatty acid were obtained by subjecting cells of *Brassica* plants to engineered meganucleases, followed by analysis of sequence (FIGS. 6A-6J) and saturated fatty acid production (Table 7).

The average results of saturated fatty acid production in said mutant plant lines is presented in Table 7 (IMC201 background) showing mutated plant lines, prepared by the methods described herein having a reduction of saturated fatty acid 18:0 (stearic acid) of about 9% to about 12%, a reduction in total saturated fatty acids of about 2% to about 4%. "Wild-Type" indicates average results for non-mutated (e.g., wild-type allele(s)) plants of the identical genetic background.

TABLE 7

| Sample | C18:0 | % reduction 18:0 | C20:0 | C22:0 | C24:0 | Total Sats 18/20/22/24 | % reduction 18/20/22/24 | Total Sats | % reduction total sats |
|---|---|---|---|---|---|---|---|---|---|
| ENR-N7 Mutant | 2.47 | 12% | 0.77 | 0.37 | 0.23 | 3.84 | 8% | 8.19 | 4% |
| ENR-N3/N7 Mutant | 2.53 | 10% | 0.77 | 0.35 | 0.22 | 3.87 | 7% | 8.26 | 3% |
| ENR-N13/N7 Mutant | 2.50 | 11% | 0.75 | 0.35 | 0.20 | 3.80 | 9% | 8.28 | 2% |
| ENR-N3/N13/N7 Mutant | 2.58 | 9% | 0.78 | 0.36 | 0.22 | 3.93 | 6% | 8.25 | 3% |
| Wild-Type IMC201 | 2.82 | | 0.79 | 0.35 | 0.21 | 4.18 | | 8.49 | |

Example 13

Mutation of MIR394 with Use of a Meganuclease

Using a meganuclease specific for MIR394 (the expression of the desired meganuclease in a canola plant cell causes specific breaks in MIR394 DNA in the plant genome; repair of which leads to deletions, insertions and/or base pair changes), several canola plants with deletions and/or additions in MIR394 were generated (ranging from 1 to 350 base pair deletion and/or 1 to 100 base pair insertion; hetero- and/or homozygous for the mutation). This resulted in phenotypes with a decrease in C18:0 saturated fat production from about 15% to about 22%, with a reduction in total saturates of about 4%, as compared to plants with an identical genetic background to the plant prior to exposure to an engineered nuclease.

Thus, targeted mutation of MIR394 resulted in a significant and unexpected decrease in saturated fat production.

Example 14

MIR394 Mutation and Analysis

Unless otherwise indicated, all percentages refer to fatty acid % based on total fatty acids (i.e., fatty acid moieties) in the oil.

*Brassica* plants with lower saturated fatty acid were obtained by subjecting cells of *Brassica* plants to engineered meganucleases, followed by analysis of sequence (FIGS. 7A-7G) and saturated fatty acid production (Table 8).

The average results of saturated fatty acid production in said mutant plant lines is presented in Table 8 (Cargill background) showing mutated plant lines, prepared by the methods described herein having a reduction of saturated fatty acid 18:0 (stearic acid) of about 19%, a reduction in total saturated fatty acids of about 3% to about 6%. "Wild-Type" indicates average results for non-mutated (e.g., wild-type allele(s)) plants of the identical genetic background.

TABLE 8

| Sample | C18:0 | % reduction 18:0 | C20:0 | C22:0 | C24:0 | Total Sats 18/20/22/24 | % reduction 18/20/22/24 | Total Sats | % reduction total sats |
|---|---|---|---|---|---|---|---|---|---|
| MIR394-N16b Mutant | 1.23 | 19% | 0.32 | 0.15 | 0.12 | 1.82 | 17% | 5.10 | 6% |
| Wild-Type Cargill | 1.52 | | 0.38 | 0.17 | 0.13 | 2.19 | | 5.41 | |
| MIR394-N7c Mutant | 1.18 | 19% | 0.39 | 0.15 | 0.10 | 1.81 | 17% | 5.22 | 3% |
| Wild-Type Cargill | 1.45 | | 0.41 | 0.18 | 0.15 | 2.20 | | 5.36 | |

Example 15

Mutation of HAD with Use of a Meganuclease

Using a meganuclease specific for HAD (the expression of the desired meganuclease in a canola plant cell causes specific breaks in HAD DNA in the plant genome; repair of which leads to deletions, insertions and/or base pair changes), several canola plants with deletions and/or additions in HAD were generated (ranging from 1 to 350 base pair deletion and/or 1 to 100 base pair insertion; hetero- and/or homozygous for the mutation). This resulted in phenotypes with a decrease in C18:0 saturated fat production from about 16% to about 27%, with a reduction in total saturates of about 5% to about 12%, as compared to plants with an identical genetic background to the plant prior to exposure to an engineered nuclease.

Thus, targeted mutation of HAD resulted in a significant and unexpected decrease in saturated fat production.

Example 16

HAD Mutation and Analysis

Unless otherwise indicated, all percentages refer to fatty acid % based on total fatty acids (i.e., fatty acid moieties) in the oil.

*Brassica* plants with lower saturated fatty acid were obtained by subjecting cells of *Brassica* plants to engineered meganucleases, followed by analysis of sequence (FIGS. 8A-8G) and saturated fatty acid production (Table 9).

The average results of saturated fatty acid production in said mutant plant lines is presented in Table 9 (Cargill or IMC201 background) showing mutated plant lines, prepared by the methods described herein having a reduction of saturated fatty acid 18:0 (stearic acid) of about 20% to about 27%, a reduction in total saturated fatty acids of about 5% to about 12%. "Wild-Type" indicates average results for non-mutated (e.g., wild-type allele(s)) plants of the identical genetic background.

TABLE 9

| Sample | C18:0 | % reduction 18:0 | C20:0 | C22:0 | C24:0 | Total Sats 18/20/22/24 | % reduction 18/20/22/24 | Total Sats | % reduction total sats |
|---|---|---|---|---|---|---|---|---|---|
| HAD-N2 Mutant | 1.22 | 20% | 0.34 | 0.15 | 0.14 | 1.85 | 15% | 5.12 | 5% |
| Wild-Type Cargill | 1.52 | | 0.38 | 0.17 | 0.13 | 2.19 | | 5.41 | |
| HAD-N3 Mutant | 2.11 | 27% | 0.67 | 0.33 | 0.19 | 3.29 | 22% | 7.52 | 12% |
| Wild-Type IMC201 | 2.90 | | 0.78 | 0.33 | 0.19 | 4.19 | | 8.53 | |

Additional Embodiments

Some embodiments provide a method to mutate the genome of a *Brassica* plant cell at a target site comprising: a) inducing a double stranded DNA break at said target site, said double stranded break being induced by the introduction to said cell of a double stranded DNA break inducing (DSBI) enzyme which recognizes a recognition sequence in the vicinity of or at said target site in at least one of sec62, KCR2, DGAT1, FAX1, MIR394, HAD, PDAT1, and/or ENR sequences(s); and b) selecting a plant cell wherein said double stranded DNA break has been repaired resulting in a modification in the genome at said target site, wherein said modification is a substitution of at least one nucleotide, a deletion of at least one nucleotide, an insertion of at least one nucleotide or any combination thereof.

Other embodiments provide a method to produce a *Brassica* plant with reduced saturated fatty acids comprising: a) inducing a double stranded DNA break at a target site, said double stranded break being induced by the introduction to a plant cell of a double stranded DNA break inducing (DSBI) enzyme which recognizes a recognition sequence in the vicinity of or at said target site in at least one of sec62, KCR2, DGAT1, FAX1, MIR394, HAD, PDAT1, and/or ENR sequences(s); and b) selecting a plant cell wherein said double stranded DNA break has been repaired resulting in a mutation in the genome at said target site, wherein said mutation is a substitution of at least one nucleotide, a deletion of at least one nucleotide, an insertion of at least one nucleotide or any combination thereof; and c) regenerating said plant cell(s) of b) into a plant; wherein said mutation results in reduced production of saturated fatty acids by said plant as compared to a control plant of identical genetic background that has not been mutated by said DSBI and repair.

Several embodiments provide a mutated *Brassica* plant comprising a deletion or insertion in at least one allele of sec62, KCR2, DGAT1, FAX1, MIR394, HAD, PDAT1 and/or ENR.

BIBLIOGRAPHY

D'Halluin et al. 2013. Targeted molecular trait stacking in cotton through targeted double-strand break induction. Plant Biotech J 11:933-41.

Djukanovic et al. 2013. Male-sterile maize plants produced by targeted mutagenesis of the cytochrome P450-like gene (MS26) using a re-designed I-CreI homing endonuclease. The Plant Journal 76:888-99.

Gao et al. 2010. Heritable targeted mutagenesis in maize using a designed endonuclease. The Plant Journal 61:176-187.

Honig et al. 2015. Transient expression of virally delivered meganuclease in planta generates inherited genomic deletions. Mol Plant 8:1292-4.

Puchta & Fauser. 2014. Synthetic nucleases for genome engineering in plants: prospects for a bright future. The Plant Journal 78:727-741.

Sprink et al. 2015. Plant genome editing by novel tools: TALEN and other sequence specific nucleases. Current Opinion in Biotech 32:47-53.

Tzfira et al. 2012. Genome modifications in plant cells by custom-made restriction enzymes. Plant Biotech Journal 10:373-389.

All patents, patent applications, accession numbers and publications cited herein are incorporated herein by reference in their entirety.

What is claimed is:

1. A method to produce a *Brassica napus* plant with reduced saturated fatty acid content comprising:

a) inducing a double stranded DNA break at a target site, said double stranded break being induced by the introduction to a plant cell of a double stranded DNA break inducing (DSBI) enzyme which recognizes a recognition sequence in the vicinity of or at said target site in sec62, wherein sec62 comprises a nucleotide sequence of SEQ ID NOs: 2, 6, or 9; and b) selecting a plant cell wherein said double stranded DNA break has been repaired resulting in a mutation in the genome at said target site, wherein said mutation is i) a 9 bp deletion in sec62 sequence on chromosome N13 of SEQ ID NO: 3;

ii) a 9 bp insertion in sec62 sequence on chromosome N15 of SEQ ID NO: 7;

iii) a 4 bp deletion in sec62 sequence on chromosome N11 of SEQ ID NO: 10; or iv) any combination thereof; and c) regenerating said plant cell(s) of b) into a plant;

wherein said plant yields a reduction of stearic acid (18:0) of about 6% to about 27% as compared to a non-mutated plant of identical genetic background.

2. The method of claim 1, wherein the DSBI enzyme is a single chain meganuclease or a pair of meganucleases which recognizes or recognize in concert a site and induces or induce said double strand break.

3. The method of claim 1, wherein said plant is crossed with another plant.

4. A plant, plant part, seed or propagating material thereof comprising a mutation at a target site of the genome obtained by the method of claim 1.

5. The method of claim 1, wherein one or both sec62 alleles on N11, N13, and/or N15 are mutated.

6. The method of claim 1, wherein the plant yields a reduction of total saturated fatty acids by about 2% to about 12% as compared to a non-mutated plant of identical genetic background.

7. A mutated *Brassica napus* plant comprising a mutation in at least one allele of sec62, wherein said mutation is a) a 9 bp deletion in sec62 sequence on chromosome N13 of SEQ ID NO: 3;

b) a 9 bp insertion in sec62 sequence on chromosome N15 of SEQ ID NO: 7;

c) a 4 bp deletion in sec62 sequence on chromosome N11 of SEQ ID NO: 10; or d) any combination thereof, wherein the mutation results in a reduction of stearic acid (18:0) production of about 6% to about 27% in said plant as compared to a control plant of identical genetic background that does not have said deletion mutation.

* * * * *

SEQUENCE LISTING

```
<160> NUMBER OF SEQ ID NOS: 118

<210> SEQ ID NO 1
<211> LENGTH: 1740
<212> TYPE: DNA
<213> ORGANISM: Brassica napus

<400> SEQUENCE: 1

atgaagaagc ctgccggaac cgagaagaag agggttaaac gatcatccga tgctccacct      60

aaggttcgct ctcttctctc attgcttgct aaatcaattc caaataaaac ttgttctaag     120

gttacgtaac ccttgctttt gatctgcttc gctctctcat ggaacgatga ccctgcgatt     180

atatggaatt acagtccttg ttcgtcagac acatgtatat gttccttgtc tgaataatgt     240

caaacactgt tttgtttttg tttttgttag aagaaaggtg tgacgaagga tttgtttcag     300
```

ttgtttgctg agaaagttag agacaacaag gggttggaat caagatgggc tgttatggag 360
caagcgcgag tcgagtactt cagagggaaa gattttgtta gcttcgtgaa gaatcacccc 420
gagtgtaaag aggttcttga agaagatagt gacctcgacg ctgaagatat cgctaatgtg 480
ttgttgggga agaacctttt ggttagatgt gatcgtgtta ccaaaaccct tcgtcccggg 540
aagaaaaagc tctctacttg gcctgctcat cttgagattt tccgtgtaag ttggttcata 600
tgctaagagt atgattctat aacagagtgc ctgtgtttga cttgatagtt agcttctaaa 660
gactattgct attgaacatt ttgtctcatc ttagcttcaa gcccattcaa ttgcgcaaat 720
acattagcgt ttgatttgtt ttttgctgtt tctaatgcag gatgatcaag ctttctctga 780
aactgatgcg ttttttgcat ggacgtttga gaaacggcat ccactctggc aaacactttt 840
gtccttcttc tggcctgtat tgactctcgc gatctgtttg tttcctgtgt acccacaccg 900
ttgcaaactc attgttctct actcgtgtgc tggcattctt ttgatgattc tctccttgct 960
ttttggtaaa ctctgcatat gtaatatgtt tagtgtgctt tatttctcga gtgtgttgtt 1020
tcactctgat gacactctgt tattggctct taatctaggc gatgatttgc tggctatata 1080
tgcctaactt atccatgtct tggagactgg tggtgatatg tagttttaat ttggatttct 1140
tcttcattac cttgaatgtt gcagtgagag cagttgcttt tggtgctatg tggattcttt 1200
ttggaaagcg tgtatggttc ttccccaaca ttcttgcaga ggaagccaca ttgaaggaac 1260
tattccgttt ctggccaaag aaagacgagg aagaacctcc caagtggaca tctcgacttt 1320
tctacacagt tgtggccgtt gttgttgtca tgctgctcag gcgccacgct cctgatgagg 1380
ctgctcgtgc caggtatttt aacttaaacc aagataacaa taattgaagt gattccctct 1440
cctcaagaga agattgtttt ctctaagtgc tatatgagtt ctatggtgga cttgtgatga 1500
tttttttgtg catccaggta ccaaagaagg atgtcaaaca tcattgatga tgtccttgag 1560
tggtcaccga agctggcact ctctggttta atggagaatc agccacctgt gaacatcaca 1620
gaggcggcta acaactcctc agatgccgca ggtccagacc atactgaaga ggccgaccta 1680
gacgaaactc aaggcgagga ggaagctgaa gacttgacca actctgatat aaaaacataa 1740

<210> SEQ ID NO 2
<211> LENGTH: 309
<212> TYPE: DNA
<213> ORGANISM: Brassica napus

<400> SEQUENCE: 2
atgcaggatg atcaagcttt ctctgaaaca gatgcgtttt ttgcatggac gtttgagaaa 60
cggcacccac tctggcaaac acttttgtcc ttcttctggc ctgtattgac tctcgcgatc 120
tgtttgtttc ctgtgtaccc acaccgttgc aaactcattg ttctctactc gtgtgctggc 180
attcttttga tgattctctc cttgcttttt ggtaagctct gcatatgtaa tatgtttagt 240
gtgctttatt tctcgagtgt gttgtttcac tctgatgaca ctctgttttt ggctcttaat 300
ctaggcgat 309

<210> SEQ ID NO 3
<211> LENGTH: 300
<212> TYPE: DNA
<213> ORGANISM: Brassica napus

<400> SEQUENCE: 3
atgcaggatg atcaagcttt ctctgaaaca gatgcgtttt ttgcatggac gtttgagaaa 60

-continued

```
cggcacccac tctggcaaac acttttgtcc ttcttctggc ctgtattgac tctcgcgatc    120

tgtttgtacc cacaccgttg caaactcatt gttctctact cgtgtgctgg cattcttttg    180

atgattctct ccttgctttt tggtaagctc tgcatatgta atatgtttag tgtgctttat    240

ttctcgagtg tgttgtttca ctctgatgac actctgtttt tggctcttaa tctaggcgat    300


<210> SEQ ID NO 4
<211> LENGTH: 130
<212> TYPE: DNA
<213> ORGANISM: Brassica napus

<400> SEQUENCE: 4

aacacttttg tccttcttct ggcctgtatt gactctcgct atctgtttgt ttcctgtgta     60

cccacaccgt tgcaaactca ttgttctcta ctcgtgtgct ggcattcttt tgatgattct    120

ctctttgctt                                                            130


<210> SEQ ID NO 5
<211> LENGTH: 121
<212> TYPE: DNA
<213> ORGANISM: Brassica napus

<400> SEQUENCE: 5

aacacttttg tccttcttct ggcctgtatt gactctcgcg atctgtttgt acccacaccg     60

ttgcaaactc attgttctct actcgtgtgc tggcattctt ttgatgattc tctccttgct    120

t                                                                     121


<210> SEQ ID NO 6
<211> LENGTH: 300
<212> TYPE: DNA
<213> ORGANISM: Brassica napus

<400> SEQUENCE: 6

atccactgtg gcaaacgctt ttgtccttct tctggcctgt attgactctc gctatttgtt     60

tgtttcctgt gtacccacac cgttgcaaac tcattgttct ctactcatgt gctggcattc    120

ttttgatgat tctctccttg cttttcggta agctctacat atattaacct gcttaaagta    180

ggtttatatt ggcttatgtt ttttcttgat taccgtggat gttgcagtga gagcagttgc    240

tttcggtgcg atgtggattc ttcttggaaa gcgtgtctgg ttcttcccca acattcttgc    300


<210> SEQ ID NO 7
<211> LENGTH: 309
<212> TYPE: DNA
<213> ORGANISM: Brassica napus

<400> SEQUENCE: 7

atccactgtg gcaaacgctt ttgtccttct tctggcctgt attgactctc gctatttgtt     60

tgtttcctgt gtacatattg tacccacacc gttgcaaact cattgttctc tactcatgtg    120

ctggcattct tttgatgatt ctctccttgc ttttcggtaa gctctacata tattaacctg    180

cttaaagtag gtttatattg gcttatgttt ttttcttgatt accgtggatg ttgcagtgag    240

agcagttgct ttcggtgcga tgtggattct tcttggaaag cgtgtctggt tcttccccaa    300

cattcttgc                                                             309


<210> SEQ ID NO 8
<211> LENGTH: 129
<212> TYPE: DNA
<213> ORGANISM: Brassica napus
```

<400> SEQUENCE: 8
acgcttttgt ccttcttctg gcctgtattg actctcgcta tttgtttgtt tcctgtgtac 60
ccacaccgtt gcaaactcat tgttctctac tcatgtgctg gcattctttt gatgattctc 120
tccttgctt 129

<210> SEQ ID NO 9
<211> LENGTH: 200
<212> TYPE: DNA
<213> ORGANISM: Brassica napus

<400> SEQUENCE: 9
atggagcaag cgcgtgtcga atacttcaga ggcaaagatt tcgtcagctt cattaagaat 60
caccccgagt gtaaagagat tctcgaagaa gataaagacc tcgacactga agatatcgcc 120
aatgtgttgt tggagaagaa ccttttggtc cgatgtgatc gtgtgactaa aacccttcgt 180
cccgggaaga aaaagctctc 200

<210> SEQ ID NO 10
<211> LENGTH: 196
<212> TYPE: DNA
<213> ORGANISM: Brassica napus

<400> SEQUENCE: 10
atggagcaag cgcgtgtcga atacttcaga ggcaaagatt tcgtcagctt cattaagaat 60
caccccgtaa agagattctc gaagaagata aagacctcga cactgaagat atcgccaatg 120
tgttgttgga gaagaacctt ttggtccgat gtgatcgtgt gactaaaacc cttcgtcccg 180
ggaagaaaaa gctctc 196

<210> SEQ ID NO 11
<211> LENGTH: 127
<212> TYPE: DNA
<213> ORGANISM: Brassica napus

<400> SEQUENCE: 11
agaggcaaag atttcgtcag cttcattaag aatcaccccg agtgtaaaga gattctcgaa 60
gaagataaag acctcgacac tgaagatatc gccaatgtgt tgttggagaa gaaccttttg 120
gtccgat 127

<210> SEQ ID NO 12
<211> LENGTH: 121
<212> TYPE: DNA
<213> ORGANISM: Brassica napus

<400> SEQUENCE: 12
agaggcaaag atttcgtcag cttcattaag aatcacccgt aaagagattc tcgaagaaga 60
taaagacctc gacactgaag atatcgccaa tgtgttgttg gagaagaacc ttttggtcga 120
t 121

<210> SEQ ID NO 13
<211> LENGTH: 3253
<212> TYPE: DNA
<213> ORGANISM: Brassica napus

<400> SEQUENCE: 13
atgcaaagaa catggcatca tatctccatg tcgtaagctt cataggtttt ctctctatcc 60

```
ttagattact ctatcctctc ctgaaatggt tcatcacgag attcctcctc actgacccca    120

ggcgactcaa gagttatggc tcgtgggcta tggtcactgg agccacagat gggatcggac    180

aagcctttgc tcacgagctg gcaaaacacg gccttaacct cgtcctagtc agcagaaacc    240

cttcgaagct agcttctgtc tccgatgatt tcagacaaga atttccccaa atcaagatca    300

agatcattcc ctttgacttc tcctctggta atactaaatg cactttctta tttttcaatg    360

cagtcttcac ttcacttttg gtcaatccta tagaactagg cgtctatatg tctctgtgtg    420

agcataacta cagggctgta aacttggaaa atatattctt gtttcaacag ctagccagga    480

tgaaaacaca caattattca atccaaatgc aaaatgaacc gagttaatat agtatacaat    540

tactctagaa tgcaagatcc actttaattt gttatagtat aacgttacta actaatacat    600

gcatttacaa gattaaacta aagatcaaat gctttcttaa atattttttt gttagttttt    660

gtatatttat tattttaggg ggccgggtaa acttctaagc tatttcagtc tacaaagatg    720

atacgcatgc aaaactaaag atggtggcag atgtaatata gaaatgaagg gtgttgtatt    780

tatgagcagt gataaattgg agaaatgtgc agaaagagga tatgaagcaa tcgaggaggg    840

aatcagaggc cttgaagttg gaattctgat aaacaacgtt ggtataactt atccacgagc    900

catgttcttc cacgaggttg acgaactcac atggaccaaa atccttaggg ttaatcttga    960

agccaccact tgggtcacaa gatctctcat cggaccaatg cttcaccgcc gtcgaggagc   1020

tatcataaat attagctccg gcgccgcagt tgttgtccct tcgcatccac tctatgccat   1080

ctacgccgcc accaaagcgt taggacttta actttctttt tatttactgc ttctaaagtt   1140

caatgcacat tttataaata taagcatact aaccaacaaa attagaagaa aactagagag   1200

atcttaagaa taatattaga tgggagtaag aaaaagattc acaagatatc ttatgtcatt   1260

taacacagaa gttaatctct aaccaagata aagtagtaat ttagaaaact aaactttggt   1320

tgtaattagc tctaactaaa agtctaaaag atctgaactt aaagttagtt acttagctca   1380

attataagtt tgtagttatt taaaatctca tatatattaa aagagaaaca ttacaacatt   1440

ttaactatga catgtcatca ttagaatgct ttttaaaatt tctaaaaaaa tatgttggtc   1500

cactaatcat atattatata tacttctcct taaactaacc atgaaattaa ttaacaatta   1560

acaattacta ttatttttct taaataacta cgaaattacc aaaagtgaat aaaatatata   1620

tttgacagtt aatgatttca ataaaaaaaa tttgacaaca atttacatat cttcattatt   1680

atataatgtt atattattaa aataaattaa ataattacat taaccatata ataaaaaatt   1740

agatttttttc gtatgtgtta tattttgaat tttaaaaagg actataaata acaaaaatcg   1800

ttaaaagtct catattggaa attttatgat ctatagttta atttttttgt tttaataaaa   1860

tacaaatgat cgtaaaacca tacaagtaaa aatcacattt attagatatt gagattaata   1920

tatatatagg acttatgaat gatataatta tggttgaacg gtcaaagttc gtattcaata   1980

attattagaa tatactccct ccgttcctaa aagatgcatg ttctggaaaa aaaatttgtt   2040

tcaaaaagat atatttttta ctttttcaat gtatgatttt atgaaaaatt gtaagtttca   2100

aaaaaattaa tggtgtttat tgaattttta ttggctaaaa gttatcgaaa attgttattt   2160

acaaaaaaca atgcatattt aatgagtttt cttaatatat gtgaaaagtc tagaatatgc   2220

atcttttaaa aacagaggga gtatatttca ttcttagtat gtgcgcgaat tcatgcatta   2280

tattggaatc ttaaattcta tttattttaa actgaaaact actagtagta caaagttctg   2340

tttcttttca aattactaac tacagctata tcggtgactt gcatgtagtc attaaggttt   2400

cggtccgttc tttctattta attttttggt agttattagt tgttgtataa taaattgtgt   2460
```

aatcgactct atacacgtag atgtatatag gtaacccacc cacatgtaag acccgtgcat 2520
ttacgacctt ttagctaggt ggattgttaa agtaattatg atgaatcatc acgcgacaaa 2580
accttgttct agttacttag atagagtgtt gttatttgta aaaataacaa ctataagtaa 2640
cgcttttact ttgatagcat catagcaata gagcgatcat ttcatttgac catatataag 2700
ttgttaaaaa tgtcttcggt gattaggaaa agctaattgt cattttgtaa aatgtataaa 2760
ctaattgtca ttttattcat atcgttttat tgatagaaca aaatgtcagc tgttttatga 2820
attttatgca tattgtccat aaccatcaca tgcatgaatt aacgaatacg tgcatgcagt 2880
tatgttgata aactatcaag atctttgcat gtggaatata agcagtttgg tatccacgtc 2940
caatgccagg taactttttg ttttcttttt cttttctcta taatacttta tgatttccca 3000
tgtaatgtgg caggtgccgt tatatgtggc aacgaggatg gtgtcagaag tagcagatat 3060
agataaacca agcttctttg taccatcgcc ggaagtatat gcaaaagcgg cggtggagca 3120
gatcggaatt ggatcacgat gctctccatt ttgggctcat tcacttcagt ggtttctcgc 3180
tggtcttttg ccggagaacc ttcttgatac ttggcgtctc tctatcggtc ttcgtagaag 3240
aagcttgtct tag 3253

<210> SEQ ID NO 14
<211> LENGTH: 258
<212> TYPE: DNA
<213> ORGANISM: Brassica napus

<400> SEQUENCE: 14
gcagtgataa attggagaaa tgtgcagaaa gaggatatga agcaatcgag gagggaatca 60
gaggccttga agttggaatt ctgataaaca acgttggtat aacttatcca cgagccatgt 120
tcttccacga ggttgacgaa ctcacatgga ccaaaatcct tagggttaat cttgaagcca 180
ccacttgggt cacaagatct ctcatcggac caatgcttca ccgccgtcga ggagctatca 240
taaatattag ctccggcg 258

<210> SEQ ID NO 15
<211> LENGTH: 234
<212> TYPE: DNA
<213> ORGANISM: Brassica napus

<400> SEQUENCE: 15
gcagtgataa attggagaaa tgtgcagaaa gaggatatga agcaatcgag gagggaatca 60
gaggccttga agttggaatt catccacgag ccatgttctt ccacgaggtt gacgaactca 120
catggaccaa aatccttagg gttaatcttg aagccaccac ttgggtcaca agatctctca 180
tcggaccaat gcttcaccgc cgtcgaggag ctatcataaa tattagctcc ggcg 234

<210> SEQ ID NO 16
<211> LENGTH: 94
<212> TYPE: DNA
<213> ORGANISM: Brassica napus

<400> SEQUENCE: 16
agggaatcag aggccttgaa gttggaattc tgataaacaa cgttggtata acttatccac 60
gagccatgtt cttccacgag gttgacgaac tcac 94

<210> SEQ ID NO 17
<211> LENGTH: 70
<212> TYPE: DNA

<213> ORGANISM: Brassica napus

<400> SEQUENCE: 17
agggaatcag aggccttgaa gttggaattc atccacgagc catgttcttc cacgaggttg 60
acgaactcac 70

<210> SEQ ID NO 18
<211> LENGTH: 258
<212> TYPE: DNA
<213> ORGANISM: Brassica napus

<400> SEQUENCE: 18
gcagtgataa attggagaaa tgtgcagaaa gaggatatga agcaatcgag gagggaatca 60
aaggcctcga agttggaatt ctgataaaca acgttggtat aacttatcca cgagccatgt 120
tcttccacga ggttgaccaa ctcacatgga ccaaaatcct tagggttaat cttgaagcca 180
ccacctgggt cacaagatct ctcatcggac caatgcttca ccgccgtcga ggagctatca 240
taaatattag ctccggcg 258

<210> SEQ ID NO 19
<211> LENGTH: 245
<212> TYPE: DNA
<213> ORGANISM: Brassica napus

<400> SEQUENCE: 19
gcagtgataa attggagaaa tgtgcagaaa gaggatatga agcaatcgag gagggaatca 60
aaggcctcga agttggaatt ctgatataaa ttatccacga gccatgttct tccacgaggt 120
tgaccaactc acatggacca aaatccttag ggttaatctt gaagccacca cctgggtcac 180
aagatctctc atcggaccaa tgcttcaccg ccgtcgaaga gctatcataa atattagctc 240
cggcg 245

<210> SEQ ID NO 20
<211> LENGTH: 94
<212> TYPE: DNA
<213> ORGANISM: Brassica napus

<400> SEQUENCE: 20
agggaatcaa aggcctcgaa gttggaattc tgataaacaa cgttggtata acttatccac 60
gagccatgtt cttccacgag gttgaccaac tcac 94

<210> SEQ ID NO 21
<211> LENGTH: 81
<212> TYPE: DNA
<213> ORGANISM: Brassica napus

<400> SEQUENCE: 21
agggaatcaa aggcctcgaa gttggaattc tgatataact tatccacgag ccatgttctt 60
ccacgaggtt gaccaactca c 81

<210> SEQ ID NO 22
<211> LENGTH: 389
<212> TYPE: DNA
<213> ORGANISM: Brassica napus

<400> SEQUENCE: 22
taggctttct ttctctcgtt agactattcc tccctctcct aaaatggttc atcacgagat 60
tcctactcac aaaccctaag cggctcaagc gttatggctc gtgggctatg gtcactggag 120

```
ccacagatgg aatcggacta gccttcgctc acgagctagc aaaacacggc ctcaacctta    180

tcctagtcag cagaaaccct ttgaagctcg cctccgtctc cgatgatttc cgacaagagt    240

ttccacaaat aaagatcaag atcattccct ttgacttctc ctctggtaat tctaaatgca    300

ctttcttact ttttcaatgc agtctggcct cacttcttct tcggccaatc gtattgagct    360

agttcacaaa gagttatcga ctactcgtt                                      389
```

```
<210> SEQ ID NO 23
<211> LENGTH: 390
<212> TYPE: DNA
<213> ORGANISM: Brassica napus

<400> SEQUENCE: 23

taggctttct ttctctcgtt agactattcc ttcctctcct aaaatggttc atcacgagat     60

tcctactcac aaaccctaag cggctcaagc gttatggctc gtgggctatg gtcactggag    120

ccacagatgg aatcggacga gccttcgctc acgagctagc aaaaacacgg cctcaacctt    180

atcctaatca gcagaaaccc tttgaagctc gcctccgtct ccgatgattt ccgacaagag    240

tttccacaaa tcaagatcaa gatcattccc tttgacttct cctctggtaa ttctaaatgc    300

actttcttac tttttcaatg cagtctggtc tcacttcttc ttcggccaat cgtattgagc    360

tagttcacac agagttatcg actactcgtt                                     390
```

```
<210> SEQ ID NO 24
<211> LENGTH: 94
<212> TYPE: DNA
<213> ORGANISM: Brassica napus

<400> SEQUENCE: 24

tggtcactgg agccacagat ggaatcggac tagccttcgc tcacgagcta gcaaaacacg     60

gcctcaacct tatcctagtc agcagaaacc cttt                                 94
```

```
<210> SEQ ID NO 25
<211> LENGTH: 95
<212> TYPE: DNA
<213> ORGANISM: Brassica napus

<400> SEQUENCE: 25

tggtcactgg agccacagat ggaatcggac tagccttcgc tcacgagcta gcaaaaacac     60

ggcctcaacc ttatcctagt cagcagaaac ccttt                                95
```

```
<210> SEQ ID NO 26
<211> LENGTH: 400
<212> TYPE: DNA
<213> ORGANISM: Brassica napus

<400> SEQUENCE: 26

taggctttct ttctctcgtt agactattcc tccctctcct aaaatggttc atcacgagat     60

tcctactcac aaaccctaag cggctcaagc gttatggctc gtgggctatg gtcactggag    120

ccacagatgg aatcggacta gccttcgctc acgagctagc aaaacacggc ctcaacctta    180

tcctagtcag cagaaaccct ttgaagctcg cctccgtctc cgatgatttc cgacaagagt    240

ttccacaaat aaagatcaag atcattccct ttgacttctc ctctggtaat tctaaatgca    300

ctttcttact ttttcaatgc agtctggcct cacttcttct tcggccaatc gtattgagct    360

agttcacaaa gagttatcga ctactcgttt gtgtgtgtgt                          400
```

<210> SEQ ID NO 27
<211> LENGTH: 385
<212> TYPE: DNA
<213> ORGANISM: Brassica napus

<400> SEQUENCE: 27
taggctttct ttctctcgtt agactattcc ttcctctcct aaaatggttc atcacgagat 60
tcctactcac aaaccctaag cggctcaagc gttatggctc gtgggctatg gtcactggag 120
ccacagatgg aatcggacga gccttcgctc acggcctcaa ccttatccta atcagcagaa 180
accctttgaa gctcgcctcc gtctccgatg atttccgaca agagtttcca caaatcaaga 240
tcaagatcat tccctttgac ttctcctctg gtaattctaa atgcactttc ttactttttc 300
aatgcagtct ggtctcactt cttcttcggc caatcgtatt gagctagttc acacagagtt 360
atcgactact cgtttgtgtg tgtgt 385

<210> SEQ ID NO 28
<211> LENGTH: 94
<212> TYPE: DNA
<213> ORGANISM: Brassica napus

<400> SEQUENCE: 28
tggtcactgg agccacagat ggaatcggac tagccttcgc tcacgagcta gcaaaacacg 60
gcctcaacct tatcctagtc agcagaaacc cttt 94

<210> SEQ ID NO 29
<211> LENGTH: 79
<212> TYPE: DNA
<213> ORGANISM: Brassica napus

<400> SEQUENCE: 29
tggtcactgg agccacagat ggaatcggac gagccttcgc tcacggcctc aaccttatcc 60
taatcagcag aaacccttt 79

<210> SEQ ID NO 30
<211> LENGTH: 576
<212> TYPE: DNA
<213> ORGANISM: Brassica napus

<400> SEQUENCE: 30
taggctttct ttctctcgtt agactattct ttcctctcct gaaatggttc atcacgagat 60
tcctactcac aaaccctaag cggctcaaac gttatggctc gtggactatg gtcactggag 120
ccacagatgg aatcggacga gcctttgctc acgagctagc aaaacacggc cttaacctca 180
tcctagtcag cagaaaccct tcgaagctcg cttccgtctc cgatgatttc cgacaagagt 240
ttccacaaat taagatcaag atcattcctt ttgactgctc tggtaattct aaatgcactt 300
tcttactttt tcatttcagt gctcacttct ttttcggcca atcgtcttga gctagtccac 360
acagagttct cgactactcg tttgtgtgtg tgctcacgca tataattact acatgattgt 420
aacattggaa aaattattgt tctttctcaa aagaaaaatc ttgattcaac agccaggata 480
aaaaatataa ttactccgca caaataattc gaaacataaa tgaatatata gagtacacaa 540
ttacatttag tagtgtattt gtaagagagc cgcaaa 576

<210> SEQ ID NO 31
<211> LENGTH: 577
<212> TYPE: DNA
<213> ORGANISM: Brassica napus

<400> SEQUENCE: 31
taggctttct ttctctcgtt agactattct ttcctctcct gaaatggttc atcacgagat 60
tcctactcac aaaccctaag cggctcaaac gttatggctc gtggactatg gtcactggag 120
ccacagatgg aatcggacga gcctttgctc acgagctagc aaaaacacgg ccttaacctc 180
atcctagtca gcagaaaccc ttcgaagctc gcttccgtct ccgatgattt ccgacaagag 240
tttccacaaa ttaagatcaa gatcattcct tttgactgct ctggtaattc taaatgcact 300
ttcttacttt ttcatttcag tgctcacttc tttttcggcc aatcgtcttg agctagtcca 360
cacagagttc tcgactactc gtttgtgtgt gtgctcacgc atataattac tacatgattg 420
taacattgga aaaattattg ttctttctca aaagaaaaat cttgattcaa cagccaggat 480
aaaaaatata attactccgc acaaataatt cgaaacataa atgaatatat agagtacaca 540
attacattta gtagtgtatt tgtaagagag ccgcaaa 577

<210> SEQ ID NO 32
<211> LENGTH: 93
<212> TYPE: DNA
<213> ORGANISM: Brassica napus

<400> SEQUENCE: 32
tggtcactgg agccacagat ggaatcggac gagctttgct cacgagctag caaaacacgg 60
ccttaacctc atcctagtca gcagaaaccc ttc 93

<210> SEQ ID NO 33
<211> LENGTH: 94
<212> TYPE: DNA
<213> ORGANISM: Brassica napus

<400> SEQUENCE: 33
tggtcactgg agccacagat ggaatcggac gagctttgct cacgagctag caaaaacacg 60
gccttaacct catcctagtc agcagaaacc cttc 94

<210> SEQ ID NO 34
<211> LENGTH: 2690
<212> TYPE: DNA
<213> ORGANISM: Brassica napus

<400> SEQUENCE: 34
atggagattt tggattctgg aggcgtcact atgccgacgg agaacggtgg tgccgatctc 60
gatacgcttc gtcaccggaa accgagatcg gattcttcca atggacttct tcctgattcc 120
gtaactgttt ccgatgctga cgtgagggat cgggttgatt cagctgttga ggatactcaa 180
ggaaaagcca atttggccgg agaaaacgaa attagggaat ccggtggaga agcgggggga 240
aacgtggatg taaggtacac gtatcggccg tcggttccag ctcatcggag ggtgagggag 300
agtccactca gctctgacgc catcttcaaa caggtaatca atcttagagg agaatttcaa 360
attgacttct tatcttcttg acttgcatat ttaaagatta tatttttttt tttatttgag 420
taatgtgatt gttttcatca tggcagagcc atgctggact attcaacctg tgtgtagtag 480
ttcttgttgc tgtaaacagt agactcatca tcgaaaatct catgaaggtt tgttacttac 540
ttctttctcc tcttccttca aacttatgag accttacatt tgttcattca tgtagtacgg 600
ttggttgatc agaactgatt tctggtttag ttcaacgtct ctgcgagatt ggccccttt 660 catgtgttgg tacaaatgct tcttctttct ttgtacatat ggtgattcag attttttcaa 720

```
gtttttgaac tttatgtggc agtctctccc tttcaatctt tcctttggct gcctttaccg    780

tcgagaaatt agtacttcag aaatgcatat ctgaacctgt gagtaaactg ctgtctatcc    840

tttacagggt tgttcgttga acgacaaatt tttatcctga acaacttata agtttctttc    900

tgtaggttgt catcattctt catattatta tcaccatgac cgaggtcttg tatccagtct    960

atgtcactct aaggtgagat ttaagcttgt gatactcttt tttttgttaa agttttgttt   1020

gctgactaga tgatcttgaa aacggacagg tgtgattccg ccttcttatc aggtgtcacg   1080

ttgatgctcc tcacttgcat tgtgtggctg aagttggttt cttacgctca tactaactat   1140

gacataagaa ccctagctaa ttcatctgat aaggtaaaag aagtgatata atattggtca   1200

cttgcattgt gttttactat tttgaccaga cactgttgaa aactgtaggc caatcctgaa   1260

gtctcctact atgttagctt gaagagcttg gcgtatttca tgcttgctcc cacattgtgt   1320

tatcaggtaa tctgatgcgt cttctgctaa ttgtatcata cattatcttt cacttgcaaa   1380

agtttcttgt ctaaaacctt gcgtcttcgc tttacccagc cgagctatcc acgttctcca   1440

tgtatccgga agggttgggt ggctcgtcaa tttgcaaagc tgatcatatt cactggattc   1500

atgggattta taatagagca agtgcgtttt taacctttcc ttgtgaaaat catcatttct   1560

gcattgttac ccgcttaact tcatgttctt ttggtacttc tttgttgcag tatataaatc   1620

ctattgttag gaactcaaaa catcctttga aaggggatct cttatacggt gttgaaagag   1680

tgttgaagct ttcagttcca aatttatacg tgtggctctg catgttctac tgcttcttcc   1740

acctttggta tgccgccatc ccatcacatg attaatttag tttctcagag actgagatgt   1800

aatgtcagtt tctgatcata aaccacgttg cactgttctt gtccacaggt taaacatatt   1860

ggcagagctc ctctgcttcg gggatcgtga attctacaaa gattggtgga atgcaaaaag   1920

cgtgggagat gtgagttttc atcaatcttg tcttactcaa aaatcatatt atgtttacgt   1980

tactaaccaa aattcatgta cgcactgtct acctttgtca gtattggaga atgtggaata   2040

tggtatggtt ctcttcttga aacatcccct tcttttttta tacaaagcag attaagaaaa   2100

gcttattgag atcttgtttt ttctaatagc ctgttcataa atggatggtt cgacatgtat   2160

actttccgtg ccttcgcaga aatataccga aagtgagtgt agttaattgc gatgatcgat   2220

attttttct gtgcttcata aatttaaccc tccactcatt tttttccagg tacccgctat   2280

tatccttgct ttcttagtct ctgcagtctt tcatgaggta taatacatac cttccacatt   2340

aaccctggct ctagctattg aaataaaggc taacactcaa aagtattgtt cttacttata   2400

ttctcgtgtg ttacaaattt ccttgcagtt atgcatcgca gttccttgtc gtctcttcaa   2460

actatgggct ttcttgggga ttatgtttca ggtataaaag aattaacaaa gtttccgcag   2520

tcagttctca caaacaatct tcaagcttct gtcaccttta gttacatttt ctgatcatgc   2580

aatgtgtgtt tgagtaggtg cctttggtat ttatcacaaa ctacctacaa gaaaggtttg   2640

gctccatggt atgctctcta aactggaaaa gtaactcttt tgttttctga              2690
```

```
<210> SEQ ID NO 35
<211> LENGTH: 341
<212> TYPE: PRT
<213> ORGANISM: Brassica napus

<400> SEQUENCE: 35

Gly Thr Thr Ala Gly Gly Ala Ala Cys Thr Cys Ala Ala Ala Gly Cys
1               5                   10                  15

Ala Thr Cys Cys Thr Cys Thr Gly Ala Ala Ala Gly Gly Gly Gly Ala
            20                  25                  30
```

```
Cys Cys Thr Thr Cys Thr Ala Thr Ala Thr Gly Cys Thr Ala Thr Thr
        35                  40                  45

Gly Ala Ala Ala Gly Ala Gly Thr Gly Thr Thr Gly Ala Ala Gly Cys
    50                  55                  60

Thr Thr Thr Cys Ala Gly Thr Thr Cys Cys Ala Ala Ala Thr Cys Thr
65                  70                  75                  80

Ala Thr Ala Thr Gly Thr Gly Thr Gly Gly Cys Thr Cys Thr Gly Cys
                85                  90                  95

Ala Thr Gly Thr Thr Cys Thr Ala Cys Thr Gly Cys Thr Thr Cys Thr
            100                 105                 110

Thr Cys Cys Ala Cys Cys Thr Thr Thr Gly Gly Thr Ala Thr Gly Cys
        115                 120                 125

Cys Ala Thr Gly Ala Thr Cys Cys Cys Gly Thr Cys Thr Cys Thr Thr
    130                 135                 140

Thr Cys Ala Ala Cys Ala Thr Gly Ala Thr Cys Thr Ala Thr Ala Ala
145                 150                 155                 160

Ala Gly Ala Thr Gly Ala Ala Cys Ala Ala Cys Ala Ala Gly Ala Gly
                165                 170                 175

Ala Ala Ala Gly Gly Ala Gly Ala Ala Thr Ala Thr Cys Thr Cys Ala
            180                 185                 190

Thr Gly Ala Ala Gly Ala Ala Ala Thr Thr Gly Ala Thr Gly Ala Thr
        195                 200                 205

Ala Thr Thr Ala Gly Thr Thr Thr Thr Thr Thr Thr Cys Ala Cys Ala
    210                 215                 220

Gly Thr Thr Thr Gly Ala Gly Ala Thr Gly Thr Ala Ala Thr Thr Thr
225                 230                 235                 240

Cys Ala Gly Thr Thr Thr Cys Thr Gly Ala Cys Cys Ala Ala Ala Thr
                245                 250                 255

Cys Thr Cys Thr Thr Thr Gly Cys Ala Thr Thr Gly Thr Thr Cys Thr
            260                 265                 270

Thr Gly Thr Thr Cys Ala Ala Ala Gly Gly Thr Thr Ala Ala Ala Cys
        275                 280                 285

Ala Thr Ala Cys Thr Gly Gly Cys Ala Gly Ala Gly Cys Thr Gly Cys
    290                 295                 300

Thr Cys Thr Gly Cys Thr Thr Cys Gly Gly Gly Gly Ala Cys Cys Gly
305                 310                 315                 320

Thr Gly Ala Ala Thr Thr Cys Thr Ala Cys Ala Ala Ala Gly Ala Thr
                325                 330                 335

Thr Gly Gly Thr Gly
            340
```

```
<210> SEQ ID NO 36
<211> LENGTH: 336
<212> TYPE: DNA
<213> ORGANISM: Brassica napus

<400> SEQUENCE: 36

gttaggaact caaagcatcc tctgaaaggg gaccttctat atgctattga aagagtgttg      60

aagctttcag ttccaaatct atatgtgtgg ctctgcatac tgcttcttcc acctttggta     120

tgccatgatc ccgtctcttt caacatgatc tataaagatg aacaacaaga gaaaggagaa     180

tatctcatga agaaattgat gatattagtt tttttcacag tttgagatgt aatttcagtt     240

tctgaccaaa tctctttgca ttgttcttgt tcaaaggtta aacatactgg cagagctgct     300
```

-continued ctgcttcggg gaccgtgaat tctacaaaga ttggtg 336

<210> SEQ ID NO 37
<211> LENGTH: 84
<212> TYPE: DNA
<213> ORGANISM: Brassica napus

<400> SEQUENCE: 37
tatatgtgtg gctctgcatg ttctactgct tcttccacct ttggtatgcc atgatcccgt 60
ctctttcaac atgatctata aaga 84

<210> SEQ ID NO 38
<211> LENGTH: 79
<212> TYPE: DNA
<213> ORGANISM: Brassica napus

<400> SEQUENCE: 38
tatatgtgtg gctctgcata ctgcttcttc cacctttggt atgccatgat cccgtctctt 60
tcaacatgat ctataaaga 79

<210> SEQ ID NO 39
<211> LENGTH: 536
<212> TYPE: DNA
<213> ORGANISM: Brassica napus

<400> SEQUENCE: 39
ctatccacgt tccccatgta tacggaaggg ttgggtggct cgtcaatttg cgaaactggt 60
catattcact ggactcatgg gatttataat agagcaggtg cgttttcaac atctttcttt 120
ttattataaa tccttgtgaa agtcaccatt tctgcacatt cgaccgcttg gcttcatctt 180
cttttgttac ttctttggca gtatataaat cctattgtaa ggaactcaaa gcatccgttg 240
aaaggggatc ttctatacgc tattgaaaga gtgttgaagc tttcagttcc aaatctatat 300
gtgtggctct gcatgttcta ctgcttcttc cacctttggt atgtatgccg tgatcccttc 360
tctctcaaca taatttccaa agatgaacaa cagaaaaagg atatatatct catgaagaaa 420
ttaataagtg taggtttttc tgatcacaaa tctctttgca ttgttcttgt ccgcaggtta 480
aacatattgg cagagctgct ctgcttcggg gaccgtgaat tctacaaaga ttggtg 536

<210> SEQ ID NO 40
<211> LENGTH: 526
<212> TYPE: DNA
<213> ORGANISM: Brassica napus

<400> SEQUENCE: 40
ctatccacgt tccccatgta tacggaaggg ttgggtggct cgtcaatttg cgaaactggt 60
catattcact ggactcatgg gatttataat agagcaggtg cgttttcaac atctttcttt 120
ttattataaa tccttgtgaa agtcaccatt tctgcacatt cgaccgcttg gcttcatctt 180
cttttgttac ttctttggca gtatataaat cctattgtaa ggaactcaaa gcatccgttg 240
aaaggggatc ttctatacgc tattgaaaga gtgttgaagc tttcagttcc aaatctatat 300
gtgtggctct gcatttcttc cacctttggt atgtatgccg tgatcccttc tctctcaaca 360
taatttccaa agatgaacaa cagaaaaagg atatatatct catgaagaaa ttaataagtg 420
taggtttttc tgatcacaaa tctctttgca ttgttcttgt ccgcaggtta aacatattgg 480
cagagctgct ctgcttcggg gaccgtgaat tctacaaaga ttggtg 526

```
<210> SEQ ID NO 41
<211> LENGTH: 92
<212> TYPE: DNA
<213> ORGANISM: Brassica napus

<400> SEQUENCE: 41

ccaaatctat atgtgtggct ctgcatgttc tactgcttct tccacctttg gtatgtatgc     60

cgtgatccct tctctctcaa cataatttcc aa                                   92


<210> SEQ ID NO 42
<211> LENGTH: 82
<212> TYPE: DNA
<213> ORGANISM: Brassica napus

<400> SEQUENCE: 42

ccaaatctat atgtgtggct ctgcatttct tccacctttg gtatgtatgc cgtgatccct     60

tctctctcaa cataatttcc aa                                              82


<210> SEQ ID NO 43
<211> LENGTH: 1386
<212> TYPE: DNA
<213> ORGANISM: Brassica napus

<400> SEQUENCE: 43

atggcagcga agatctccca gcttgcgtgt ttctcctcca ccaaccgcca attccacttc     60

cagaaccgat cgtttccaag ccttaggttc cgtcccgagg taaatttctt cgagtatctc    120

atgtaaagga ccgagctttc gtcgttttga tctgattacg ctgatgccca gtatcgtaat    180

ttcctgattg ctgtcgaaaa gttacgagct tgattggttt tagtcctact cagagactta    240

gaaatggctc ttctttggac ttgaattgca tccttctttg atagctctgt tctttgcttg    300

tagctctgtg ccttttgaat gcgttatctg tgctaataag cttggcatgg tggcagtctt    360

ttgtagttag aagcgttgtt gatgggaaca gctcggaaac accagcttct ctgagctatg    420

cagctgaggt ttcgaaacct ttcgttgaga aaacatctac agtggatgaa actactacgg    480

gtaaagaggt tatcacagag tcggtagagg aacatgttgc cacaacacag cctaaaagag    540

cagcgaagat tcatgacttc tgttttggca ttccttatgg tactttttgt gactctctct    600

cagaacttaa tttcaaatct tagcgttact gagctgcttg ttaaagttcc taatgcaact    660

catatcatat tcattgtcag ggtaacttat tggtgttatt ttacttctca ggtggtctgg    720

ttatgagtgg aggattgctt ggatttgcgt tttcacgaaa tcttacaagt ttaagtactg    780

gggttctcta tggtggtggc cttctagctc ttagtacgtt gagcatgaag atttggcgac    840

agggaaagtc tagtttccct tatattctag gtcaagcagg taatcttcat ctactggtat    900

cttacacatg attagtggat atatgaaaga agtgggatac taaaaagtgt tcatctctta    960

accaagatca ctatgtccac attgtgctta ctctcattct ttcgatacaa taaatttgca   1020

gtgctttcag ctgtcgtctt ctggaagaac ttcacatctt actctatggt aattcatcgt   1080

ctttgtgatc atgctgattg tttaaatgtt gcttgcttga cttcaactgc ttaatgttgt   1140

acttttgcag actaagaagc tgtttcctgc cgggctattt gctgtcgtca ggtgagaagt   1200

tcttttgtga tctataagag agtctaatgt atctatcttt attggcttaa tcatgcaacc   1260

ttgtgttcgt gtctttttca ttgcagtgct gccatgttgt gtttctattc gtacgtggtg   1320

ctctctggag gaaacccacc tccaaagaaa cttaaaccat ctgctactac tagtccttca   1380

tactga                                                              1386
```

<210> SEQ ID NO 44
<211> LENGTH: 573
<212> TYPE: DNA
<213> ORGANISM: Brassica napus

<400> SEQUENCE: 44

```
aaagaagtgg gatactaaaa agtgttcatc tcttaaccaa gatcactatg tccacattgt     60

gcttactctc attctttcga tacaataaat ttgcagtgct ttcagctgtc gtcttctgga    120

agaacttcac atcttactct atggtaattc atcgtctttg tgatcatgct gattgtttaa    180

atgttgcttg cttgacttca actgcttaat gttgtacttt tgcagactaa gaagctgttt    240

cctgccgggc tatttgctgt cgtcaggtga gaagttcttt tgtgatctat aagagagtct    300

aatgtatcta tctttattgg cttaatcatg caaccttgtg ttcgtgtctt tttcattgca    360

gtgctgccat gttgtgtttc tattcgtacg tggtgctctc tggaggaaac ccacctccaa    420

agaaacttaa accatctgct actactagtc cttcatactg aagaaacttc acataggtta    480

gattcaaaga tgaagatctt ctcttttggt ggctcttgtg cgttgcattc ctggtgtaat    540

tttatacttt tgacttttga ggcaacaact gtg                                 573
```

<210> SEQ ID NO 45
<211> LENGTH: 565
<212> TYPE: DNA
<213> ORGANISM: Brassica napus

<400> SEQUENCE: 45

```
aaagaagtgg gatactaaaa agtgttcatc tcttaaccaa gatcactatg tccacattgt     60

gcttactctc attctttcga tacaataaat ttgcagtgct ttcagctgtc gtcttctgga    120

agaacttcac atcttactct atggtaattc atcgtctttg tgatcatgct gattgtttaa    180

atgttgcttg cttgacttca actgcttaat gttgtacttt tgcagactaa gaagctgttt    240

cctgccgggc tatttgctgt cgtcaggtga gaagttcttt tgtgatctat aagagagtct    300

aatgtatcta tctttattgg cttaatcatg caaccttgtg ttcgtgtctt tttcattgca    360

gtgctgccat gttgtgtttc tattcgtacc tctggaggaa acccacctcc aaagaaactt    420

aaaccatctg ctactactag tccttcatac tgaagaaact tcacataggt tagattcaaa    480

gatgaagatc ttctcttttg gtggctcttg tgcgttgcat tcctggtgta attttatact    540

tttgactttt gaggcaacaa ctgtg                                          565
```

<210> SEQ ID NO 46
<211> LENGTH: 112
<212> TYPE: DNA
<213> ORGANISM: Brassica napus

<400> SEQUENCE: 46

```
attgcagtgc tgccatgttg tgtttctatt cgtacgtggt gctctctgga ggaaacccac     60

ctccaaagaa acttaaacca tctgctacta ctagtccttc atactgaaga aa            112
```

<210> SEQ ID NO 47
<211> LENGTH: 104
<212> TYPE: DNA
<213> ORGANISM: Brassica napus

<400> SEQUENCE: 47

```
attgcagtgc tgccatgttg tgtttctatt cgtacctctg gaggaaaccc acctccaaag     60

aaacttaaac catctgctac tactagtcct tcatactgaa gaaa                     104
```

<210> SEQ ID NO 48
<211> LENGTH: 694
<212> TYPE: DNA
<213> ORGANISM: Brassica napus

<400> SEQUENCE: 48
ctctatggtg gtggccttct agctcttagt acgttgagca tgaagatttg gcgacaggga 60
aagtctagtt tcccttatat tctaggtcaa gcaggtaatc ttcatctact ggtatcttac 120
acatgattag tggatatatg aaagaagtgg gatactaaaa agtgttcatc tcttaaccaa 180
gatcactatg tccacattgt gcttactctc attctttcga tacaataaat ttgcagtgct 240
ttcagctgtc gtcttctgga agaacttcac atcttactct atggtaattc atcgtctttg 300
tgatcatgct gattgtttaa atgttgcttg cttgacttca actgcttaat gttgtacttt 360
tgcagactaa gaagctgttt cctgccgggc tatttgctgt cgtcaggtga gaagttcttt 420
tgtgatctat aagagagtct aatgtatcta tctttattgg cttaatcatg caaccttgtg 480
ttcgtgtctt tttcattgca gtgctgccat gttgtgttct ctggaggaaa cccacctcca 540
aagaaactta aaccatctgc tactactagt ccttcatact gaagaaactt cacataggtt 600
agattcaaag atgaagatct tctcttttgg tggctcttgt gcgttgcatt cctggtgtaa 660
ttttatactt ttgacttttg aggcaacaac tgtg 694

<210> SEQ ID NO 49
<211> LENGTH: 108
<212> TYPE: DNA
<213> ORGANISM: Brassica napus

<400> SEQUENCE: 49
cagtgctgcc atgttgtgtt tctattcgta cgtggtgctc tctggaggaa acccacctcc 60
aaagaaactt aaaccatctg ctactactag tccttcatac tgaagaaa 108

<210> SEQ ID NO 50
<211> LENGTH: 89
<212> TYPE: DNA
<213> ORGANISM: Brassica napus

<400> SEQUENCE: 50
cagtgctgcc atgttgtgtt ctctggagga aacccacctc caaagaaact taaaccatct 60
gctactacta gtccttcata ctgaagaaa 89

<210> SEQ ID NO 51
<211> LENGTH: 219
<212> TYPE: DNA
<213> ORGANISM: Brassica napus

<400> SEQUENCE: 51
attgcagtgc tgctatgttg tgtttctatt cgtacgtggt gctctctgga ggaaacccac 60
ctccaaagaa acttaaacca tctgctacta ctagcccttc atactgaaga aacttcacat 120
aggttagatt caaagatgga gatcttctct tttggtggct cttgtgcgtt tgattcctgg 180
tgtaatttta tactttagac ttttgaggca acaactgtg 219

<210> SEQ ID NO 52
<211> LENGTH: 132
<212> TYPE: DNA
<213> ORGANISM: Brassica napus

<400> SEQUENCE: 52
attgcagtgc tgctatgttg tgtttctatt cgtaggttag attcaaagat ggagatcttc 60
tcttttggtg gctcttgtgc gtttgattcc tggtgtaatt ttatacttta gacttttgag 120
gcaacaactg tg 132

<210> SEQ ID NO 53
<211> LENGTH: 123
<212> TYPE: DNA
<213> ORGANISM: Brassica napus

<400> SEQUENCE: 53
ctatgttgtg tttctattcg tacgtggtgc tctctggagg aaacccacct ccaaagaaac 60
ttaaaccatc tgctactact agcccttcat actgaagaaa cttcacatag gttagattca 120
aag 123

<210> SEQ ID NO 54
<211> LENGTH: 36
<212> TYPE: DNA
<213> ORGANISM: Brassica napus

<400> SEQUENCE: 54
ctatgttgtg tttctattcg taggttagat tcaaag 36

<210> SEQ ID NO 55
<211> LENGTH: 374
<212> TYPE: DNA
<213> ORGANISM: Brassica napus

<400> SEQUENCE: 55
ctctctctcg aaacttagtt tcaataggat attgctgagc ttcctgttga agttattaga 60
ggacactttg tcaggtgggc tcgttatgag tggagggttg cttggatttg cgttttcacg 120
gaacctaaca agtttaagta ctggggtcct ctatggtggt ggccttcttg ctcttagtac 180
attgagcttg aagatttggc gacagggaaa atctagtttc ccttatattc ttggtcaagc 240
aggtaatctt tcatttactg tctacatgaa caattaatca gtgctttcag ctgtcgtctt 300
cagcaggtat actttgtgat actaagagat gcttactaat tctttcgaaa tcctaaattt 360
gcagtgcttt cagc 374

<210> SEQ ID NO 56
<211> LENGTH: 371
<212> TYPE: DNA
<213> ORGANISM: Brassica napus

<400> SEQUENCE: 56
ctctctctcg aaacttagtt tcaataggat attgctgagc ttcctgttga agttattaga 60
ggacactttg tcaggtgggc tcgttatgag tggagggctt ggatttgcgt tttcacggaa 120
cctaacaagt ttaagtactg gggtcctcta tggtggtggc cttcttgctc ttagtacatt 180
gagcttgaag atttggcgac agggaaaatc tagtttccct tatattcttg gtcaagcagg 240
taatctttca tttactgtct acatgaacaa ttaatcagtg ctttcagctg tcgtcttcag 300
caggtatact ttgtgatact aagagatgct tactaattct ttcgaaatcc taaatttgca 360
gtgctttcag c 371

<210> SEQ ID NO 57
<211> LENGTH: 81

<212> TYPE: DNA
<213> ORGANISM: Brassica napus

<400> SEQUENCE: 57
ttgtcaggtg ggctcgttat gagtggaggg ttgcttggat ttgcgttttc acggaaccta 60
acaagtttaa gtactggggt c 81

<210> SEQ ID NO 58
<211> LENGTH: 78
<212> TYPE: DNA
<213> ORGANISM: Brassica napus

<400> SEQUENCE: 58
ttgtcaggtg ggctcgttat gagtggaggg cttggatttg cgttttcacg gaacctaaca 60
agtttaagta ctggggtc 78

<210> SEQ ID NO 59
<211> LENGTH: 190
<212> TYPE: DNA
<213> ORGANISM: Brassica napus

<400> SEQUENCE: 59
gtttcggcat tccttatggt atacttgctc actctctctc tcgaaactta gtttcaatag 60
gatattgctg agcttcctgt tgaagttatt agaggacact ttgtcaggtg ggctcgttat 120
gagtggaggg tttgcttgga tttgcgtttt cacggaacct aacaagttta agtactgggg 180
tcctctatgg 190

<210> SEQ ID NO 60
<211> LENGTH: 87
<212> TYPE: DNA
<213> ORGANISM: Brassica napus

<400> SEQUENCE: 60
ttgtcaggtg ggctcgttat gagtggaggg ttgcttggat ttgcgttttc acggaaccta 60
acaagtttaa gtactggggt cctctat 87

<210> SEQ ID NO 61
<211> LENGTH: 88
<212> TYPE: DNA
<213> ORGANISM: Brassica napus

<400> SEQUENCE: 61
ttgtcaggtg ggctcgttat gagtggaggg tttgcttgga tttgcgtttt cacggaacct 60
aacaagttta agtactgggg tcctctat 88

<210> SEQ ID NO 62
<211> LENGTH: 3441
<212> TYPE: DNA
<213> ORGANISM: Brassica napus

<400> SEQUENCE: 62
atgccccttt tccagcggaa aaagccgccg ccgtctgagg acctcccgga cgacgacgac 60
acccagaaca aatcgaaaaa ccgtaagaaa ccgagcggga aggcgaagtg gtcgtgcgtg 120
gattcgtgct gctggttcat agggtgcgtg tgcctcacgt ggtggttcct cctcttcctc 180
tacaacgcca tgcccgcgag ctttcctcag tacgttaccg aggcgatcac gggccctttg 240
cccgacccgc ccggcgtgaa gctgaagaaa gaaggtctca gggcgaagca tcccgttgtg 300

-continued

```
ttcatccctg ggattgttac gggtggactt gagctttggg aagggaaaca gtgtgctgat    360
ggtttgttta ggaagcgctt gtggggtgga actttcggtg aagtctacaa aaggtcagct    420
tccttacctt tttgggtttt tatattagtt gcaaaaagct atcttcttta gattcctaat    480
gtgtgtttgt gtaagggaag caatagcatt tcaattaaac acgttttgat ctcaaaatgt    540
cagcttcctt ggagttttga agtcaatgct gtaaccaaat atgttactgc acatgccttt    600
agattacgtt cttaacaagt tgcttccttt attgtcattg gatttagctt acttgtacgg    660
agtgtatact aaagtagtga cttttcttgt tgtgttacga gtagatgtta aagatgtgat    720
ataggatggt tgctttattc ttcaactatg tccatgtgca actaaaagtt agtttctttt    780
gtcttttgga tcaaagtgct tttctcaaat tctttccgag aactgaaaaa ttgagatttt    840
caaaagtttg gtctagttat tgtcttgagt ttcatccatc ttcattctgt tagctagcta    900
tgaactcctc tttttgtgtg ttatgatctg catctttcct ttttcggccc acggatcctc    960
ttgttgcttg gagatggggc agtgttaccg ttgagactaa cagtgttctt gttcatagta   1020
tctttacata attggttatc tctttgattc aggcctctat gctgggtgga acacatgtca   1080
cttgacaacg aaactggttt agatcctgct ggtattagaa tcagagctgt atcaggactc   1140
gtggctgctg actacttcgc tcctggctac ttcgtctggg cggtgctgat tgctaacctt   1200
gcacatattg gatacgagga gaagaacatg tacatggctg catatgactg gaggctttcg   1260
tttcagaaca cagaggttct tctctcatta aacaaactct cttattctct ctttatctct   1320
taggttccaa ctgtctttca tttgttgaat cattaggtgc gtgaccagac gcttagccgt   1380
atgaaaagca atatagagct gatggtttcc accaacggtg ggaaaaaagc agttatagtt   1440
cctcattcca tgggggtatt gtatttctta cattttatga aatgggttga ggcaccagct   1500
cctatgggcg gcggtggtgg gcctgattgg tgtgcaaagc atatcaaagc ggtgatgaac   1560
attggtggac cgtttcttgg tgttccaaaa gctgtcgcag ggcttttctc cgctgaggca   1620
aaggatgttg cagttgccag gtattgaatt agctgactgt ggttttagcc aataaaatct   1680
cttattctgc ttttgaaact atgcagagcg attgcgccag ggttcttaga cactgatata   1740
ttcagactcc agacgctgca acacgtgatg agaatgacac gcacatggga ctcaacgatg   1800
tctatgatac ctaagggagg tgacacaata tggggcggtc ttgattggtc gccggagaaa   1860
ggccacatat gttccggtaa aaagaaaagt agcaacaaga ctcgcggaga agctggtgaa   1920
aactcagttt ccaagacaaa gcctgttaac tacggaagaa tcatatcgtt cgggaaagat   1980
gtggctgagg ctgcgccgtc tgagattgaa aacattgatt ttcgagtaag gacatatgaa   2040
ctgttaatac ttttttgtg attagatgac taataggtac gtttttactt ggtgaagggt   2100
gcggtgaaag gtcagagtat cccaaacaac acatgccgtg acgtgtggac ggagtatcat   2160
gatatgggaa tcggagggat caaagctatt gctgagtata aggtctacac tgctgacgcg   2220
gttatagatt tgctacatta tgttgctcct aagatgatgg cgcgtggtgc tgctcatttc   2280
tcctatggga ttgctgatga tttagatgac cctaagtatg aacatcacag acactggtcc   2340
aatccattgg aaacaaagta agtggttttg tttttgtacc aactctatgc tttgtcctga   2400
tgcattatta gtcttttagt tttttcccct tgttgaatat gcttatcaac tcaaagctaa   2460
gagcatctcc aatggtattc aatttttcat tttaaaatag agtttagagt aaaaatgctc   2520
aaatagtact ctatttttca ttctatagta gagtaaaaaa tggatttagt ctataaatag   2580
agtagtttat ttttttttcca ccactctatt cttcactata aaatagaata ccataggagt   2640
ataactcaat tccattatag acttattcta ttttgagaaa aaaaaagagt gaacgattag   2700
```

```
agatagtcta gtttgagtct ttccgaaaag gctttactta gttatattta ggttttaaag   2760

ttgatacatg tgatgcttgc ttataaaacc agctctagga tggctttgac atgacaaata   2820

aaccaactaa ttcgaaatct atttgactga aaacccttag taccaccttc tagttttaga   2880

gtttatctat ccctttgagg atcatttccc tctgtcttat ccttagaaac cacatttggt   2940

ttgttctgcc gtttcaggtt acccaatgcc cctgaaatgg agatctactc actgtatgga   3000

gttgggatac caacagaacg atcatacatc tacaagctca atcagtctcc agacagctgc   3060

atccccttc atatcttcac ttctgctcac gaggaggaca aagaaagctg tctgaaagca   3120

ggagtttaca acgtggatgg agatgaaaca gtaccggtcc taagcgcagg gttcatgtgt   3180

gctaaagcgt ggcgcggcaa gacgagattc aacccttctg gaatcaagac ttacattaga   3240

gaatacaacc actctccacc agctaacctg ctagaagggc gagggacgca gagtggggct   3300

catgttgata tcatgggaaa ctttgcgttg atcgaggata tcatgagggt tgccacggga   3360

ggtaacgggt ccgacctagg acatgaccag gtccactctg gtatatttga atggtctgag   3420

cgtattgact tgaagctgtg a                                             3441
```

```
<210> SEQ ID NO 63
<211> LENGTH: 235
<212> TYPE: DNA
<213> ORGANISM: Brassica napus

<400> SEQUENCE: 63

tgcggtgaaa ggtcagagta tcccaaacaa cacatgccgt gacgtgtgga cggagtacca     60

tgatatggga attggaggga tcaaagctat tgctgagtat aaggtctaca ctgctgacgc    120

ggttatagat ttattacatt atgttgctcc taagatgatg gcgcgtggcg ccgctcattt    180

ctcctatggg attgctgatg atttggatga ccccaagtac gaacatcaca ggcac         235
```

```
<210> SEQ ID NO 64
<211> LENGTH: 230
<212> TYPE: DNA
<213> ORGANISM: Brassica napus

<400> SEQUENCE: 64

tgcggtgaaa ggtcagagta tcccaaacaa cacatgccgt gacgtgtgga cggagtacca     60

tgatatggga attggaggga tcaaagctat tgctgagtat ctacactgct gacgcggtta    120

tagatttatt acattatgtt gctcctaaga tgatggcgcg tggcgccgct catttctcct    180

atgggattgc tgatgatttg gatgacccca agtacgaaca tcacaggcac               230
```

```
<210> SEQ ID NO 65
<211> LENGTH: 96
<212> TYPE: DNA
<213> ORGANISM: Brassica napus

<400> SEQUENCE: 65

aacacatgcc gtgacgtgtg gacggagtac catgatatgg gaattggagg gatcaaagct     60

attgctgagt ataaggtcta cactgctgac gcggtt                               96
```

```
<210> SEQ ID NO 66
<211> LENGTH: 91
<212> TYPE: DNA
<213> ORGANISM: Brassica napus

<400> SEQUENCE: 66
```

aacacatgcc gtgacgtgtg gacggagtac catgatatgg gaattggagg gatcaaagct 60
attgctgagt atctacactg ctgacgcggt t 91

<210> SEQ ID NO 67
<211> LENGTH: 383
<212> TYPE: DNA
<213> ORGANISM: Brassica napus

<400> SEQUENCE: 67
gagaagctgg tgaaaactca gtttccaaga caaagcctgt taactacgga agaatcatat 60
cgttcgggaa agatgtggct gaggctgcgc cgtctgagat tgaaaacatt gattttcgag 120
taaggacata tgaactgtta atactttttt tgtgattaga tgactaatag gtacgttttt 180
acttggtgaa gggtgcggtg aaaggtcaga gtatcccaaa caacacatgc cgtgacgtgt 240
ggacggagta tcatgatatg ggaatcggag ggatcaaagc tattgctgag tataaggtct 300
acactgctga cgcggttata gatttgctac attatgttgc tcctaagatg atggcgcgtg 360
gtgctgctca tttctcctat ggg 383

<210> SEQ ID NO 68
<211> LENGTH: 304
<212> TYPE: DNA
<213> ORGANISM: Brassica napus

<400> SEQUENCE: 68
gagaagctgg tgaaaactca gtttccaaga caaagcctgt taactacgga agaatcatat 60
cgttcgggaa agatgtggct gaggctgcgc cgtctgagat tgaaaacatt gattttcgag 120
taaggacata tgaactgtta atactttttt tgtgattaga tgactaatag gtacgttttt 180
acttggtgaa gggtgcggtg aaaggtcaga gtataaggtc tacactgctg acgcggttat 240
agatttgcta cattatgttg ctcctaagat gatggcgcgt ggtgctgctc atttctccta 300
tggg 304

<210> SEQ ID NO 69
<211> LENGTH: 111
<212> TYPE: DNA
<213> ORGANISM: Brassica napus

<400> SEQUENCE: 69
aaaggtcaga gtatcccaaa caacacatgc cgtgacgtgt ggacggagta tcatgatatg 60
ggaatcggag ggatcaaagc tattgctgag tataaggtct acactgctga c 111

<210> SEQ ID NO 70
<211> LENGTH: 32
<212> TYPE: DNA
<213> ORGANISM: Brassica napus

<400> SEQUENCE: 70
aaaggtcaga gtataaggtc tacactgctg ac 32

<210> SEQ ID NO 71
<211> LENGTH: 614
<212> TYPE: DNA
<213> ORGANISM: Brassica napus

<400> SEQUENCE: 71
ctccagacgt tgcagcatgt aatgagaatg acacgaacat gggactcaac gatgtctatg 60
atacctaaag gaggtgacac gatatggggt ggtcttgact ggtctccgga gcaaggctac 120
acttgctctg gtaaaaaaca aaagagcaac gagactcgcg gtgaagaagg tgagagttta 180
gttaccaaga cgaagcctgt caactacgga agaatcatat cgtttgggaa agacgtggca 240
gaggctcatc catctgagat taaaaacatt gattttcgag taaggagcac taatcatatt 300
aaacaaacct cttgtagctt ttgtgattta gatgattagt aatctgtata tgtgttactt 360
ggtgaagggt gctgtgaaag gtcagagtat cccaaacaac acgtgccgtg acgtgtggac 420
ggagtaccat gatatgggaa ttggagggat caaagctatt gctgagtata aggtctacac 480
tgctgataca gtcattgatt tgctacatta tgttgctcct aagatgatgg cgcgtggttc 540
tgctcatttc tcttatggga ttgcggatga tttagatgat cctaagtatg atcatcccag 600
acactggtct aatc 614

<210> SEQ ID NO 72
<211> LENGTH: 599
<212> TYPE: DNA
<213> ORGANISM: Brassica napus

<400> SEQUENCE: 72
ctccagacgt tgcagcatgt aatgagaatg acacgaacat gggactcaac gatgtctatg 60
atacctaaag gaggtgacac gatatggggt ggtcttgact ggtctccgga gcaaggctac 120
acttgctctg gtaaaaaaca aaagagcaac gagactcgcg gtgaagaagg tgagagttta 180
gttaccaaga cgaagcctgt caactacgga agaatcatat cgtttgggaa agacgtggca 240
gaggctcatc catctgagat taaaaacatt gattttcgag taaggagcac taatcatatt 300
aaacaaacct cttgtagctt ttgtgattta gatgattagt aatctgtata tgtgttactt 360
ggtgaagggt gctgtgaaag gtcagagtat cccaaacaac acgtgccgtg acgtgtggac 420
ggagtaccat gatatgggaa ttggagggat caaagctatt gctgagtatg atacagtcat 480
tgatttgcta cattatgttg ctcctaagat gatggcgcgt ggttctgctc atttctctta 540
tgggattgcg gatgatttag atgatcctaa gtatgatcat cccagacact ggtctaatc 599

<210> SEQ ID NO 73
<211> LENGTH: 95
<212> TYPE: DNA
<213> ORGANISM: Brassica napus

<400> SEQUENCE: 73
gtaccatgat atgggaattg gagggatcaa agctattgct gagtataagg tctacactgc 60
tgatacagtc attgatttgc tacattatgt tgctc 95

<210> SEQ ID NO 74
<211> LENGTH: 80
<212> TYPE: DNA
<213> ORGANISM: Brassica napus

<400> SEQUENCE: 74
gtaccatgat atgggaattg gagggatcaa agctattgct gagtatgata cagtcattga 60
tttgctacat tatgttgctc 80

<210> SEQ ID NO 75
<211> LENGTH: 546
<212> TYPE: DNA
<213> ORGANISM: Brassica napus

<400> SEQUENCE: 75

```
tcaacgatgt ctatgatacc taaaggaggt gacacgatat ggggtggtct tgactggtct      60

ccggagcaag gctacacttg ctctggtaaa aaacaaaaga gcaacgagac tcgcggtgaa     120

gaaggtgaga gtttagttac caagacgaag cctgtcaact acggaagaat catatcgttt     180

gggaaagacg tggcagaggc tcatccatct gagattaaaa acattgattt tcgagtaagg     240

agcactaatc atattaaaca aacctcttgt agcttttgtg atttagatga ttagtaatct     300

gtatatgtgt tacttggtga agggtgctgt gaaaggtcag agtatcccaa acaacacgtg     360

ccgtgacgtg tggacggagt accatgatat gggaattgga gggatcaaag ctattgctga     420

tacagtcatt gatttgctac attatgttgc tcctaagatg atggcgcgtg gttctgctca     480

tttctcttat gggattgcgg atgatttaga tgatcctaag tatgatcatc ccagacactg     540

gtctaa                                                                546


<210> SEQ ID NO 76
<211> LENGTH: 102
<212> TYPE: DNA
<213> ORGANISM: Brassica napus

<400> SEQUENCE: 76

gtaccatgat atgggaattg gagggatcaa agctattgct gagtataagg tctacactgc      60

tgatacagtc attgatttgc tacattatgt tgctcctaag at                        102


<210> SEQ ID NO 77
<211> LENGTH: 81
<212> TYPE: DNA
<213> ORGANISM: Brassica napus

<400> SEQUENCE: 77

gtaccatgat atgggaattg gagggatcaa agctattgct gatacagtca ttgatttgct      60

acattatgtt gctcctaaga t                                                81


<210> SEQ ID NO 78
<211> LENGTH: 550
<212> TYPE: DNA
<213> ORGANISM: Brassica napus

<400> SEQUENCE: 78

ctccagacgt tgcagcatgt aatgagaatg acacgcacat gggactcaac aatgtctatg      60

atacctaaag gaggtgacac gatatggggt ggtcttgatt ggtctccgga gcaagggtac     120

acttgctctg gtaaaaagca aaagaacaac gagactcgcg gtgaagaaag tgagagttta     180

gttaccaaga cgaagcctgt caactacgga agaatcatat cgtttgggaa agacgtggca     240

gaggctcatc tatctgagat taaaaacatt gattttcgag taaggacata taaacctcta     300

gtagctttgg tggttagacg attaataatc tttgtatatg ttactttgtt gaagggtgct     360

gtgaaaggtc agagtatccc aaacaacacg tgccgtgacg tgtggacaga gtaccatgat     420

atgggaactg gagggatcaa agctattgct gagtataagg tctacactgc tgatgcagtc     480

attgatttgc tacattatgt tgctcctaag atgatggcgc gtggttcctc tcatttctct     540

tacgggattg                                                            550


<210> SEQ ID NO 79
<211> LENGTH: 542
<212> TYPE: DNA
<213> ORGANISM: Brassica napus

<400> SEQUENCE: 79
```

ctccagacgt tgcagcatgt aatgagaatg acacgcacat gggactcaac aatgtctatg 60
atacctaaag gaggtgacac gatatggggt ggtcttgatt ggtctccgga gcaagggtac 120
acttgctctg gtaaaaagca aaagaacaac gagactcgcg gtgaagaaag tgagagttta 180
gttaccaaga cgaagcctgt caactacgga agaatcatat cgtttgggaa agacgtggca 240
gaggctcatc tatctgagat taaaaacatt gattttcgag taaggacata taaacctcta 300
gtagctttgg tggttagacg attaataatc tttgtatatg ttactttgtt gaagggtgct 360
gtgaaaggtc agagtatccc aaacaacacg tgccgtgacg tgtggacaga gtaccatgat 420
atgggaactg gagggatcaa agctattgct ggtctacact gctgatgcag tcattgattt 480
gctacattat gttgctccta agatgatggc gcgtggttcc tctcatttct cttacgggat 540
tg 542

<210> SEQ ID NO 80
<211> LENGTH: 104
<212> TYPE: DNA
<213> ORGANISM: Brassica napus

<400> SEQUENCE: 80
gacgtgtgga cagagtacca tgatatggga actggaggga tcaaagctat tgctgagtat 60
aaggtctaca ctgctgatgc agtcattgat ttgctacatt atgt 104

<210> SEQ ID NO 81
<211> LENGTH: 96
<212> TYPE: DNA
<213> ORGANISM: Brassica napus

<400> SEQUENCE: 81
gacgtgtgga cagagtacca tgatatggga actggaggga tcaaagctat tgctggtcta 60
cactgctgat gcagtcattg atttgctaca ttatgt 96

<210> SEQ ID NO 82
<211> LENGTH: 337
<212> TYPE: DNA
<213> ORGANISM: Brassica napus

<400> SEQUENCE: 82
ctccagacgt tgcagcatgt aatgagaatg acacgcacat gggactcaac aatgtctatg 60
atacctaaag gaggtgacac gatatggggt ggtcttgatt ggtctccgga gcaagggtac 120
acttgctctg gtaaaaagca aaagaacaac gagactcgcg gtgaagaaag tgagagttta 180
gttaccaaga cgaagcctgt caactacgga agaatcatat cgtttgggaa agacgtggca 240
gaggctcatc tatctgagat taaaaacatt gattttcgac attatgttgc tcctaagatg 300
atggcgcgtg gttcctctca tttctcttac gggattg 337

<210> SEQ ID NO 83
<211> LENGTH: 117
<212> TYPE: DNA
<213> ORGANISM: Brassica napus

<400> SEQUENCE: 83
gacgtgtgga cagagtacca tgatatggga actggaggga tcaaagctat tgctgagtat 60
aaggtctaca ctgctgatgc agtcaatttg atttgctaca ttatgttgct cctaagt 117

<210> SEQ ID NO 84

<211> LENGTH: 19
<212> TYPE: DNA
<213> ORGANISM: Brassica napus

<400> SEQUENCE: 84
cattatgttg ctcctaagt 19

<210> SEQ ID NO 85
<211> LENGTH: 1859
<212> TYPE: DNA
<213> ORGANISM: Brassica napus

<400> SEQUENCE: 85
atggcggcaa cagcagcagc ttcgagcttg caaatggcta caacaaggcc aagcatttct 60
gcagcctcta ccaaaacaag gacctacgtt gtcggtgcca atcccaggaa cgcatcgtgg 120
gacaaaattg cttgcactcc ccatctatcg aacctcgggt gtttgagaaa cgacagtgct 180
cttccagctt ctaaaaagag tttttccttt tcgacaaagg ccatgtctga atccagcgaa 240
agcaaggctt cttctggact tcccattgat ttgagaggtt cctttctagt catatcttaa 300
tcatcattac taagattgat tgctattaga agacaatgag ctgtttgaat taaatcaact 360
gtgttaaatg gtttctaggg aaaagagcct ttattgctgg tatagctgat gataatggat 420
atggttgggc catagccaaa tctcttgctg ctgctggtgc tgaaattttg gttgggactt 480
gggttcctgt aagtttcctt tttttttttt ttttaattaa ctctattgag cagtttaagt 540
ttcctcatgt actgacgacc tttgaatggt gctctactag gcacttaaca tttttgagac 600
gagcttgagg cgtggaaaat tcgaccagtc gcgcgtgtaa ggacttacaa caaaactgat 660
caactctttg tttcttttat tttccacatc atctaatatc taaaattcag gttgccagac 720
ggatcattga tggagattaa aaaggtttat cctttggatg ctgtctttga caatcctgaa 780
gatgtccctg aagatgtacg tgagagaata catctttcac atcatactaa aacccttaat 840
atccatatta gttatgatac attctttttt cttacaggtg aaagcgaata agcgatatgc 900
tggatcgtca aactggactg tacaggaagc tgcagaatgt gtgagacaag attttggaag 960
cattgacatt cttgtccact cacttgcaaa tggaccagag gcaagaactc tatctgaaac 1020
tgttttacaa gaactgtatt ctgttttgcc taatgggaaa tcttctgata tttttaggtt 1080
agcaaacctc ttcttgagac atcgaggaaa ggctatcttg ctgctatctc tgcttccagc 1140
tactcctttg tttccctcct cagccatttt ctcccaatta tgaacccagg catgtcacaa 1200
aactttgtat tattcctctt cttctttata attatttgtt tttttttttt ttttaaattt 1260
tatttgtttc tctatgatat gatataggag gtgcttctat ctctcttact tacattgcct 1320
ctgaaaggat cattcccggg taagggtcat actatagctt cacaacattg ttttgtttct 1380
caatagatga ttacaagtgt atcttttaat ttctgttgtt aggtatggtg gaggtatgag 1440
ttctgccaag gccgcactag agagtgatac acgtgtgctt gcatttgaag ctgggaggaa 1500
acaaaacatt agggtcaaca ctatctctgc aggccctttg ggaagccgag cagctaaagc 1560
aattgggttc atagacacaa tgatcgagta ttcatacaat aacgcgccta ttcagaaaac 1620
actgactgca ggttcattca tacatacaag catttctttt tgttggcttt cagttttctt 1680
tggaaatttt attaaaaaat gaggaatatg atgatgcaga tgaagttggg aatgcggcag 1740
ccttcttggt atctccattg gcatctgcca taactggtgc aaccatctat gtggacaatg 1800
gcttgaattc aatgggtgtt gctcttgaca gccccgtttt caaagacctc aacaaataa 1859

<210> SEQ ID NO 86
<211> LENGTH: 406
<212> TYPE: DNA
<213> ORGANISM: Brassica napus

<400> SEQUENCE: 86
ggtttatcct ttggatgctg tctttgacac tcctgatgat gtccctgaag atgtaaggga 60
gatttacatc tttcacatca tattaaaacc cttaatatcc aaattagtta tgataacatt 120
ttatttttcc aggtgaaagc gaataagcga tatgctggat catcaaactg gactgtacag 180
gaagctgcag aatgtgtgag acaagatttt ggaagcattg acattcttgt ccactcactt 240
gcaaatggac cagaggcaag aactctatct gaaactgttt tacaagaact ttattctgtt 300
ttgcctgatg ggagatcttc tgaatatttt taggttagca aacctcttct ggagacaacg 360
aggaaaggct atcttgctgc tatttctgct tccagctact cctttg 406

<210> SEQ ID NO 87
<211> LENGTH: 400
<212> TYPE: DNA
<213> ORGANISM: Brassica napus

<400> SEQUENCE: 87
ggtttatcct ttggatgctg tctttgacac tcctgatgat gtccctgaag atgtaaggga 60
gatttacatc tttcacatca tattaaaacc cttaatatcc aaattagtta tgataacatt 120
ttatttttcc aggtgaaagc gaataagcga tatgctggat catcaaactg gactgtacag 180
gaagctgcag aatgtgtgag acaagatttt ggaagcattg acattcttgt ccactcactt 240
gcaccagagg caagaactct atctgaaact gttttacaag aactttattc tgttttgcct 300
gatgggagat cttctgaata tttttaggtt agcaaacctc ttctggagac aacgaggaaa 360
ggctatcttg ctgctatttc tgcttccagc tactcctttg 400

<210> SEQ ID NO 88
<211> LENGTH: 108
<212> TYPE: DNA
<213> ORGANISM: Brassica napus

<400> SEQUENCE: 88
tgagacaaga ttttggaagc attgacattc ttgtccactc acttgcaaat ggaccagagg 60
caagaactct atctgaaact gttttacaag aactttattc tgtttgcc 108

<210> SEQ ID NO 89
<211> LENGTH: 102
<212> TYPE: DNA
<213> ORGANISM: Brassica napus

<400> SEQUENCE: 89
tgagacaaga ttttggaagc attgacattc ttgtccactc acttgcacca gaggcaagaa 60
ctctatctga aactgtttta caagaacttt attctgtttg cc 102

<210> SEQ ID NO 90
<211> LENGTH: 328
<212> TYPE: DNA
<213> ORGANISM: Brassica napus

<400> SEQUENCE: 90
tctcaactgt atgatacatt tttcaggtga aagcgaataa gcgatatgct ggatcatcaa 60
actggacagt acaggtatag tcttatagat gaaagagatg ttttatattt tgaaatgtgt 120
ggtaacatct aaagctagag aaatgtgtgt gtttttgctt gatgcttgcg actttcttaa 180
ctcatctttt tttttctctt tggtattgat taaatcagga agctgctgaa tgtgttaaaa 240
aagattttgg aaccattgac attcttgtcc actcacttgc aaatgggccc gaggtagaga 300
actcatagtg ttcttatctt aatactgt 328

<210> SEQ ID NO 91
<211> LENGTH: 329
<212> TYPE: DNA
<213> ORGANISM: Brassica napus

<400> SEQUENCE: 91
tctcaactgt atgatacatt tttcaggtga aagcgaataa gcgatatgct ggatcatcaa 60
actggacagt acaggtatag tcttatagat gaaagagatg ttttatattt tgaaatgtgt 120
ggtaacatct aaagctagag aaatgtgtgt gtttttgctt gatgcttgcg actttcttaa 180
ctcatctttt tttttctctt tggtattgat taaatcagga agctgctgaa tgtgttaaaa 240
aagattttgg aaccattgac attcttgtcc actcacttgc aaaatgggcc cgaggtagag 300
aactcatagt gttcttatct taatactgt 329

<210> SEQ ID NO 92
<211> LENGTH: 107
<212> TYPE: DNA
<213> ORGANISM: Brassica napus

<400> SEQUENCE: 92
gctgctgaat gtgttaaaaa agattttgga accattgaca ttcttgtcca ctcacttgca 60
aatgggcccg aggtagagaa ctcatagtgt tcttatctta atactgt 107

<210> SEQ ID NO 93
<211> LENGTH: 108
<212> TYPE: DNA
<213> ORGANISM: Brassica napus

<400> SEQUENCE: 93
gctgctgaat gtgttaaaaa agattttgga accattgaca ttcttgtcca ctcacttgca 60
aaatgggccc gaggtagaga actcatagtg ttcttatctt aatactgt 108

<210> SEQ ID NO 94
<211> LENGTH: 650
<212> TYPE: DNA
<213> ORGANISM: Brassica napus

<400> SEQUENCE: 94
catttttgag acgagcttga ggcgtggaaa attcgaccag tcgcgcgtgt aaggacttac 60
aacaaaactg atcaactctt tgtttctttt attttccaca tcatctaata tctaaaattc 120
aggttgccag acggatcatt gatggagatt aaaaaggttt atcctttgga tgctgtcttt 180
gacaatcctg aagatgtccc tgaagatgta cgtgagagaa tacatctttc acatcatact 240
aaaaccctta atatccatat tagttatgat acattctttt ttcttacagg tgaaagcgaa 300
taagcgatat gctggatcgt caaactggac tgtacaggaa gctgcagaat gtgtgagaca 360
agattttgga agcattgaca ttcttgtcca ctcacttgca aatggaccag aggcaagaac 420
tctatctgaa actgttttac aagaactgta ttctgttttg cctaatggga aatcttctga 480
tatttttagg ttagcaaacc tcttcttgag acatcgagga aaggctatct tgctgctatc 540
tctgcttcca gctactcctt tgtttccctc ctcagccatt ttctcccaat tatgaaccca 600
ggcatgtcac aaaactttgt attattcctc ttcttcttta taattatttg 650

<210> SEQ ID NO 95
<211> LENGTH: 273
<212> TYPE: DNA
<213> ORGANISM: Brassica napus

<400> SEQUENCE: 95
catttttgag acgagcttga ggcgtggaaa attcgaccag tcgcgcgtgt aaggacttac 60
aacaagaact gtattctgtt ttgcctaatg ggaaatcttc tgatattttt aggttagcaa 120
acctcttctt gagacatcga ggaaaggcta tcttgctgct atctctgctt ccagctactc 180
ctttgtttcc ctcctcagcc attttctccc aattatgaac ccaggcatgt cacaaaactt 240
tgtattattc ctcttcttct ttataattat ttg 273

<210> SEQ ID NO 96
<211> LENGTH: 108
<212> TYPE: DNA
<213> ORGANISM: Brassica napus

<400> SEQUENCE: 96
gtgtgagaca agattttgga agcattgaca ttcttgtcca ctcacttgca aatggaccag 60
aggcaagaac tctatctgaa actgttttac aagaactgta ttctgttt 108

<210> SEQ ID NO 97
<211> LENGTH: 20
<212> TYPE: DNA
<213> ORGANISM: Brassica napus

<400> SEQUENCE: 97
acaagaactg tattctgttt 20

<210> SEQ ID NO 98
<211> LENGTH: 529
<212> TYPE: DNA
<213> ORGANISM: Brassica napus

<400> SEQUENCE: 98
cattaagaga aacccgtctg cctcttttca taacctcata aatattccaa ccattccatg 60
tctcgcttct ctcatctgtt gttctctgta ggttttaagt tctttttgtc ctcttctata 120
atatgaacac ccttcttaat tgttccttat tgtctacctc tctttattac attcgacaga 180
aaggaacgag tgaaaagagt ttggatcttt aagctttttg atcatgtggg tttgacaaaa 240
gagtttctta cagagatctt tggcattctg tccacctccc ctacctatgt atatgtgtat 300
tatctacgtt gtgttttgtg agggggaggt gggcatactg ccaacagaga tctgttaggg 360
tttctttgta aaacccctca tgatttgttg tattcaagat aaggcattgg ctcgtgttga 420
tcaagatgac ttgatgaaca ctaagatcta ggtttgagga aaaatggtat tatctcggat 480
atactcaacc ttaattatta tgtatgatca ctacatctta gtattttat 529

<210> SEQ ID NO 99
<211> LENGTH: 381
<212> TYPE: DNA
<213> ORGANISM: Brassica napus

<400> SEQUENCE: 99
gtgtaaaaat gacttcatcg aacaaaagaa gtgacgatca catataataa ggttaagtga 60

```
attagagata ataccatttt tcttcaaact ctggtcttag tgatcttgat taccatgatg    120

agccaatgta ctatcttgaa tacatcaaat catgaggggt tttacaaaga aaccctaaca    180

gatctctatt ggcagtatgc ccacctcctc tcacaaaaca caacgtggtt acgaacactt    240

atacacaaat atattcagaa aggaggtgga cagaatgcca aagaactctg taagaaattc    300

ttttgtcaaa cccacatgat caaaaaggtt accgatccaa actttacctt ttatatacgg    360

caaggagcaa aaagtgtttc a                                              381


<210> SEQ ID NO 100
<211> LENGTH: 346
<212> TYPE: DNA
<213> ORGANISM: Brassica napus

<400> SEQUENCE: 100

gtgtaaaaat gacttcatcg aacaaaagaa gtgacgatca catataataa ggttaagtga     60

attagagata ataccatttt tcttcaaact ctggtcttag tgatcttgat taccatgatg    120

agccaatgta ctatcttgaa tacatcaaat catgaggggt tttacaaaga aaccctaaca    180

gatctctatt ggcagtatgc ccacctcctc tcacaaaaca caacgtggtt acgaacactt    240

atacacaaat atattcagaa aggaggtgga cagaatgcca aagagcaaaa aagttaccga    300

tccaaacttt accttttata tacggcaagg agcaaaaagt gtttca                   346


<210> SEQ ID NO 101
<211> LENGTH: 100
<212> TYPE: DNA
<213> ORGANISM: Brassica napus

<400> SEQUENCE: 101

attcagaaag gaggtggaca gaatgccaaa gaactctgta agaaattctt ttgtcaaacc     60

cacatgatca aaaaggttac catccaaact ttacctttta                          100


<210> SEQ ID NO 102
<211> LENGTH: 65
<212> TYPE: DNA
<213> ORGANISM: Brassica napus

<400> SEQUENCE: 102

attcagaaag gaggtggaca gaatgccaaa gagcaaaaag gttaccatcc aaactttacc     60

tttta                                                                 65


<210> SEQ ID NO 103
<211> LENGTH: 267
<212> TYPE: DNA
<213> ORGANISM: Brassica napus

<400> SEQUENCE: 103

cattcgacag aaaggaacga gtgaaaagag tttggatctt taagcttttt gatcatgtgg     60

gtttgacaaa agagtttctt acagagatct ttggcattct gtccacctcc cctacctatg    120

tatatgtgta ttatctacgt tgtgttttgt gagggggagg tgggcatact gccaacagag    180

atctgttagg gtttctttgt aaaacccctc atgatttgtt gtattcaaga taaggcattg    240

gctcgtgttg atcaagatga cttgatg                                        267


<210> SEQ ID NO 104
<211> LENGTH: 250
<212> TYPE: DNA
<213> ORGANISM: Brassica napus
```

<400> SEQUENCE: 104

```
cattcgacag aaaggaacga gtgaaaagag tttggatctt taagcttttt gatcatgtgg     60

gtttgacaaa agagtttctt acagagatct ttggcattct gtccacctcc cctacctatg    120

tatatgtgta ttatctacgt tgtgttttgt gagggggagg tgggcatact gccaacagag    180

atctgttagg gtttctttgt aaggcattca agataaggca ttggctcgtg ttgatcaaga    240

tgacttgatg                                                           250
```

<210> SEQ ID NO 105
<211> LENGTH: 102
<212> TYPE: DNA
<213> ORGANISM: Brassica napus

<400> SEQUENCE: 105

```
agggggaggt gggcatactg ccaacagaga tctgttaggg tttctttgta aaacccctca     60

tgatttgttg tattcaagat aaggcattgg ctcgtgttga tc                       102
```

<210> SEQ ID NO 106
<211> LENGTH: 85
<212> TYPE: DNA
<213> ORGANISM: Brassica napus

<400> SEQUENCE: 106

```
agggggaggt gggcatactg ccaacagaga tctgttaggg tttctttgta aggtattcaa     60

gataaggcat tggctcgtgt tgatc                                           85
```

<210> SEQ ID NO 107
<211> LENGTH: 1157
<212> TYPE: DNA
<213> ORGANISM: Brassica napus

<400> SEQUENCE: 107

```
atggctgccc ccaactccat tttcaccacc gctccgtcga gaaatctcgc acctatctct     60

cttcaccagt cattatcttc accgttgagt ctccggatca ctaaatcgaa ctccgtcgcg    120

tttcgtccca aaccccgatc cagctcgctc gtcttctgct ccaccgatga atcaaagatc    180

tccgcagaga aagagatccc aattgaactt agtaagtaaa actttctcta atggcattat    240

aacttaaaaa ttcgaaaatt tcaattaaaa taaataaata attttttgca gggtacgagg    300

cttatccgac agtgatggac attaaccaga tacgagagat tttgcctcac aggtgaataa    360

atttctctta cacgctgttt ctctagctga agttgtattg ttctgattcc ttgtcttaat    420

ttttttttta taaaaaaaaa atcgattttg gactgttgtg taggttcccg tttctgttag    480

tggatagagt gatagagtac acagctggtg aatctgcggt agctatcaag aacgttacca    540

ttaatgacaa tttctttcct gggcatttcc ctgagaggcc cattatgcct ggtgtcctca    600

tggttgaggt aatcatctca ttgcatgctt ctctcttttt gcaatacatt catagttcaa    660

gagaagttat ttgatctcca gagttagaag aatacttatt agtgtatata tactagccgg    720

agttagttga attgttactt atcatagcta tatatgaaca tttgctttat aagtaaaacc    780

agtagcagtc tgttccagat gtatgtgata tgaaatgagt aggggactca ttgtgtgtta    840

ataagagcta tatatagatt gcctcatcaa ttagtttttt ttttttttgg tttccacagg    900

ccatggctca ggtgggaggt atagtgatgc taaatccaga agtgggcgga tctaaaagca    960

acttcttctt tgctggagtc gacaaagtga gattcagaaa gcctgtgatt gcaggtgaca   1020
```

ctctggtgat gaggatgacg cttgtgaagc tgcagaagcg gtttgggata gccaaaatgg 1080
aagggaaagc atacgtaggg aacactttgg tatgcgaagg agagttcttg atggctatgg 1140
ggaaagaaga ggagtga 1157

<210> SEQ ID NO 108
<211> LENGTH: 700
<212> TYPE: DNA
<213> ORGANISM: Brassica napus

<400> SEQUENCE: 108
ggagaaagag atcccaatag agctcagtaa gcttaccatc tcataacaat ctgattacaa 60
atcaaaaaat ttaattaaaa aataaataaa taaaattggg cagggtacga ggcttttccg 120
acagtgatgg acataaccag atacgtgaga tattgcctca caggtgaata attttattac 180
acactgtttc tccaaactga agttgttttg ttctgattcg atgtctggac tggttgtgtt 240
atgtaggttc ccgtttctgt tagtggatag agtgatagag tacacacctg gtgtatctgc 300
tgtagctatc aaaaacgtta ccattaatga taatttcttt cctgggcatt ttcctgagag 360
gcccattatg cctggagtcc tcatggttga ggtaaaatct cattgcaagc ttcactcctt 420
tttttgctac ttgatcttta gagatcttgg ctttgcttag gctgggttaa tagagagtaa 480
gattagcttg ttttgaagga taccccctgga tcataccttt atatcaagag ttgctctatt 540
acgacataac taaagccagt agcatctatt ccagccaaaa tacatgatga gtctcctaat 600
gatttcatgc tacatagatt ttcagacatc ttgtacttaa aaattattca aagcattaaa 660
atatactttc tccgtttcat aaaaaaatgc atgttttaga 700

<210> SEQ ID NO 109
<211> LENGTH: 627
<212> TYPE: DNA
<213> ORGANISM: Brassica napus

<400> SEQUENCE: 109
ggagaaagag atcccaatag agctcagtaa gcttaccatc tcataacaat ctgattacaa 60
atcaaaaaat ttaattaaaa aataaataaa taaaattggg cagggtacga ggcttttccg 120
acagtgatgg acataaccag atacgtgaga tattgcctca caggtgaata attttattac 180
acactgtttc tccaaactga agttgttttg ttctgattcg atgtctggac tggttgtgtt 240
atgtaggttc ccgtttctgt tagtggatag agtgatagag tacacactct attccagcct 300
ggagtcctca tggttgaggt aaaatctcat tgcaagcttc actccttttt ttgctacttg 360
atctttagag atcttggctt tgcttaggct gggttaatag agagtaagat tagcttgttt 420
tgaaggatac ccctggatca tacctttata tcaagagttg ctctattacg acataactaa 480
agccagtagc atctattcca gccaaaatac atgatgagtc tcctaatgat ttcatgctac 540
atagattttc agacatcttg tacttaaaaa ttattcaaag cattaaaata tactttctcc 600
gtttcataaa aaaatgcatg ttttaga 627

<210> SEQ ID NO 110
<211> LENGTH: 123
<212> TYPE: DNA
<213> ORGANISM: Brassica napus

<400> SEQUENCE: 110
ttagtggata gagtgataga gtacacacct ggtgtatctg ctgtagctat caaaaacgtt 60
accattaatg ataatttctt tcctgggcat tttcctgaga ggcccattat gcctggagtc 120

```
ctc                                                                123

<210> SEQ ID NO 111
<211> LENGTH: 50
<212> TYPE: DNA
<213> ORGANISM: Brassica napus

<400> SEQUENCE: 111

ttagtggata gagtgataga gtacacactc ccattatgcc tggagtcctc              50

<210> SEQ ID NO 112
<211> LENGTH: 646
<212> TYPE: DNA
<213> ORGANISM: Brassica napus

<400> SEQUENCE: 112

ggatagagtg atagagtaca cagctggtga atctgcggta gctatcaaga acgttaccat    60

taatgacaat ttctttcctg ggcatttccc tgagaggccc attatgcctg gtgtcctcat   120

ggttgaggta atcatctcat tgcatgcttc tctcttttg caatacattc atagttcaag    180

agaagttatt tgatctccag agttagaaga atacttatta gtgtatatat actagccgga   240

gttagttgaa ttgttactta tcatagctat atatgaacat ttgctttata agtaaaacca   300

gtagcagtct gttccagatg tatgtgagat gaaatgagta ggagactcat tgtgtgttaa   360

taagagctat atatagattg cctcatcaat tagttttttt tttttttggt ttccacaggc   420

catggctcag gtgggaggta tagtgatgct aaatccagaa gtgggcggat ctaaaagcaa   480

cttcttcttt gctggagtcg acaaagtgag attcagaaag cctgtgattg caggtgacac   540

tctggtgatg aggatgacgc ttgtgaagct gcagaagcgg tttgggatag ccaaaatgga   600

agggaaagca tacgtaggga acactttggt atgcgaagga gagttc                  646

<210> SEQ ID NO 113
<211> LENGTH: 558
<212> TYPE: DNA
<213> ORGANISM: Brassica napus

<400> SEQUENCE: 113

ggatagagtg atagagtaca cagctggtga atctgcggta gctatcaaga acgttaccat    60

taatgacaat ttctttcctg ggcatttccc tgagaggccc attatgcctg gtgtcctcat   120

ggttgaggta atcatctcat tgcatgcttc tctcttttg caatacattc atagttcaag    180

agaagttatt tgatctccag agttagaaga atacttatta gtgtatatat actagccgga   240

gttagttgaa ttgttactta tcatagctat atatgaacat ttgctttata agtaaaacca   300

gtagcagtct gttccagatg tatgtgagat gaaatgagta ggagactcat tgtgtgttaa   360

taagagctat atatagattg cctcatcaat tagttttttt tttttttggt ttccacaggc   420

catggctcag gtgggaggta tagtgatgct aaatccagaa gtgggcggat ctaaaagcaa   480

cttcttcttt gctggagtcg acaaagtgag attcagaaag cctgtgatga ggatgacgct   540

tgtgaagctg cagaagcg                                                 558

<210> SEQ ID NO 114
<211> LENGTH: 106
```

-continued

```
<212> TYPE: DNA
<213> ORGANISM: Brassica napus

<400> SEQUENCE: 114

ggagtcgaca aagtgagatt cagaaagcct gtgattgcag gtgacactct ggtgatgagg     60

atgacgcttg tgaagctgca gaagcggttt gggatagcca aaatgg                   106


<210> SEQ ID NO 115
<211> LENGTH: 85
<212> TYPE: DNA
<213> ORGANISM: Brassica napus

<400> SEQUENCE: 115

ggagtcgaca aagtgagatt cagaaagcct gtgatgagga tgacgcttgt gaagctgcag     60

aagcggtttg ggatagccaa aatgg                                           85


<210> SEQ ID NO 116
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 116

Leu Ala Gly Leu Ile Asp Ala Asp Gly
1               5


<210> SEQ ID NO 117
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 117

Leu Ala Gly Leu Ile Asp Ala Asp Gly
1               5


<210> SEQ ID NO 118
<211> LENGTH: 129
<212> TYPE: DNA
<213> ORGANISM: Brassica napus

<400> SEQUENCE: 118

acgcttttgt ccttcttctg gcctgtattg actctcgcta tttgtttgtt tcctgtgtac     60

ccacaccgtt gcaaactcat tgttctctac tcatgtgctg gcattctttt gatgattctc    120

tccttgctt                                                            129
```